(12) United States Patent
Liverton et al.

(10) Patent No.: US 8,461,107 B2
(45) Date of Patent: Jun. 11, 2013

(54) HCV NS3 PROTEASE INHIBITORS

(75) Inventors: Nigel J. Liverton, Harleysville, PA (US); John A. McCauley, Maple Glen, PA (US); John W. Butcher, Telford, PA (US); Kevin F. Gilbert, Barto, PA (US); Charles J. McIntyre, Lansdale, PA (US); Michael T. Rudd, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 164 days.

(21) Appl. No.: 12/989,672

(22) PCT Filed: Apr. 16, 2009

(86) PCT No.: PCT/US2009/040815
§ 371 (c)(1),
(2), (4) Date: Oct. 26, 2010

(87) PCT Pub. No.: WO2009/134624
PCT Pub. Date: Nov. 5, 2009

(65) Prior Publication Data
US 2011/0046161 A1    Feb. 24, 2011

Related U.S. Application Data

(60) Provisional application No. 61/125,688, filed on Apr. 28, 2008.

(51) Int. Cl.
*A61K 38/00*    (2006.01)

(52) U.S. Cl.
USPC .......................................................... 514/3.7

(58) Field of Classification Search
None
See application file for complete search history.

(56) References Cited

U.S. PATENT DOCUMENTS

| | | | |
|---|---|---|---|
| 3,480,613 A | 11/1969 | Walton | |
| 6,323,180 B1 | 11/2001 | Llinas-Brunet et al. | |
| 6,608,027 B1 | 8/2003 | Tsantrizos et al. | |
| 6,777,395 B2 | 8/2004 | Bhat et al. | |
| 6,955,174 B2 | 10/2005 | Joye et al. | |
| 7,470,664 B2 | 12/2008 | Holloway et al. | |
| 7,973,040 B2 | 7/2011 | Harper et al. | |
| 2002/0019363 A1 | 2/2002 | Ismaili et al. | |
| 2002/0107138 A1 | 8/2002 | Hoveyda et al. | |
| 2003/0236216 A1 | 12/2003 | Devos et al. | |
| 2004/0006007 A1 | 1/2004 | Gosselin et al. | |
| 2004/0063658 A1 | 4/2004 | Roberts et al. | |
| 2004/0067901 A1 | 4/2004 | Bhat et al. | |
| 2004/0229776 A1 | 11/2004 | Chen et al. | |
| 2004/0229818 A1 | 11/2004 | Llinas-Brunet et al. | |
| 2004/0254159 A1 | 12/2004 | Hasvold et al. | |
| 2004/0266668 A1 | 12/2004 | Nakajima et al. | |
| 2005/0020503 A1 | 1/2005 | Llinas-Brunet et al. | |
| 2005/0038240 A1 | 2/2005 | Connolly et al. | |
| 2006/0257980 A1 | 11/2006 | Li | |
| 2007/0027071 A1 | 2/2007 | Holloway et al. | |
| 2010/0029666 A1 | 2/2010 | Harper et al. | |
| 2010/0099695 A1 | 4/2010 | Liverton et al. | |
| 2010/0298210 A1 | 11/2010 | Liverton et al. | |

FOREIGN PATENT DOCUMENTS

| | | |
|---|---|---|
| EP | 1719773 A1 | 11/2006 |
| GB | 2337262 A | 11/1999 |
| GB | 2430621 A | 4/2007 |
| WO | 97/041211 A1 | 11/1997 |
| WO | 98/022496 A2 | 5/1998 |
| WO | 98/046630 A1 | 10/1998 |
| WO | 99/07733 A2 | 2/1999 |
| WO | 99/07734 A2 | 2/1999 |
| WO | 99/38888 A1 | 8/1999 |
| WO | 99/43691 A1 | 9/1999 |
| WO | 99/50230 A1 | 10/1999 |
| WO | 99/64442 A1 | 12/1999 |
| WO | 00/09543 A2 | 2/2000 |
| WO | 00/09546 A2 | 2/2000 |
| WO | 00/25780 A1 | 5/2000 |
| WO | 00/59929 A1 | 10/2000 |
| WO | 01/00622 A1 | 1/2001 |
| WO | 01/47883 A1 | 7/2001 |

(Continued)

OTHER PUBLICATIONS

Youwei Yan et al., Complex of NS3 protease and NS4A peptide of BK strain hepatitis C virus: A 2.2 Angstrom resolution structure in a hexagonal crystal form, 7 Protein Science 837 (1998).

Youla S. Tsantrizos, The Design of a Potent Inhibitor of the Hepatitis C Virus NS3 Protease: BILN 2061—From the NMR Tube to the Clinic, Biopolymers (Peptide Science), vol. 76, pp. 309-323 (2004).

International Preliminary Report on Patentability, International Application No. PCT/US20091040815, Applicant file reference MRLIFD22562, dated Nov. 2, 2010.

Brian W Dymock et al., "Novel Approaches to the Treatment of Hepatitis C Virus Infection," 11 Antiviral Chemistry & Chemotherapy 79-96 (2000).

(Continued)

*Primary Examiner* — Thomas Heard
(74) *Attorney, Agent, or Firm* — Julie M. Lake; Sheldon O. Heber

(57) ABSTRACT

The present invention relates to macrocyclic compounds of formula (I) that are useful as inhibitors of the hepatitis C virus (HCV) NS3 protease, their synthesis, and their use for treating or preventing HCV infections.

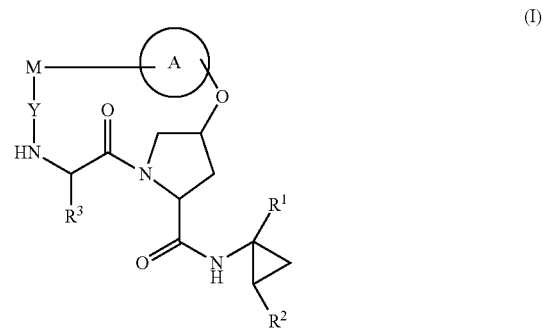

(I)

26 Claims, No Drawings

FOREIGN PATENT DOCUMENTS

| | | |
|---|---|---|
| WO | 01/60379 A1 | 8/2001 |
| WO | 01/68663 A1 | 9/2001 |
| WO | 01/77091 A2 | 10/2001 |
| WO | 01/77113 A2 | 10/2001 |
| WO | 01/79246 A2 | 10/2001 |
| WO | 01/90121 A2 | 11/2001 |
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |
| WO | 02/48116 A2 | 6/2002 |
| WO | 02/48165 A2 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | 02/100415 A2 | 12/2002 |
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | 03/064455 A2 | 8/2003 |
| WO | 03/068244 A1 | 8/2003 |
| WO | 03/093290 A2 | 11/2003 |
| WO | 03/099274 A1 | 12/2003 |
| WO | 2004/000858 A2 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/011478 A2 | 2/2004 |
| WO | 2004/013300 A2 | 2/2004 |
| WO | 2004/028481 A2 | 4/2004 |
| WO | 2004/041201 A2 | 5/2004 |
| WO | 2004/087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A2 | 1/2005 |
| WO | 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | 2005/070955 A1 | 8/2005 |
| WO | 2005/080399 A1 | 9/2005 |
| WO | 2006/008556 A1 | 1/2006 |
| WO | 2006/020082 A1 | 2/2006 |
| WO | 2006/021341 A1 | 3/2006 |
| WO | 2006/027628 A2 | 3/2006 |
| WO | 2006/029912 A1 | 3/2006 |
| WO | 2006/046030 A1 | 5/2006 |
| WO | 2006/046039 A2 | 5/2006 |
| WO | 2006/119061 A2 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | 2007/029029 A2 | 3/2007 |
| WO | 2007/131966 A1 | 11/2007 |
| WO | 2007/145894 A2 | 12/2007 |
| WO | 2007/148135 A1 | 12/2007 |
| WO | 2008/051475 A2 | 5/2008 |
| WO | 2008/051477 A2 | 5/2008 |
| WO | 2008/051514 A2 | 5/2008 |
| WO | 2008/057028 A1 | 5/2008 |
| WO | 2008/057208 A2 | 5/2008 |
| WO | 2008/057209 A1 | 5/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |

OTHER PUBLICATIONS

Hugo R. Rosen & David R. Gretch, "Hepatitis C virus: current understanding and prospects for future therapies," 5 Molec. Med. Today 393-99 (1999).
Darius Moradpour & Hubert E Blum, "Current and evolving therapies for hepatitis C," 11 Euro. J. Gastroenterol. Hepatol. 1189-1202 (1999).
Ralf Bartenschlager, "Candidate Targets for Hepatitis C Virus-Specific Antiviral Therapy," 40(5-6) Intervirology 378-93 (1997).
Georg M. Lauer & Bruce D. Walker, "Hepatitis C Virus Infection," 345(1) N. Engl. J. Med. 41-52 (2001); correction: 345(19) N. Engl. J. Med. 1425-26 (2001).
Brain W. Dymock, "Emerging therapies for hepatitis C virus infection," 6 Emerging Drugs 13-42 (2001).
Charlene Crabb, Infectious Diseases. "Hard-Won Advances Spark Excitement about Hepatitis C," Science 506-507 (2001).
Rogers E. Harry-O'Kuru et al., "A Short, Flexible Route toward 2'-C-Branched Ribonucleosides," 62 J. Org. Chem. 1754-59 (1997).
Michael S. Wolfe & Rogers E. Harry-O'Kuru, "A Concise Synthesis of 2'-C-Methylribonucleosides," 36(42) Tetrahedron Letters 7611-14 (1995).
Scott J. Miller et al., "Application of Ring-Closing Metathesis to the Synthesis of Rigidified Amino Acids and Peptides," 118 J. Am. Chem. Soc. 9606-14 (1996).
Jason S. Kingsbury et al., "A Recyclable Ru-Based Metathesis Catalyst," 121 J. Am. Chem. Soc. 791-99 (1999).
Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).
Alois Furstner et al., "Total Synthesis and Structural Refinement of the Cyclic Tripyrrole Pigment Nonylprodigiosin," 64 J. Org. Chem. 8275-80 (1999).
Tina M. Trnka & Robert H. Grubbs, "The Development of L2X2R-CHR Olefin Metathesis Catalysts: An Organometallic Success Story," 34 Acc. Chem. Res. 18-29 (2001).
A. Srikrishna et al., "Enantiospecific Construction of the BC-ring System of Taxanes," 45 Tetrahedron Letters 2939-42 (2004).
Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).
Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).
Paola Conti et al., "Chemoenzymatic Synthesis of the Enantiomers of Desoxymuscarine," 9 Tetrahedron: Asymmetry 657-65 (1998).
Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).
D. Becker & N. Haddad, "Steric Effects in Intramolecular [2+2] Photocycloaddition of C=C Double Bonds to Cyclohexenones," 49(4) Tetrahedron 947-64 (1993).
Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).
Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).
Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).
Herbert O. House et al., "Cyclization of Unsaturated Hydroxylamine Derivatives," 41(5) J. Org. Chem. 855-63 (1976).
Theophil Eicher et al., "Bryophyte Constituents; 7: New Synthesis of (+)-Rosmarinic Acid and Related Compounds," Synthesis 755-62 (Jun. 1996).
Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).

Marc-Andre Poupart et al., "Solid-Phase Synthesis of Peptidomimetic Inhibitors for the Hepatitis C Virus NS3 Protease," 66(14) J. Org. Chem. 4743-51 (2001).

Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).

Anthony C. Allison & Elsie M. Eugui, "Immunosuppressive and other anti-rheumatic activities of mycophenolate mofetil," 44 Agents and Actions Supplements 165-88 (1993).

Joel Kirschbaum, "Amantadine," 12 Profiles of Drug Substances, Excipients and Related Methodology 1-36 (1983).

T. K. Chakaborty et al., "Alpha-Phenylglycinol as chiral auxilliary in diastereoselective Strecker synthesis of alpha-amino acids," 51(33) Tetrahedron 9179-90 (1995).

W. Clark Still et al., "Rapid Chromatographic Technique for Preparative Separations with Moderate Resolution," 43(14) J. Org. Chem. 2923-25 (1978).

Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).

Paul Aeberli et al., "Neuropharmacological investigation of N-benzylsulfamides," 10(4) J. Med. Chem. 636-42 (1967).

Nathalie Goudreau & Montse Llinas-Brunet, "The Therapeutic Potential of NS3 Protease Inhibitors in HCV Infection," 14(9) Expert Opinion 1129-44 (2005).

Volker Lohmann et al., "Selective Stimulation of Hepatitis C Virus and Pestivirus NS5B RNA Polymerase Activity by GTP," 274(16) J. Bio. Chem. 10807-15 (1999).

V. Lohmann et al., "Replication of Subgenomic Hepatitis C Virus RNAs in a Hepatoma Cell Line," 285 Science 110-13 (1999).

Kevin X. Chen et al. "Novel Potent Hepatitis C Virus NS3 Serine Protease Inhibitors Derived from Proline-Based Macrocycles," 49 J. Med. Chem. 995-1005 (2006).

Yuri Goldberg et al., "Highly regioselective bromination of 2,3-dimethylanisole with N-bromosuccinimide," 57 J. Org. Chem. 6374-76 (1992).

Manfred Schlosser et al., "8-Methoxyisoquinoline derivatives through ortho-selective metallation of 2-(3-methoxyphenyl)ethylamines," 32(17) Tetrahedron Letters 1965-66 (1991).

Angela Casini et al., "Carbonic Anhydrase inhibitors inhibition of cytosolic isozymes I and II with sulfamide derivatives," 13(5) Bioorg. Med. Chem. Lett. 837-40 (2003).

Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).

Duane E. Rudisill & J. K. Stille, "Palladium-catalyzed synthesis of 2-substituted indoles," 54(25) J. Org. Chem. 5856-66 (2002).

Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).

Yuusaku Yokoyama et al., "Palladium-Catalyzed Reaction of 3-Bromoindole Derivative with Allyl Esters in the Presence of Hexa-n-butyldistannane," 31(8) Heterocycles 1505-11 (1990).

Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).

John A. McCauley et al., "Bismacrocyclic Inhibitors of Hepatitis C NS3/4a Protease," 47 Angew. Chem. Int. Ed. 9104-07 (2008).

Ashok Arasappan et al., "P2-P4 Macrocyclic inhibitors of hepatitis C virus NS3-4A serine protease," 16 Bioorganic & Medicinal Chemistry Letters 3960-65 (2006).

Official Action mailed on Apr. 14, 2011 in co-pending U.S. Appl. No. 12/447,342.

Response to Official Action filed Aug. 25, 2011 in co-pending U.S. Appl. No. 12/447,342.

Official Action mailed on Nov. 7, 2011 in co-pending U.S. Appl. No. 12/447,342.

Response to Official Action filed on May 4, 2012 in co-pending U.S. Appl. No. 12/447,342.

Official Action mailed on Jul. 18, 2012 in co-pending U.S. Appl. No. 12/447,342.

Response to Official Action filed on Nov. 19, 2012 in co-pending U.S. Appl. No. 12/447,342.

Official Action mailed on Feb. 17, 2011 in co-pending U.S. Appl. No. 12/447,342.

Response to Official Action filed on Mar. 17, 2011 in co-pending U.S. Appl. No. 12/477,342.

HCV NS3 PROTEASE INHIBITORS

CROSS-REFERENCE TO RELATED APPLICATIONS

This application is a National Stage application of International Patent Application No. PCT/US2009/040815, filed Apr. 16, 2009, which claims priority to U.S. Provisional Patent Application No. 61/125,688, filed Apr. 28, 2008.

FIELD OF THE INVENTION

The present invention relates to macrocyclic compounds that are useful as inhibitors of the hepatitis C virus (HCV) NS3 protease, the synthesis of such compounds, and the use of such compounds for treating HCV infection and/or reducing the likelihood or severity of symptoms of HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 3.9 million infected people in the United States alone, according to the U.S. Center for Disease Control, roughly five times the number of people infected with the human immunodeficiency virus (HIV). According to the World Health Organization, there are more than 170 million infected individuals worldwide, with at least 3 to 4 million people being infected each year. Once infected, about 20% of people clear the virus, but about 80% of those infected harbor HCV the rest of their lives. Ten to 20% of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring.

Current treatments for HCV infection are restricted to immunotherapy with recombinant interferon-α alone or in combination with the nucleoside analog ribavirin, and these treatments are of limited clinical benefit. Moreover, there is no established vaccine for HCV. Consequently, there is an urgent need for improved therapeutic agents that effectively combat chronic HCV infection. Treatment of HCV infection has been discussed in the following references: B. Dymock et al., "Novel approaches to the treatment of hepatitis C virus infection," 11 *Antiviral Chem. & Chemotherapy* 79-96 (2000); H. Rosen et al., "Hepatitis C virus: current understanding and prospects for future therapies," 5 *Molec. Med. Today* 393-399 (1999); D. Moradpour et al., "Current and evolving therapies for hepatitis C," 11 *Euro. J. Gastroenterol. Hepatol.* 1189-1202 (1999); R. Bartenschlager, "Candidate Targets for Hepatitis C Virus-Specific Antiviral Therapy," 40 *Intervirology* 378-393 (1997); G. M. Lauer & B. D. Walker, "Hepatitis C Virus Infection," 345 *N. Engl. J. Med.* 41-52 (2001); B. W. Dymock, "Emerging therapies for hepatitis C virus infection," 6 *Emerging Drugs* 13-42 (2001); and C. Crabb, "Hard-Won Advances Spark Excitement about Hepatitis C," *Science:* 506-507 (2001).

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein. Because it is responsible for an intramolecular cleavage at the NS3/4A site and for downstream intermolecular processing at the NS4A/4B, NS4B/5A and NS5A/5B junctions, the NS3 protease is considered a prime drug target. Previous research has identified classes of peptides, such as hexapeptides as well as tripeptides discussed in U.S. Patent Application Publications US2005/0020503, US2004/0229818, and US2004/00229776, showing degrees of activity in inhibiting the NS3 protease. The aim of the present invention is to provide further compounds which exhibit activity against the HCV NS3 protease.

SUMMARY OF THE INVENTION

The present invention relates to macrocyclic compounds of formula (I) and pharmaceutically acceptable salts thereof. These compounds are useful in the inhibition of HCV (hepatitis C virus) NS3 (non-structural 3) protease, the prevention or treatment of one or more of the symptoms of HCV infection, either as compounds or their pharmaceutically acceptable salts, or as pharmaceutical composition ingredients. As pharmaceutical composition ingredients, these compounds and salts may be the primary active therapeutic agent, and, when appropriate, may be combined with other therapeutic agents including but not limited to other HCV antivirals, anti-infectives, immunomodulators, antibiotics or vaccines. More particularly, the present invention relates to a compound of formula (I) and a pharmaceutically acceptable salt thereof:

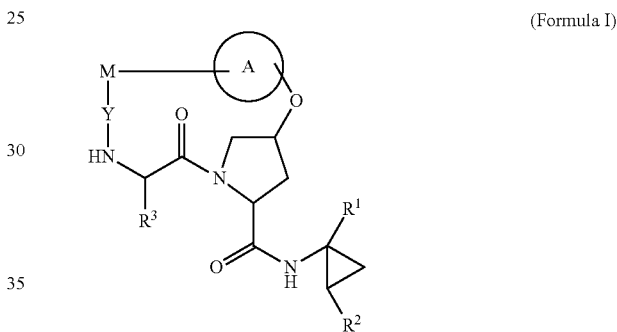

(Formula I)

wherein:

is selected from the group consisting of:

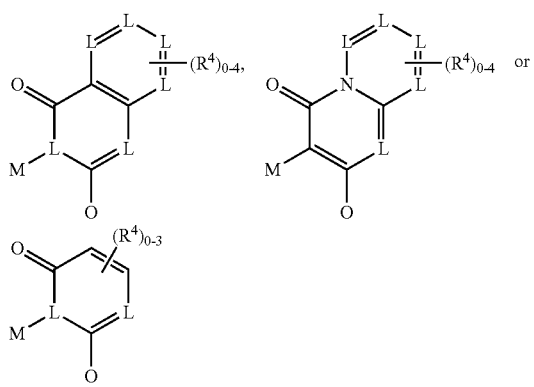

wherein:
each L is independently selected from the group consisting of N and CH, provided that the total number of L that are N is from 1 to 4;

$R^1$ is selected from the group consisting of —$CO_2H$, and —$CONHSO_2$(cyclopropyl);

$R^2$ is selected from the group consisting of ethyl and ethenyl;

$R^3$ is selected from the group consisting of cyclopentyl, cyclohexyl, and —$C(CH_3)_3$;

each $R^4$ is independently selected from the group consisting of halogen atoms, $C_1$-$C_4$ alkoxy, $C_1$-$C_7$ alkyl, $C_2$-$C_7$ alkenyl, —CN, —$CF_3$, —$OCF_3$, $SCH_3$, —$SO_2(CH_3)$, $C_3$-$C_8$ cycloalkyl, $C_3$-$C_8$ cycloalkoxy, $C_1$-$C_6$ haloalkyl, phenyl, naphthyl and heteroaryl groups, wherein each said $R^4$ heteroaryl is selected from the group consisting of 5- and 6-membered aromatic rings having 1, 2 or 3 heteroatoms independently selected from N, O and S, and said $R^4$ heteroaryl is attached through a ring atom selected from C or N, each said $R^4$ phenyl, naphthyl and heteroaryl groups are substituted with 0 to 4 substituents independently selected from the group consisting of halogen atoms, —$OR^5$, —$SR^5$, —$N(R^5)_2$, —$N(C_1$-$C_6$ alkyl)$O(C_1$-$C_6$ alkyl), $C_1$-$C_6$ alkyl, $C_1$-$C_6$ haloalkyl, ($C_1$-$C_6$ haloalkoxy), —$NO_2$, —CN, —$CF_3$, —$SO_2(C_1$-$C_6$ alkyl), —$S(O)(C_1$-$C_6$ alkyl), —$NR^5SO_2R^6$, $SO_2N(R^6)_2$, —$NHCOOR^6$, —$NHCOR^6$, —$NHCONHR^6$, —$CO_2R^5$, —$C(O)R^5$, and —$CON(R^5)_2$, and 2 adjacent substituents of said $R^4$ phenyl, naphthyl and heteroaryl groups may be taken together to form a 3- to 6-membered cyclic ring containing 0 to 3 heteroatoms independently selected from N, O and S;

each $R^5$ is independently H or $C_1$-$C_6$ alkyl;

each $R^6$ is independently H, $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl);

Y is selected from the group consisting of —C(O)—, —C(O)O— and —C(O)NH—;

M is selected from the group consisting of $C_4$-$C_7$ alkylene and $C_4$-$C_7$ alkenylene, wherein said M is substituted with 0 to 3 substituents independently selected $C_1$-$C_8$ alkyl, provided that two adjacent substituents can together form a 3 to 6 membered ring.

The present invention also includes pharmaceutical compositions containing a compound of the present invention and methods of preparing such pharmaceutical compositions. The present invention further includes methods of treating or reducing the likelihood or severity of one or more symptoms of HCV infection.

Other embodiments, aspects and features of the present invention are either further described in or will be apparent from the ensuing description, examples and appended claims.

DETAILED DESCRIPTION OF THE INVENTION

The present invention includes compounds of formula (I), and pharmaceutically acceptable salts thereof. These compounds and their pharmaceutically acceptable salts are HCV protease inhibitors (e.g., HCV NS3 protease inhibitors). Preferred compounds are those with high activity (e.g., Ki of 5 nM or less, 1 nM or less, 0.5 nM or less, or 0.1 mM or less) against HCV NS3 genotype 1b R155K. R155K is a HCV 1b mutation that occurs in nature and which provides resistance against some NS3 protease inhibitors. Example 85 infra illustrates the ability of different compounds to provide high activity against such a mutation.

Reference to formula I compounds throughout the present application includes reference to compounds within formula I including different embodiment and subgeneric formula (formula Ia and Ib).

Different embodiments for formula I compounds include the following:

In a first embodiment,

is selected from the group consisting of:

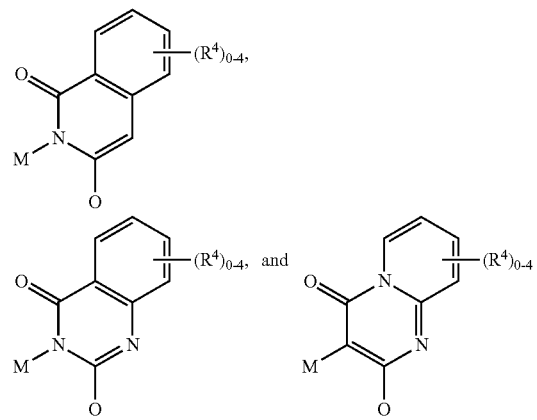

and the other substitutents are as provided for formula I above. In an aspect of the first embodiment, 0 or 1 $R^4$ is present and, if present, is selected from the group consisting of —Br, —Cl, —CN, phenyl, —O-phenyl, —$OCF_3$, —$OCH_3$, —C(O)OH, —$CH_3$ and —$C(O)CH_3$.

In a second embodiment, $R^1$ is —$CO_2H$, and the other substituents are as provided in formula I above or in the above first embodiment.

In a third embodiment, $R^1$ is —$C(O)NHSO_2$cyclopropyl, and the other substituents are as provided in formula I above or in the first embodiment.

In a fourth embodiment, $R^2$ is —$CH_2CH_3$, and the other substituents are as provided in formula I above or in the first to third embodiments.

In a fifth embodiment, $R^2$ is —CH=$CH_2$, and the other substituents are as provided in formula I above or in the first to third embodiments.

In a sixth embodiment, $R^3$ is cyclopentyl, and the other substituents are as provided in formula I above or the first through fifth embodiments.

In a seventh embodiment, $R^3$ is cyclohexyl, and the other substituents are as provided in formula I above or in the first through fifth embodiments.

In a eighth embodiment $R^3$ is —$C(CH_3)_3$, and the other substituents are as provided in formula I above or the first through fifth embodiments.

In a ninth embodiment, M is selected from the group consisting of

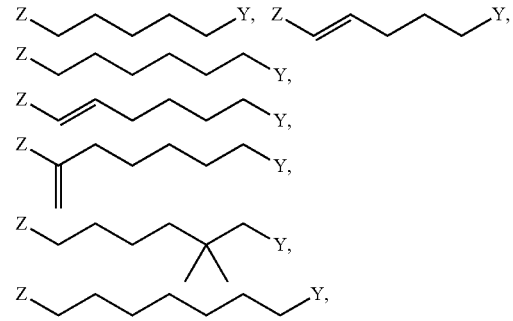

-continued

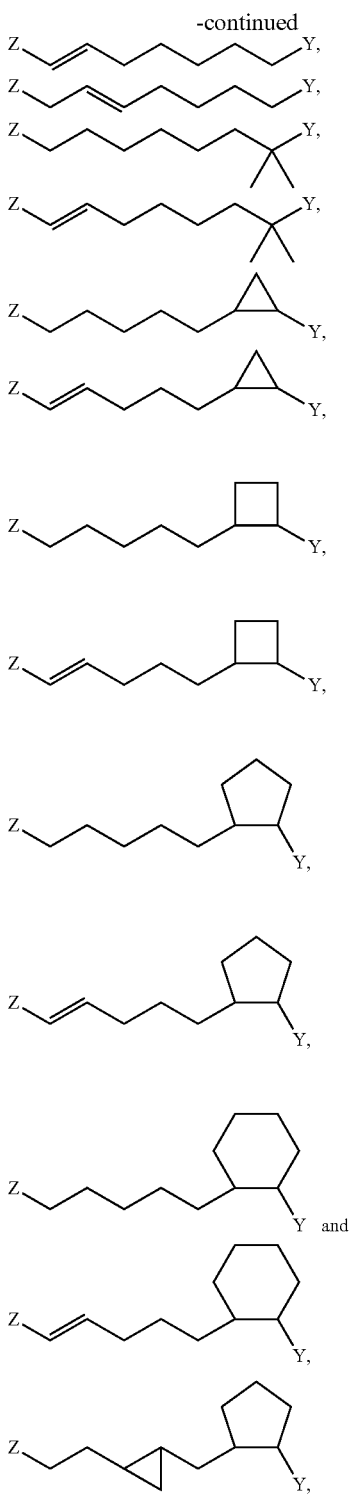

where Z is

and the other substituents are as provided in formula I above or the first through eighth embodiments.

In another aspect of the invention, the formula I compound has the following structure:

formula Ia

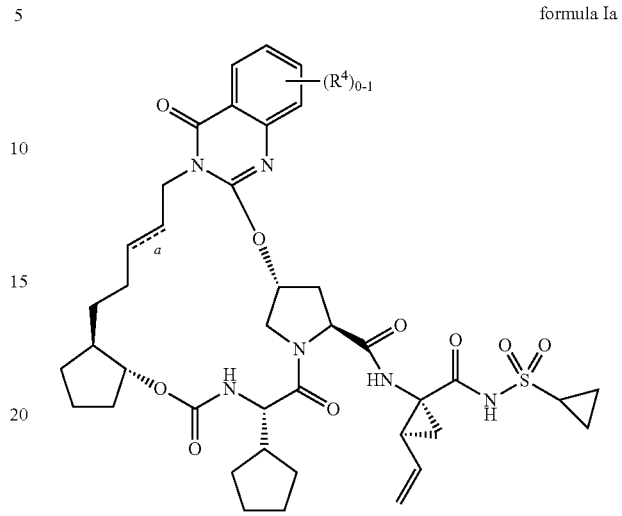

wherein "a" is an optionally present bond and R⁴ if present is selected from the group consisting of —Br, —Cl, —CN, phenyl, —O-phenyl, —OCF₃, —OCH₃, —C(O)OH, —CH₃ and —C(O)CH₃.

Different embodiments for formula Ia compounds include the following:

In a first embodiment R⁴ is present and is selected from the group consisting of —Br, —CN, —OCF₃, —OCH₃, —C(O)OH, —CH₃ and —C(O)CH₃.

In a second embodiment R⁴ is not present.

In a third embodiment "a" is not present and R⁴ is as provided in the general formula Ia above, or in the first or second embodiments.

In a fourth embodiment, "a" is present and R⁴ is as provided in the general formula Ia above, or in the first or second embodiments.

In another aspect of the invention, the formula I compound has the following structure:

Formula Ib

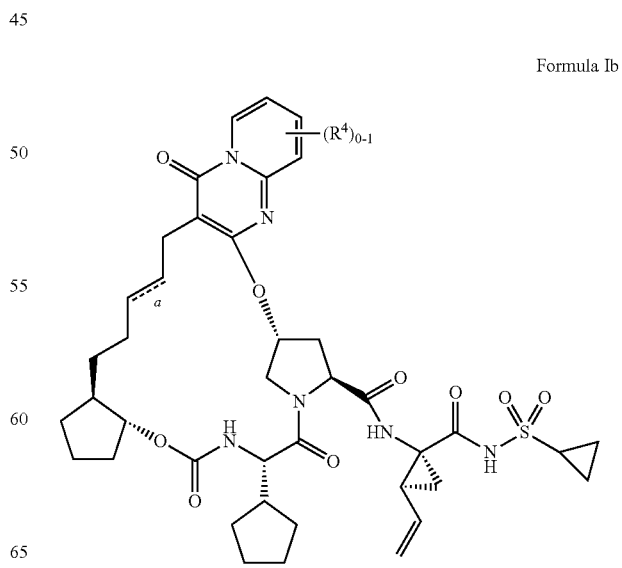

wherein "a" is an optionally present bond and $R^4$ if present is selected from the group consisting of —Br, —Cl, —CN, phenyl, —O-phenyl, —OCF$_3$, —OCH$_3$, —C(O)OH, —CH$_3$ and —C(O)CH$_3$.

Different embodiments for formula Ib compounds include the following:

In a first embodiment $R^4$ is present and is selected from the group consisting of —Br, —CN, —OCF$_3$, —OCH$_3$, —C(O)OH, —CH$_3$ and —C(O)CH$_3$.

In a second embodiment $R^4$ is not present.

In a third embodiment "a" is not present and $R^4$ is as provided in the general formula Ia above, or in the first or second embodiments.

In a fourth embodiment, "a" is present and $R^4$ is as provided in the general formula Ia above, or in the first or second embodiments, In another embodiment of the invention, the compound of the invention is a compound provided in Examples 1 through 84 shown below or a pharmaceutically acceptable salt thereof.

Other embodiments of the present invention include the following:

(a) A pharmaceutical composition comprising an effective amount of a compound of formula (I) and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination which is (i) a compound of formula (I) and (ii) a second therapeutic agent selected from the group consisting of HCV antiviral agents, immunomodulators, and anti-infective agents; wherein the compound of formula (I) and the second therapeutic agent are each employed in an amount that renders the combination effective for inhibiting HCV NS3 protease, or for treating HCV infection and/or reducing the likelihood or severity of symptoms of HCV infection.

(e) The combination of (d), wherein the HCV antiviral agent is an antiviral selected from the group consisting of HCV protease inhibitors and HCV NS5B polymerase inhibitors.

(f) A method of inhibiting HCV NS3 protease in a subject in need thereof which comprises administering to the subject an effective amount of a compound of formula (I).

(g) A method of treating HCV infection and/or reducing the likelihood or severity of symptoms of HCV infection in a subject in need thereof which comprises administering to the subject an effective amount of a compound of formula (I).

(h) The method of (g), wherein the compound of formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV NS3 protease in a subject in need thereof which comprises administering to the subject the pharmaceutical composition of (a), (b), or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b), or (c) or the combination of (d) or (e).

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (k) above are understood to include all embodiments of the compounds, including such embodiments as result from combinations of embodiments.

The present invention also includes a compound of the present invention for use (i) in, (ii) as a medicament for, or (iii) in the preparation of a medicament for: (a) inhibiting HCV NS3 protease, or (b) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt.

As used herein, all ranges are inclusive, and all sub-ranges are included within such ranges, although not necessarily explicitly set forth. In addition, the term "or," as used herein, denotes alternatives that may, where appropriate, be combined; that is, the term "or" includes each listed alternative separately as well as their combination if the combination is not mutually exclusive.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl. Alkyl groups may be substituted as indicated.

The term "halogenated" refers to a group or molecule in which a hydrogen atom has been replaced by a halogen. Similarly, the term "haloalkyl" refers to a halogenated alkyl group. The term "halogen" (or "halo") refers to atoms of fluorine, chlorine, bromine and iodine (alternatively referred to as fluoro, chloro, bromo, and iodo).

The term "alkoxy" refers to an "alkyl-O—" group. Alkoxy groups may be substituted as indicated.

The term "alkenylene" refers to any linear or branched chain alkenylene group containing a double and having a number of carbon atoms in the specified range. Thus, for example, "—$C_{2-6}$ alkenylene-" refers to any of the $C_2$ to $C_6$ linear or branched alkenylene. Alkenylene groups may be substituted as indicated.

The term "alkylene" refers to any linear or branched chain alkylene group (or alternatively "alkanediyl") having a number of carbon atoms in the specified range. Thus, for example, "—$C_{1-6}$ alkylene-" refers to any of the $C_1$ to $C_6$ linear or branched alkylenes. Examples of alkylenes include —(CH$_2$)$_{1-6}$—, —(CH$_2$)$_{1-4}$—, —(CH$_2$)$_{1-3}$—, (CH$_2$)$_{1-2}$—, —CH$_2$— and —CH(CH$_3$)—. Alkylene groups may be substituted as indicated.

The term "cycloalkyl" refers to any cyclic ring of an alkane or alkene having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl. The term "cycloalkoxy" refers to a "cycloalkyl-O—" group. Cycloalkyl groups may be substituted as indicated.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. Carbocycle groups may be substituted as indicated, for example with $C_{1-6}$ alkyl, $C_{2-6}$ alkenyl, $C_{2-6}$ alkynyl, aryl, halogen, —$NH_2$ or —OH. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which both rings are saturated is a saturated bicyclic ring system. Saturated carbocyclic rings are also referred to as cycloalkyl rings, e.g., cyclopropyl, cyclobutyl, etc. A fused bicyclic carbocycle in which one or both rings are unsaturated is an unsaturated bicyclic ring system. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include

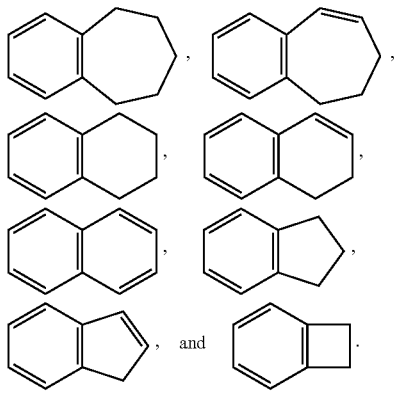

Depicted ring systems include, where appropriate, an indication of the variable to which a particular ring atom is attached. For example, in the structure

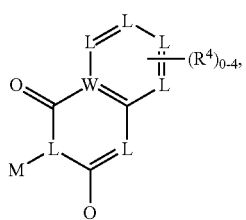

the variable $R^4$ is shown as a floating variable which can be attached to any ring atom, provided that such attachment results in formation of a stable ring.

The term "aryl" refers to aromatic mono- and poly-carbocyclic ring systems, also referred to as "arenes," wherein the individual carbocyclic rings in the polyring systems are fused or attached to each other via a single bond. Suitable aryl groups include phenyl, naphthyl, and biphenylenyl. Aryl groups may be substituted as indicated.

The terms "heteroaryl" and "heteroaromatic ring" refer to a stable 5- or 6-membered monocyclic aromatic ring, a stable 7- to 12-membered bicyclic ring system, or a stable 11- to 15-membered tricyclic ring system, which consists of carbon atoms and one or more heteroatoms selected from N, O and S. In the case of substituted heteraromatic rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Unless otherwise specifically noted a particular group such as alkyl, cycloalkyl, aryl and heteroaryl groups are unsubstituted. In different embodiments the alkyl, cycloalkyl, aryl and heteroaryl groups are substituted with one to three substitutents selected from the group consisting of: halo, $C_1$-$C_{20}$ alkyl, —$CF_3$, —$NH_2$, —$N(C_1$-$C_6$ alkyl$)_2$, —$NO_2$, oxo, —CN, —$N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl) C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, haloaryl, halo-aralkyl, halo-heteroaryl, halo-heterocyclylalkyl, cyano-aryl, cyano-aralkyl, cyano-heterocycle and cyano-heterocyclylalkyl.

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

When any variable (e.g. L) occurs more than one time in any constituent or in formula (I) or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., aryl or a heteroaryl ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

Reference to a compound also includes stable complexes of the compound such as a stable hydrate.

As would be recognized by one of ordinary skill in the art, certain of the compounds of the present invention can exist as tautomers. For the purposes of the present invention a reference to a compound of formula (I) is a reference to the compound per se, or to any one of its tautomers per se, or to mixtures of two or more tautomers.

The compounds of the present inventions are useful in the inhibition of HCV protease (e.g., HCV NS3 protease) and the treatment of HCV infection and/or reduction of the likelihood or severity of symptoms of HCV infection. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus, the compounds of this invention may be commercial products to be sold for these purposes.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts fowled with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt and other agents.

As used herein, the teen "prodrug" is intended to encompass an inactive drug form or compound that is converted into an active drug form or compound by the action of enzymes, chemicals or metabolic processes in the body of an individual to whom it is administered.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HCV NS3 protease and treating HCV infection and/or reducing the likelihood or severity of symptoms of HCV infection, the compounds of the present invention, optionally in the form of a salt, can be administered by means that produces contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following routes: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further guidance for methods suitable for use in preparing pharmaceutical compositions of the present invention and of ingredients suitable for use in said compositions is provided in *Remington's Pharmaceutical Sciences*, $20^{th}$ edition (ed. A. R. Gennaro, Mack Publishing Co., 2000).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention also relates to a method of inhibiting HCV NS3 protease, inhibiting HCV replication, or preventing or treating HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes recombinant interferon-α2a (such as ROFERON interferon available from Hoffmann-LaRoche, Nutley, N.J.), pegylated interferon-α2a (PEGASYS), interferon-α2b (such as INTRON-A interferon available from Schering Corp., Kenilworth, N.J.), pegylated interferon-α2b (PEGINTRON), a recombinant consensus interferon (such as interferon alphacon-1), and a purified interferon-α product. Amgen's recombinant consensus interferon has the brand name INFERGEN. Levovirin is the L-enantiomer of ribavirin which has shown immunomodulatory activity similar to ribavirin. Viramidine represents an analog of ribavirin disclosed in WO 01/60379. The individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in International Patent Application Publications WO 98/22496, WO 98/46630, WO 99/07733, WO 99/07734, WO 99/38888, WO 99/50230, WO 99/64442, WO 00/09543, WO 00/59929, WO 02/48116 and WO 02/48172, British Patent No. GB 2 337 262, and U.S. Pat. No. 6,323,180. Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in International Patent Application Publications WO 97/41211 and WO 01/00622; another IMPDH inhibitor, such as that disclosed in WO 00/25780; or mycophenolate mofetil. See A. C. Allison and E. M. Eugui, 44 (Suppl.) *Agents Action* 165 (1993).

For the treatment of HCV infection, the compounds of the present invention may also be administered in combination with the antiviral agent amantadine (1-aminoadamantane). For a comprehensive description of this agent, see J. Kirschbaum, 12 *Anal. Profiles Drug Subs.* 1-36 (1983).

For the treatment of HCV infection, the compounds of the present invention may also be administered in combination with the antiviral agent polymerase inhibitor R7128 (Roche).

The compounds of the present invention may also be combined for the treatment of HCV infection with antiviral 2'-C-branched ribonucleosides disclosed in R. E. Harry-O'Kuru et al., 62 *J. Org. Chem.* 1754-59 (1997); M. S. Wolfe et al., 36 *Tet. Lett.* 7611-14 (1995); U.S. Pat. No. 3,480,613; and International Patent Application Publications WO 01/90121, WO 01/92282, WO 02/32920, WO 04/002999, WO 04/003000 and WO 04/002422; the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in International Patent Application Publications WO 02/51425, assigned to Mitsubishi Pharma Corp.; WO 01/79246, WO 02/32920, WO 02/48165 and WO2005/003147 (including R1656, (2'R)-2'-deoxy-2'-fluoro-2'-C-methylcytidine, shown as compounds 3-6 on page 77); WO 01/68663; WO 99/43691; WO 02/18404 and WO2006/021341, and U.S. Patent Application Publication US 2005/0038240, including 4'-azido nucleosides such as R1626, 4'-azidocytidine; U.S. Patent Application Publications US 2002/0019363, US 2003/0236216, US 2004/0006007 and US 2004/0063658; and International Patent Application Publications WO 02/100415, WO 03/026589, WO 03/026675, WO 03/093290, WO 04/011478, WO 04/013300 and WO 04/028481; the content of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in International Patent Application Publications WO 02/057287, WO 02/057425, WO 03/068244, WO 2004/000858, WO 04/003138 and WO 2004/007512; U.S. Pat. No. 6,777,392 and U.S. Patent Application Publication US2004/0067901; the content of each is incorporated herein by reference in its entirety. Other such HCV polymerase inhibitors include, but are not limited to, valopicitabine (NM-283; Idenix) and 2'-F-2'-beta-methylcytidine (see also WO 2005/003147).

In one embodiment, nucleoside HCV NS5B polymerase inhibitors that are used in combination with the present HCV NS3 protease inhibitors are selected from the following compounds: 4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-C,2-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C, 2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof.

The compounds of the present invention may also be combined for the treatment of HCV infection with non-nucleoside inhibitors of HCV polymerase such as those disclosed in International Patent Application Publications WO 01/77091; WO 01/47883; WO 02/04425; WO 02/06246; WO 02/20497; WO 2005/016927 (in particular JTK003); the content of each is incorporated herein by reference in its entirety; and HCV-796 (Viropharma Inc.).

In one embodiment, non-nucleoside HCV NS5B polymerase inhibitors that are used in combination with the present HCV NS3 protease inhibitors are selected from the following compounds: 14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5]benzoxazocin-7-yl)-N,N-dimethylethane-1,2-diaminium bis(trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-a][2,5]benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5]benzodiazocine-11-carboxylic acid; 14-cyclohexyl-6-[2-(diethylamino)ethyl]-7-oxo-5,6,7,8-tetrahydroindolo[2,1-a][2,5]benzodiazocine-11-carboxylic acid; 14-cyclohexyl-6-(1-methylpiperidin-4-yl)-7-oxo-5,6,7,8-tetrahydroindolo[2,1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',2':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof.

The HCV NS3 protease inhibitory activity of the present compounds may be tested using assays known in the art. One such assay is HCV NS3 protease time-resolved fluorescence (TRF) assay as described below and in International Patent Application Publication WO 2006/102087. Other examples of such assays are described in e.g., International Patent Application Publication WO 2005/046712.

A NS3 protease assay can be performed, for example, in a final volume of 100 µl assay buffer containing 50 mM HEPES, pH 7.5, 150 mM NaCl, 15% glycerol, 0.15% TRITON X-100, 10 mM DTT, and 0.1% PEG 8000. NS3 and NS4A protease is pre-incubated with various concentrations of inhibitors in DMSO for 30 minutes. The reaction is initiated by adding the TRF peptide substrate (final concentration 100 nM). NS3 mediated hydrolysis of the substrate is quenched after 1 hour at room temperature with 100 µl of 500 mM MES, pH 5.5. Product fluorescence is detected using either a VICTOR V2 or FUSION fluorophotometer (Perkin Elmer Life and Analytical Sciences) with excitation at 340 nm and emission at 615 nm with a 400 µs delay. Testing concentrations of different enzyme forms are selected to result in a signal to background ratio (S/B) of 10-30. $IC_{50}$ values are derived using a standard four-parameter fit to the data. $K_i$ values are derived from $IC_{50}$ values using the following formula, $$IC_{50} = K_i(1 + [S]/K_M),  \quad \text{Eqn (1)},$$

where [S] is the concentration of substrate peptide in the reaction and $K_M$ is the Michaelis constant. See P. Gallinari et al., 38 BIOCHEM. 5620-32 (1999); P. Gallinari et al., 72 J. VIROL. 6758-69 (1998); M. Taliani et al., 240 ANAL. BIOCHEM. 60-67 (1996).

The present invention also includes processes for making compounds of formula (I). The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice.

Olefin metathesis catalysts include the following Ruthenium based species: F. Miller et al., 118 J. AM. CHEM. SOC. 9606 (1996); G. Kingsbury et al., 121 *J. Am. Chem. Soc.* 791 (1999); H. Scholl et al., 1 ORG. LETT. 953 (1999); U.S. Patent Application Publication US2002/0107138; K. Furstner et al., 64 J. ORG. CHEM. 8275 (1999). The utility of these catalysts in ring closing metathesis is well known in the literature (e.g. Trnka and Grubbs, 34 ACC. CHEM. RES. 18 (2001).

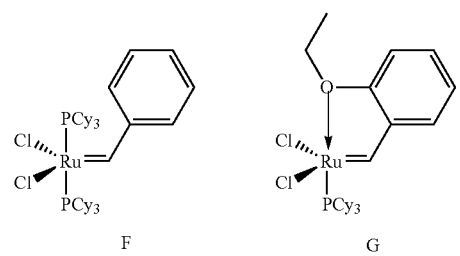

F          G

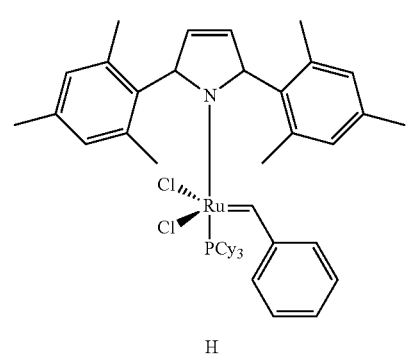

H

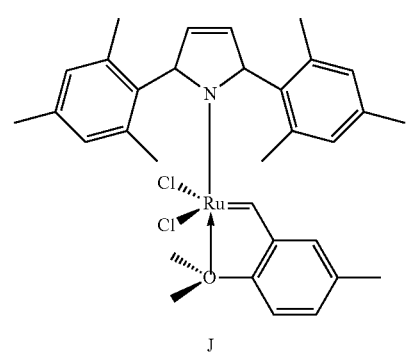

J (Zhan catalyst 1A, Zannan Pharma Ltd.)

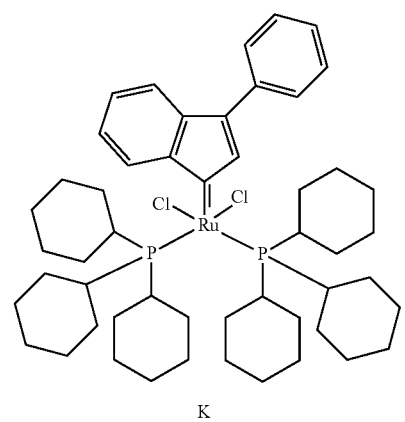

K

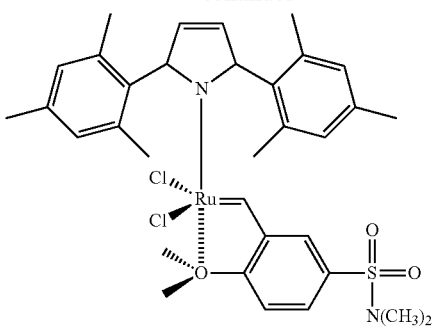

Zhan ruthenium metathesis catalyst RC-303
(Zhan catalyst 1B, RC-303,
Zannan Pharma Ltd.)

The following examples serve only to illustrate the invention and its practice. The examples are not to be construed as limitations on the scope or spirit of the invention.

| List of Abbreviations | |
|---|---|
| BOC (also Boc) | t-Butyloxycarbonyl |
| B(OMe)$_3$ | Trimethyl borate |
| BOP | Benzotriazole-1-yl-oxy-tris-(dimethylamino)-phosphonium hexafluorophosphate |
| Brosyl chloride | 4-Bromophenyl sulfonylchloride |
| tBuOH | t-Butanol |
| BuLi | Butyl lithium |
| CAN | Ceric ammonium nitrate |
| CDCl$_3$ | Deuterio-trichloromethane |
| CDI | N,N'-Carbonyl diimidazole |
| CH$_3$CN | Acetonitrile |
| mCPBA | m-Chloroperbenzoic acid |
| Cs$_2$CO$_3$ | Cesium carbonate |
| CuI | Copper iodide |
| Cu(I)Br•SMe$_2$ | Copper (I) bromide dimethyl sulfide complex |
| DABCO | 1,4-diazabicyclo[2.2.2]octane |
| DBA (also dba) | Dibenzylidene acetone |
| DBU | 1,8-Diazabicyclo[5.4.0]undec-7-ene |
| DCC | Dicyclohexylcarbodiimide |
| DCE | Dichloroethane |
| DCM | Dichloromethane |
| DEAD | Diethyl azodicarboxylate |
| DIAD | Diisopropyl azodicarboxylate |
| DIEA | Diethylamine |
| DIPA | Diethylpropylamine |
| DIPEA | Diisopropylethylamine |
| DMAP | 4-Dimethylamino pyridine |
| DMF | Dimethylformamide |
| DMSO | Dimethyl Sulfoxide |
| DPPF (also dppf) | 1,1'-bid(Diphenylphosphino)ferrocene |
| EDC | N-(3-Dimethylaminopropyl)-N'-ethylcarbodiimide |
| ESI | Electrospray ionization |
| Et$_2$O | Diethyl ether |
| EtOAc | Ethyl Acetate |
| EtOH | Ethanol |
| H$_2$ | Hydrogen or hydrogen atomosphere |
| HATU | O-(7-Azabenzotriazol-1-yl)-N,N,N',N'-tetramethyluronium hexafluorophosphate |
| HBr | Hydrobromic acid |
| HCl | Hydrochloric acid |
| HMPA | Hexamethylphosphoramide |
| HOAc | Acetic acid |
| HOAt | 1-Hydroxy-7-azabenzotriazole |
| HOBT | 1-Hydroxy benzotriazole |
| H$_2$O | Water |
| H$_2$O$_2$ | Hydrogen peroxide |

| List of Abbreviations | |
|---|---|
| HPLC | High performance liquid chromatography |
| I$_2$ | Iodine |
| KHSO$_4$ | Potassium bisulfate |
| K$_2$SO$_4$ | Potassium sulfate |
| K$_2$CO$_3$ | Potassium carbonate |
| KOH | Potassium hydroxide |
| LAH | Lithium aluminium hydride |
| LCMS | High performance liquid chromatography - mass spectrometry |
| LiOH | Lithium hydroxide |
| LiOH•H$_2$O | Lithium hydroxide monohydrate |
| LRMS | Low resolution mass spectrometry |
| Me$_3$Al | Trimethylaluminium |
| MeLi | Methyllithium |
| MeOH | Methanol |
| MgSO$_4$ | Magnesium Sulfate |
| MsCl | Mesyl chloride |
| N$_2$ | Nitrogen or nitrogen atomosphere |
| NH$_4$Cl | Ammonium chloride |
| NH$_4$OH | Ammonium hydroxide |
| Nle | Norleucine |
| NMP | N-Methyl pyrrolidinone |
| NaH | Sodium hydride |
| NaHCO$_3$ | Sodium hydrogen carbonate (sodium bicarbonate) |
| NaHSO$_3$ | Sodium bisulfite |
| NaOH | Sodium hydroxide |
| NaOMe | Sodium methoxide |
| Na$_2$SO$_3$ | Sodium sulfite |
| Na$_2$S$_2$O$_3$ | Sodium thiosulfate |
| Na$_2$SO$_4$ | Sodium sulfate (anhydrous) |
| PCy$_3$ | Tricyclohexyl phosphine |
| POBr | Phosphoryl bromide |
| POBr$_3$ | Phosphoryl tribromide |
| P$_2$O$_5$ | phosphorus pentoxide (P$_4$O$_{10}$) |
| Pd/C | Palladium on carbon |
| PhMe | Toluene |
| PPh$_3$ | Triphenylphosphine |
| RT | Room temperature, approximately 25 C. |
| Ru/C | Ruthenium on carbon |
| SiO$_2$ | Silica or silica gel |
| TBAF | Tetrabutylammonium fluoride |
| TBTU | O-Benzotriazol-1-yl-N,N,N',N'-tetramethyluronium tetrafluoroborate |
| TEA | Triethylamine |
| TFA | Trifluoroacetic acid |
| THF | Tetrahydofuran |
| TIPSOTf | Triisopropylsilyl triflate |
| TMSCl | Chlorotrimethyl silane |
| TsCl | p-Toluenesulfonyl chloride |
| Zn(CN)$_2$ | Zinc cyanide |

Synthesis of Intermediates

Intermediates A

| Intermediate # | Structure | Name | Literature Reference |
|---|---|---|---|
| A1 | 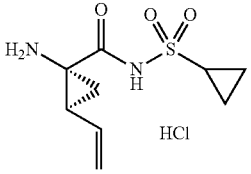 | (1R,2S)-1-Amino-N-(cyclopropylsulfonyl)-2-vinylcyclopropanecarboxamide hydrochloride | U.S. Pat. No. 6,995,174 |
| A2 | 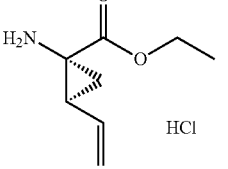 | Ethyl (1R,2S)-1-amino-2-vinylcyclopropanecarboxylate hydrochloride | U.S. Pat. No. 6,323,180 |
| A13 | 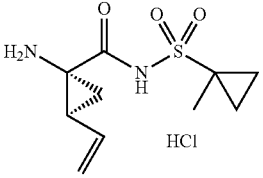 [SMILES: C=C[C@@H]1C[C@]1(N)C(=O)NS(=O)(=O)C1(C)CC1 ; Cl] | (1R,2S)-1-({[(1-Methylcyclopropyl)sulfonyl]amino}carbonyl)-2-vinylcyclopropanaminium chloride | U.S. Pat. No. 7,135,462 |

Intermediate A3: (1R,2R)-1-Amino-N-(cyclopropylsulfonyl)-2-ethylcyclopropanecarboxamide hydrochloride

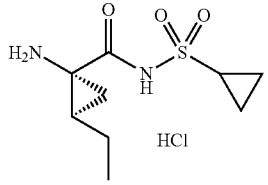

Step 1: t-Butyl ((1R,2R)-1-{[(cyclopropylsulfonyl)amino]carbonyl}-2-ethylcyclopropyl)carbamate

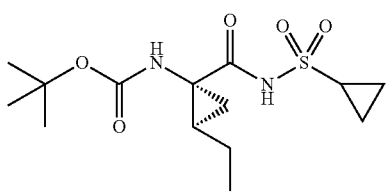 [SMILES: CC[C@@H]1C[C@]1(NC(=O)OC(C)(C)C)C(=O)NS(=O)(=O)C1CC1]

A hydrogenation vessel was charged with a MeOH (1000 mL) slurry of t-butyl ((1R,2S)-1-{[(cyclopropylsulfonyl)amino]carbonyl}-2-vinylcyclopropyl)carbamate (164 g, 0.50 mol) (U.S. Pat. No. 6,995,174) and 5% Ru/C (dry, 7.5 wt %, 12.4 g) and stirred. The vessel was placed under $N_2$ (20 psi) and vented to atmospheric pressure (3×) to remove residual oxygen. The vessel was then placed under $H_2$ (50 psi). After 20 hours, the vessel was vented to atmospheric pressure. The reaction slurry was then transferred out of the reaction vessel and filtered through SOLKA FLOK (34 g, wetted with 100 mL MeOH) to yield a clear, light brown solution. The SOLKA FLOK was rinsed with MeOH (200 mL×2). The combined MeOH solutions were concentrated under reduced pressure to yield crude product as a white solid (153 g). The crude product was slurried in EtOAc (800 mL), warmed to 40° C. and aged 30 minutes. The solution was then seeded, aged 30 minutes, and heptane (500 mL) was added via addition funnel over 30 minutes. The partially crystallized solid was cooled to RT and aged overnight, after which additional heptane (500 mL) was added. After 1 hour, additional heptane (250 mL) was added via addition funnel, and the white slurry aged for 1 hour. The solution was filtered, and the solid was rinsed with heptane/EtOAc (500 mL, 4:1) and dried under reduced pressure to give t-butyl ((1R,2R)-1-{[(cyclopropylsulfonyl)amino]carbonyl}-2-ethylcyclopropyl)carbamate (125.9 g).

Step 2: (1R,2R)-1-Amino-N-(cyclopropylsulfonyl)-2-ethylcyclopropanecarboxamide hydrochloride (Intermediate A3)

A solution of the product from Step 1 (92 g, 0.28 mol) in DCM (1200 mL) was cooled to 0° C., and HCl was bubbled through the solution for 10 minutes. The cooling bath was then removed, and the reaction mixture stirred for 2 hours. $N_2$ was bubbled through the reaction mixture for 5 minutes, and the volatiles evaporated. The residue was azeotroped with DCM (3×) to give an off-white powder (75 g). LRMS (M+H)+ Calcd.=233. found 233.

Intermediate A4: Trans-4-pent-4-en-1-yltetrahydrofuran-3-ol

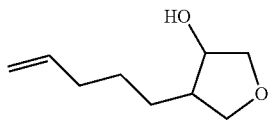

To a mixture of CuI (1.66 g, 8.71 mmol) in THF (100 mL) at −5° C., a 0.5M solution of bromo(pent-4-en-1-yl)magnesium (116 mL, 5.81 mmol) was added. The solution was stirred for 1 hour and cooled to −20° C. 3,6-Dioxabicyclo [3.1.0]hexane (5.0 g, 58.1 mmol) was added dropwise, and the reaction mixture was slowly warmed to RT and stirred for 15 hours. The reaction mixture was quenched with NH$_4$Cl$_{(aq.)}$ and extracted with Et$_2$O (3×). The combined organics were washed with H$_2$O and brine, dried over Na$_2$SO$_4$, filtered and concentrated. The crude product was purified on SO$_2$ (gradient elution, 10-100% EtOAc/hexanes). $^1$H NMR (500 MHz, CDCl$_3$) δ 5.83-5.75 (m, 1H); 5.04-4.95 (m, 2H); 4.14-4.07 (m, 3H); 3.85 (m, 1H); 3.70 (m, 1H); 3.44 (m, 1H); 2.07 (m, 3H); 1.45 (m, 3H) ppm.

Intermediate A5: Trans-2-pent-4-en-1 ylcyclopentanol

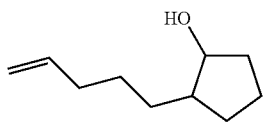

A solution of 5-bromopent-1-ene (11.81 mL, 100 mmol) in Et$_2$O (100 mL) was added to magnesium (2.43 g, 100 mmol) over 20 minutes. The resulting suspension was heated under reflux for 40 minutes, then cooled to 20° C., taken up in a syringe, and added dropwise at −5° C. to a stirred suspension of CuI (3.17 g, 16.6 mmol) in THF (160 mL). The resulting solution was stirred for 30 minutes at −5° C., then cooled to −20° C. Cyclopentene oxide (7.21 mL, 83 mmol) was added dropwise, and the resulting mixture was warmed to 20° C. over 2 hours, then stirred for 48 hours. The reaction was quenched by addition of NH$_4$Cl$_{(aq.)}$; then the layers were separated, and the aqueous layer was extracted with Et$_2$O. The combined organic phases were washed with H$_2$O and brine, then dried over Na$_2$SO$_4$. Filtration and removal of the volatiles gave a residue that was purified by column chromatography on SiO$_2$ (gradient elution, 1-100% EtOAc/petroleum ether) to afford the title compound (7.92 g, 62%) as a liquid. $^1$H NMR (400 MHz, CDCl$_3$) δ 5.88-5.76 (m, 1H), 5.01 (d, J=17.2 Hz, 1H), 4.95 (d, J=10.6 Hz, 1H), 3.83 (br s, 1H), 2.12-2.00 (m, 2H), 1.99-1.84 (m, 2H), 1.76-1.30 (m, 7H), 1.24-1.11 (m, 2H).

Intermediate A6: Trans-2-but-3-en-1ylcyclopentanol

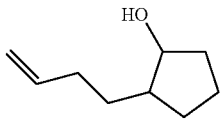

The title compound was prepared in a similar manner to Intermediate A5, using but-3-enylmagnesium bromide.

Intermediate A7: Trans-2-allyl-1ylcyclopentanol

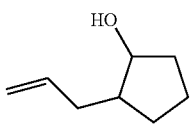

The title compound was prepared in a similar manner to Intermediate A5, using allylmagnesium bromide.

Intermediate A8: (1R,2R)-2-pent-4-en-1-ylcyclopentyl acetate

AMANO LIPASE PS (7.0 g, 64.7 mmol) was added to a solution of trans-2-pent-4-en-1-ylcyclopentanol (10.0 g, 64.7 mmol) and vinyl acetate (19.5 g, 129.4 mmol) in Et$_2$O (275 mL). The mixture was stirred for 16 hours, then filtered through CELITE. The filtrate was concentrated to afford a residue that was purified by column chromatography on SiO$_2$ (gradient elution, 0-100% Et$_2$O/petroleum ether) to afford in the first fractions the title compound (5.43 g, 43%). $^1$H NMR (300 MHz, CDCl$_3$) δ 5.89-5.72 (m, 1H), 5.00 (d, J=18.1 Hz, 1H), 495 (d, J=11.0 Hz, 1H), 4.82-4.73 (m, 1H), 2.11-1.98 (m, 2H), 2.03 (s, 3H), 1.98-1.85 (m, 3H), 1.71-1.60 (m, 3H), 1.50-1.35 (m, 3H), 1.29-1.14 (m, 2H); [α]$_D$=−36.1 (c=0.73 in CHCl$_3$). The later fractions contained enantio-enriched (1S,2S)-2-pent-4-en-1-ylcyclopentanol.

Intermediate A9:
(1R,2R)-2-pent-4-en-1-ylcyclopentanol

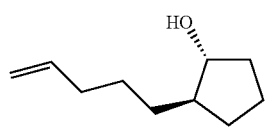

A stirred solution of (1R,2R)-2-pent-4-en-1-ylcyclopentyl acetate (3.79 g, 19.3 mmol) in MeOH (320 ml) was treated with methanolic NaOMe (25%, 8.1 ml, 35.4 mmol) and stirred for 15 hours at 20° C. DOWEX 50WX8-100 ion-exchange resin (washed with MeOH) was added portionwise until the pH was neutral, then the mixture was filtered through CELITE. The filtrate was concentrated in vacuo, and the residue was partitioned between EtOAc and H$_2$O. The organic layer was separated, washed with brine, and dried over Na$_2$SO$_4$. Filtration and removal of the volatiles afforded the title compound (2.61 g, 88%) as a liquid that was used directly in the subsequent reactions. [α]D −37.3 (c=0.65, CHCl$_3$).

Intermediate A10 (1R,2R)-2-but-3-en-1-ylcyclopentanol

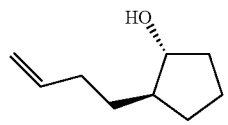

The title compound was prepared from Intermediate A6 using the method described for the preparation of Intermediate A9.

Intermediate A11: (1R,2R)-2-allyl-1-ylcyclopentanol

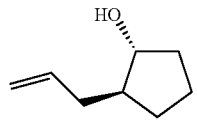

The title compound was prepared from Intermediate A7 using the method described for the preparation of Intermediate A9.

Intermediate A12: 2-but-3-en-1-ylcyclopropanol

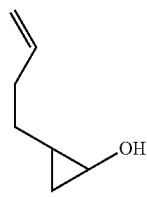

A solution of 1.0 M hexenylmagnesium bromide (113 ml, 113 mmol) was added slowly to a mixture of methyl formate (3.53 ml, 56.5 mmol) and chlorotitanium trisisopropoxide (56.5 ml, 56.5 mmol) in THF (210 mL) at −78° C. The reaction was allowed to stir at −78° C. for 10 min and then allowed to warm to −40° C. and age 2 hrs. The reaction was allowed to warm to room temperature and then warmed to 40° C. for 1 hr. The reaction was quenched into ice cold 10% sulfuric acid (500 mL). The product was extracted with diethyl ether (3×100 mL) washed with saturated NaHCO$_{3(aq.)}$, brine, dried over magnesium sulfate, filtered and concentrated to give ~15 gm oil. The oil was chromatographed on silica using 5-15% ethyl acetate/hexane to afford the title compound (1.0 g, 8%) as an oil. $^1$H NMR (400 MHz, CDCl$_3$) δ 5.80 (m, 1H), 5.02 (d, J=17.2 Hz, 1H), 4.95 (d, J=10.6 Hz, 1H), 3.21 (m, 1H), 2.20-2.00 (m, 2H), 1.88 (s, 1H), 1.45-1.15 (m, 4H), 0.92 (m, 1H), 0.70 (m, 1H), 0.36 (m, 1H).

Intermediates B

Intermediate B1: (2S)-Cyclopentyl[({[(1R,2R)-2-pent-4-en-1-ylcyclopentyl]oxy}carbonyl)amino]acetic acid

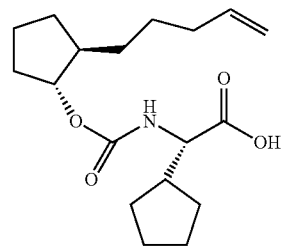 [SMILES: C=CCCC[C@@H]1CCC[C@H]1OC(=O)N[C@H](C(=O)O)C1CCCC1]

Step 1: Methyl (2S)-cyclopentyl(isocyanato)acetate

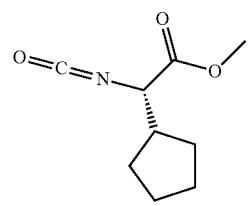

A suspension of methyl (2S)-amino(cyclopentyl)acetate hydrochloride (3.21 g, 16.57 mmol) in DCM (69 mL) and saturated NaHCO$_{3(aq.)}$ (132 mL) was cooled to 0° C. and treated with triphosgene (2.21 g, 7.46 mmol). The mixture was stirred at 0° C. for 3 hours, then warmed to 20° C. and diluted with DCM. The layers were separated, and the aqueous phase was re-extracted with DCM. The combined organic phases were washed with brine and dried over Na$_2$SO$_4$. Filtration and removal of the volatiles afforded the title compound (2.95 g, 97%) as an oily solid that was used directly in subsequent steps. $^1$H NMR (400 MHz, DMSO-d$_6$) δ 4.36 (d, J=4.8 Hz, 1H), 3.73 (s, 1H), 2.35-2.24 (m, 1H), 1.76-1.24 (m, 8H).

Step 2: Methy (2S)-cyclopentyl[({[(1R,2R)-2-pent-4-en-1-ylcyclopentyl]oxy}carbonyl) amino]acetate

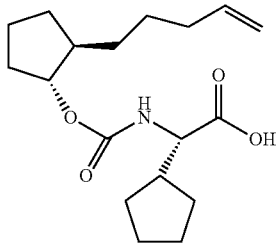 [SMILES: C=CCCC[C@@H]1CCC[C@H]1OC(=O)N[C@H](C(=O)O)C1CCCC1]

A solution of methyl (2S)-cyclopentyl(isocyanato)acetate (1.57 g, 8.56 mmol) and (1R,2R)-2-pent-4-en-1-ylcyclopentanol (Intermediate A9) (1.20 g, 7.78 mmol) in PhMe (56 mL) was treated portionwise with DMAP (0.95 g, 7.78 mmol). The resulting mixture was stirred for 5 hours at 85° C., then cooled to 20° C., and diluted with EtOAc and HCl$_{(aq.)}$ (1N). The organic layer was separated, washed with brine, and dried over Na$_2$SO$_4$. Filtration and removal of the volatiles gave a residue that was purified by column chromatography (gradient elution, 4-40% Et$_2$O/petroleum ether) to afford the title compound (1.97 g, 76%) as an oil. LCMS (ES+) m/z, 338 (M+H)$^+$.

Step 3: (25)-Cyclopentyl[({[(1R,2R)-2-pent-4-en-1-ylcyclopentyl]oxy}carbonyl)amino]acetic acid A mixture of methyl (2S)-cyclopentyl[({[(1R,2R)-2-pent-4-en-1-ylcyclopentyl]oxy}carbonyl)amino]acetate (1.97 g, 5.84 mmol) and LiOH.H$_2$O (0.74 g, 17.51 mmol) in a 1:1 mixture of THF:H$_2$O (60 mL) was heated to 40° C. The solution was stirred for 4 hours, then cooled to 20° C. The THF was removed under reduced pressure, and the residual aqueous solution was extracted with EtOAc. The organic phase was washed with H$_2$O and brine, then dried over Na$_2$SO$_4$. Filtration and removal of the volatiles afforded the title compound (1.85 g, 98%) as an oil that was used directly in subsequent steps. $^1$H NMR (400 MHz, DMSO-d$_6$) δ 12.25 (br s, 1H), 7.28 (d, J=8.1 Hz, 1H), 5.84-5.71 (m, 1H), 4.98 (d, J=17.4 Hz, 1H), 4.92 (d, J=10.1 Hz, 1H), 4.60-4.52 (m, 1H), 3.78 (t, J=8.0 Hz, 1H), 2.18-2.05 (m, 1H), 2.04-1.94 (m, 3H), 1.91-1.74 (m, 3H), 1.70-1.06 (m, 15H).

Intermediate B2: (2S)-[({[(1R,2S)-2-allylcyclopentyl]oxy}carbonyl)amino](cyclohexyl)acetic acid

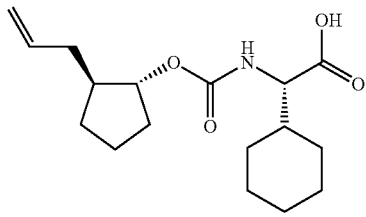 [SMILES: C=CC[C@@H]1CCC[C@H]1OC(=O)N[C@H](C(=O)O)C1CCCCC1]

Step 1: Methyl (2S)-[({[(1R,2S)-2-allylcyclopentyl]oxy}carbonyl)amino](cyclohexyl)acetate

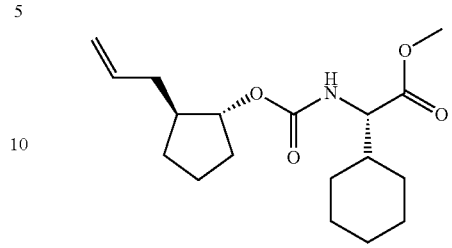

N,N'-disuccinimidyl carbonate (8.28 g, 32.3 mmol) and triethylamine (4.51 ml, 32.3 mmol) were added to a solution of Intermediate A11 (3.4 g, 26.9 mmol) in acetonitrile (70 ml) and left stir under a N$_2$ atmosphere for 6 hours. Methyl (2S)-amino(cyclohexyl)acetate hydrochloride (8.39 g, 40.4 mmol) and triethylamine (7.51 ml, 53.9 mmol) were added to the reaction mixture and left stir under a N$_2$ atmosphere for 12 hours. Reaction was concentrated in vacuo, diluted with EtOAc, and washed organics with 1N HCl, brine, sat'd NaHCO$_3$, and brine. The organics were dried over Na$_2$SO$_4$, filtered, and removal of the volatiles under reduced pressure gave a residue that was purified by column chromatography (gradient elution, 10-30% EtOAc/Hexane) to afford the title compound (5.2 g, 60%) as an oil. LCMS (ES+) m/z 324.08 (M+H)$^+$.

Step 2: (2S)-[({[(1R,2S)-2-allylcyclopentyl]oxy}carbonyl)amino](cyclohexyl)acetic acid LiOH.H$_2$O (2.02 g, 48.2 mmol) was added to a solution of the product from Intermediate B2, Step 1 (5.2 g, 16.1 mmol) in a 2:1:1 mixture of THF:MeOH:H$_2$O (100 mL) and stirred for 12 hours. The organics were removed under reduced pressure; the residual aqueous solution was acidified with dilute HCl and extracted with EtOAc. The organic phase was washed with brine and dried over Na$_2$SO$_4$. Filtration and removal of the volatiles afforded the title compound (4.9 g, 100%) as an oil that was used directly in subsequent steps. $^1$H NMR (400 MHz, CDCl$_3$): δ 5.77 (ddt, J=17.0, 10.2, 6.8 Hz, 1H); 5.08 (d, J=8.8 Hz, 1H); 5.07-4.91 (m, 2H); 4.75 (s, 1H); 4.30 (dd, J=9.0, 4.9 Hz, 1H); 2.27-2.19 (m, 1H); 2.05-1.71 (m, 10H); 1.81-1.48 (m, 6H); 1.36-1.04 (m, 8H).

Intermediate B3: Methyl (2S)-[({[(1R,2S)-2-allylcyclopentyl]oxy}carbonyl)amino](cyclopentyl)acetate

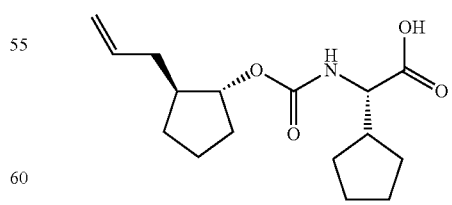

The title compound was prepared from methyl (2S)-amino(cyclopentyl)acetate hydrochloride and Intermediate A11 using the method described for the preparation of Intermediate B2. NMR (400 MHz, CDCl$_3$): δ 5.85-5.71 (m, 1H); 5.08 (d, J=8.7 Hz, 1H); 5.07-4.93 (m, 2H); 4.75 (s, 1H); 4.35-4.27

(m, 1H); 2.31-2.19 (m, 2H); 2.10-1.75 (m, 4H); 1.93-1.59 (m, 2H); 1.92-1.33 (m, 8H); 1.49-1.22 (m, 3H).

Intermediate B4: Methyl N-({[(1R,2S)-2-allylcyclopentyl]oxy}carbonyl)-3-methyl-L-valinate

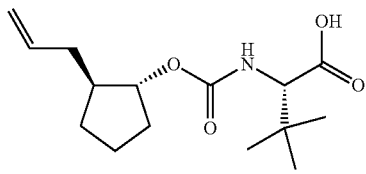 [SMILES: C=CC[C@@H]1CCC[C@H]1OC(=O)N[C@H](C(=O)O)C(C)(C)C]

The title compound was prepared from methyl 3-methyl-L-valinate hydrochloride and Intermediate A11 using the method described for the preparation of Intermediate B2. $^1$H NMR (400 MHz, CDCl$_3$): δ 5.83-5.71 (m, 1H); 5.17 (d, J=9.7 Hz, 1H); 5.04 (s, 1H); 5.03-4.91 (m, 1H); 4.74 (s, 1H); 4.19 (d, J=9.5 Hz, 1H); 2.32-2.14 (m, 1H); 2.02-1.82 (m, 4H); 1.68-1.61 (m, 3H); 1.35-1.13 (m, 2H); 1.03 (s, 9H).

Intermediate B5: N-{[(2-but-3-en-1-ylcyclopentyl)oxy]carbonyl}-3-methyl-L-valine

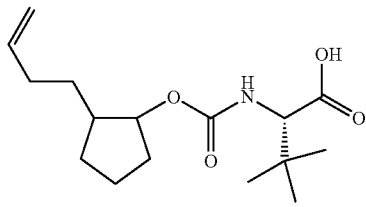 [SMILES: C=CCCC1CCCC1OC(=O)N[C@H](C(=O)O)C(C)(C)C]

The title compound was prepared from methyl 3-methyl-L-valinate hydrochloride and Intermediate A6 using the method described for the preparation of Intermediate B2. $^1$H NMR (400 MHz, CDCl$_3$) δ 5.80 (m, 1H), 5.17 (d, J=8.9 Hz, 1H), 5.00 (d, J=17.1 Hz, 1H), 4.94 (d, J=10.6 Hz, 1H), 4.72 (brs, 1H), 4.19 (d, J=8.9 Hz, 1H), 2.08 (m, 2H), 1.92 (m, 3H), 1.64 (m, 4H), 1.38-1.12 (m, 2H), 1.02 (s, 9H).

Intermediate B6: (2S)-({[(2-but-3-en-1-ylcyclopropyl)oxy]carbonyl}amino)(cyclopentyl)acetic acid

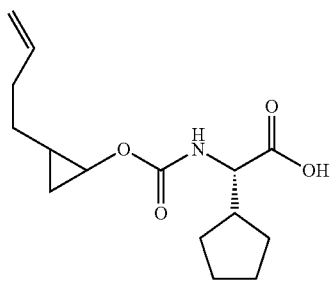 [SMILES: C=CCCC1CC1OC(=O)N[C@H](C(=O)O)C1CCCC1]

The title compound was prepared from methyl (2S)-amino(cyclopentyl)acetate hydrochloride and Intermediate A12 using the method described for the preparation of Intermediate B1. $^1$H NMR (400 MHz, CDCl$_3$) δ 5.82 (m, 1H), 5.20 (m, 1H), 5.02 (d, J=17.1 Hz, 1H), 4.95 (d, J=10.6 Hz, 1H), 4.40-3.60 (m, 4H), 2.40-1.50 (m, 8H), 1.50-1.20 (m, 4H), 1.02 (m, 1H), 0.82 (m, 1H), 0.51 (m, 1H).

Intermediate B7: (2S)-[({[(1R,2S)-2-but-3-en-1-ylcyclopentyl]oxy}carbonyl)amino](cyclopentyl)acetic acid

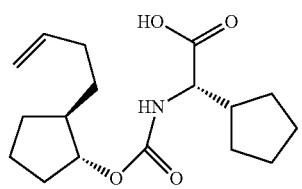 [SMILES: C=CCC[C@@H]1CCC[C@H]1OC(=O)N[C@H](C(=O)O)C1CCCC1]

The title compound was prepared from methyl (2S)-amino(cyclopentyl)acetate hydrochloride and Intermediate A10 using the method described for the preparation of Intermediate B1. LCMS (ES+) m/z 310.0 (M+H)+.

Intermediates C

Intermediate C1: 2-But-3-en-1-ylisoquinoline-1,3(2H,4H)-dione

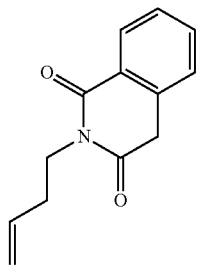 [SMILES: C=CCCN1C(=O)Cc2ccccc2C1=O]

Homophthalic anhydride (1.5 g, 9.25 mmol), 3-buten-1-amine (1.129 ml, 11.10 mmol), and 4 A molecular sieves (300 mg) were combined in toluene (15 ml) and heated to 160° C. in a microwave for 40 minutes. The reaction mixture was diluted with CH$_2$Cl$_2$ and the slurry was filtered over CELITE. The filtrate was concentrated in vacuo and the resulting residue was purified by column chromatography (gradient elution, 10-20% EtOAc/Hexane) to afford the title compound (0.75 g, 36%) as an oil. LCMS (ES+) m/z 216.03 (M+H)+.

Intermediate C2: 2-But-3-en-1-yl-6-methoxyisoquinoline-1,3(2H,4H)-dione

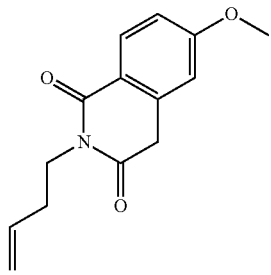 [SMILES: C=CCCN1C(=O)Cc2cc(OC)ccc2C1=O]

Step 1: 2-(Carboxymethyl)-4-methoxybenzoic acid

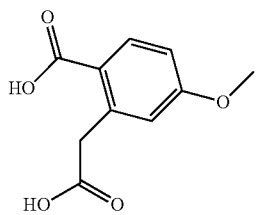

A solution of diisopropylamine (3.43 ml, 24.07 mmol) in THF (3 mL) was cooled to −78° C. and n-butyllithium (9.63 ml, 24.07 mmol) was added dropwise and allowed the solution to warm to 0° C. for 5 min and then re-cooled to −78° C. 4-methoxy-2-methylbenzoic acid (1 g, 6.02 mmol) and dimethyl carbonate (1.013 ml, 12.04 mmol) in THF (3 mL) was added dropwise. After the addition is complete, the reaction is allowed to slowly warm to RT and stir for 4 h. The reaction was quenched with 10 mL of $H_2O$ and allowed to stir for 16 h. The layers were separated, washed the organics with $H_2O$ (2×), combined all the aqueous extractions and adjusted the pH to 2-3 with 6N HCl while in an ice bath. The resulting in a white precipitate was filtered and dried under vacuum to afford the title compound (1.09 g, 86%) as a white solid. LCMS (ES+) m/z 211.05 (M+H)$^+$.

Step 2: 2-But-3-en-1-yl-6-methoxyisoquinoline-1,3(2H,4H)-dione

The title compound was prepared according to the procedure for Intermediate C1, using 2-(carboxymethyl)-4-methoxybenzoic acid in place of homophthalic anhydride. LCMS (ES+) m/z 246.04 (M+H)$^+$.

Intermediate C3: 2-but-3-en-1-yl-6-chloroisoquinoline-1,3(2H,4H)-dione

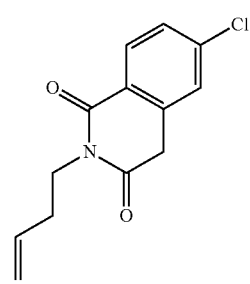 [SMILES: C=CCCN1C(=O)Cc2cc(Cl)ccc2C1=O]

The title compound was prepared according to the procedure for Intermediate C2, using 2-(carboxymethyl)-4-chlorobenzoic acid. LCMS (ES+) m/z 250.01 (M+H)$^+$.

Intermediate C4: 2-but-3-en-1-yl-7-fluoroisoquinoline-1,3(2H,4H)-dione

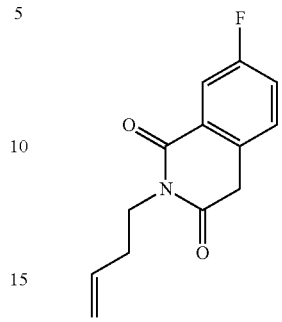

The title compound was prepared according to the procedure for Intermediate C2, using 2-(carboxymethyl)-5-fluorobenzoic acid. LCMS (ES+) m/z 234.08 (M+H)$^+$.

Intermediate C5: 2-allylisoquinoline-1,3(2H,4H)-dione

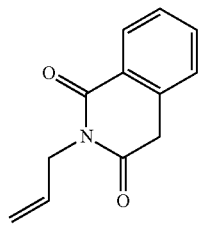

The title compound was prepared according to the procedure for Intermediate C1, using prop-2-en-1-amine in place of 3-buten-1-amine. LCMS (ES+) m/z 202.04 (M+H)$^+$.

Intermediates D

Intermediate D1: 3-allylquinazoline-2,4(1H,3H)-dione

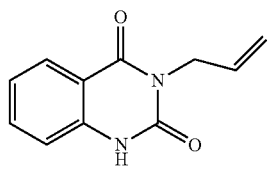

The title compound was prepared according to Chern, Ji-Wang, J. Heterocyclic Chem., 27, 1467 (1990).

Intermediate D2:
3-Allyl-7-bromoquinazoline-2,4(1H,3H)-dione

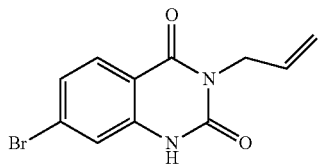 [SMILES: C=CCn1c(=O)[nH]c2cc(Br)ccc2c1=O]

Step 1: 4-Bromo-2-[(ethoxycarbonyl)amino]benzoic acid

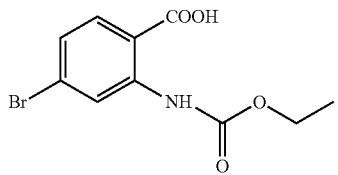 [SMILES: CCOC(=O)Nc1cc(Br)ccc1C(=O)O]

Ethyl chloroformate (5.00 ml, 52.1 mmol) was added to a solution of 2-amino-4-bromobenzoic acid (3.75 g, 17.36 mmol) in THF (70 ml) at room temperature. The mixture was heated to 70° C. and let stir for 24 hrs. The reaction was concentrated to give an oily solid. The resulting solid was diluted with toluene (50 mL), concentrated and then triturated with 5% ether/hexanes (100 mL) to give upon filtration and subsequent washing of the solid with hexane the title compound (4.6 gm, 92%) as a solid. LCMS (ES$^+$) m/z 287.88 (M+H)$^+$.

Step 2:
3-Allyl-7-bromoquinazoline-2,4(1H,3H)-dione

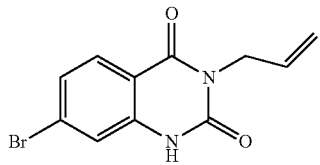 [SMILES: C=CCn1c(=O)[nH]c2cc(Cl)ccc2c1=O]

BOP (8.47 g, 19.16 mmol) was added to a solution of 4-bromo-2-[(ethoxycarbonyl)amino]benzoic acid (4.6 g, 15.97 mmol), N-methylmorpholine (3.51 ml, 31.9 mmol) and allylamine (1.434 ml, 19.16 mmol) in DMF (50 ml) at room temperature. The mixture was allowed to stir at room temperature for 4 hrs. DBU (24.07 ml, 160 mmol) was added to the reaction and the temperature was raised to 60° C. The mixture let was allowed to stir at 60° C. for 1 hr. The mixture was quenched into 0.5 N HCL (200 mL), and the pH was adjusted to 1.5 with 3N HCL. Thick white solids were observed. The reaction was diluted to ~400 mL with water let stir 10 min and solids filtered. The solids were washed with 0.5 N HCL (50 mL) and then slurry washed with water and sucked dry overnight to give the title compound (4.5 gm, 100%) as a solid. LCMS (ES$^+$) m/z 280.87 (M+H)$^+$.

Intermediate D3:
3-Allyl-7-chlorooquinazoline-2,4(1H,3H)-dione

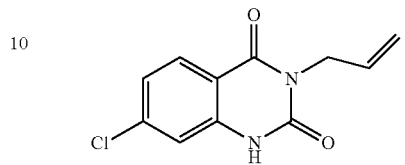

The title compound was prepared utilizing a similar procedure for Intermediate D2, using 2-amino-4-chlorobenzoic acid. LCMS (ES$^+$) m/z 236.98 (M+H)$^+$.

Intermediate D4: 3-Allyl-7-(trifluoromethyl)quinazoline-2,4(1H,3H)-dione

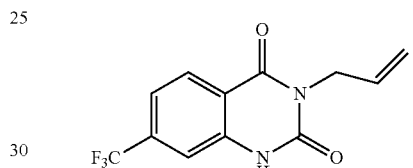

The title compound was prepared utilizing a similar procedure for Intermediate D2, using 2-amino-4-trifluoromethylbenzoic acid. LCMS (ES$^+$) m/z 271.25 (M+H)$^+$.

Intermediate D5: 3-Allyl-7-(methylsulfonyl)quinazoline-2,4(1H,3H)-dione

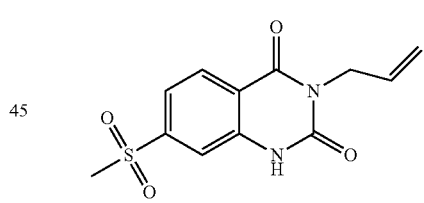

The title compound was prepared utilizing a similar procedure for Intermediate D2, using 2-amino-4-methylsulfonylbenzoic acid. LCMS (ES$^+$) m/z 281.3 (M+H)$^+$.

Intermediate D6:
3-Allyl-7-(methoxy)quinazoline-2,4(1H,3H)-dione

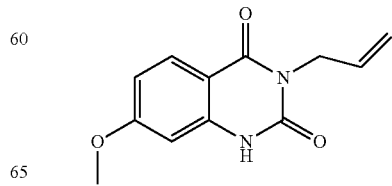

The title compound was prepared utilizing a similar procedure for intermediate D2, using 2-amino-4-methoxybenzoic acid. LCMS (ES+) m/z 233.1 (M+H)+.

Intermediate D7:
3-Allyl-8-methoxyquinazoline-2,4(1H,3H)-dione

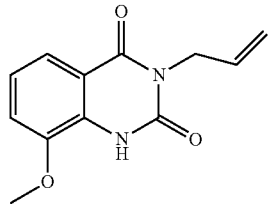 [SMILES: C=CCn1c(=O)[nH]c2c(OC)cccc2c1=O]

The title compound was prepared utilizing a similar procedure for Intermediate D2, using 2-amino-3-methoxybenzoic acid. LCMS (ES+) m/z 233.3 (M+H)+.

Intermediate D8:
3-Allyl-5-methoxyquinazoline-2,4(1H,3H)-dione

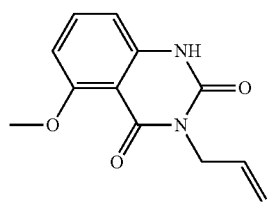 [SMILES: C=CCn1c(=O)[nH]c2cccc(OC)c2c1=O]

The title compound was prepared utilizing a similar procedure for Intermediate D2, using 2-amino-6-methoxybenzoic acid. LCMS (ES+) m/z 233.02 (M+H)+.

Intermediate D9:
3-Allyl-2-hydroxy-4H-pyrido[1,2-a]pyrimidin-4-one

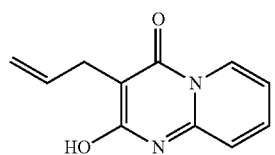

2-aminopyridine (996 mg, 10.58 mmol) and diethyl allylmalonate (2098 μl, 10.58 mmol) were combined and heated to 160° C. neat for 9 hours. The brown solution solidified upon cooling to room temperature. The solid was filtered and washed with Et₂O to yield the title compound as a tan solid (580 mg, 27%) LCMS (ES+) m/z 203.02 (M+H)+.

Intermediate D10: 3-allyl-2-hydroxy-8-methoxy-4H-pyrido[1,2-a]pyrimidin-4-one

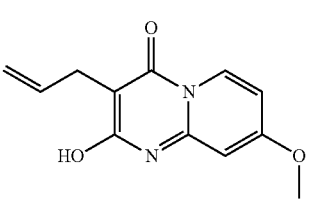 [SMILES: C=CCc1c(O)nc2cc(OC)ccn2c1=O]

Bis(pentachlorophenyl) allylmalonate (905 mg, 1.412 mmol) and triethylamine (0.359 ml, 2.58 mmol) were added to a slurry of 2-amino-4-methoxypyridine (160 mg, 1.289 mmol) in acetone (6.5 ml). The slurry was stirred for 16 hours, filtered, and washed with acetone to yield the title compound as a white solid (194 mg, 65%). LCMS (ES+) m/z 233.0 (M+H)+.

Example 1

(3aR,7S,10S,12R,23E,25aS)-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatiazacyclononadecino[12,11-b]isoquinoline-10-carboxamide

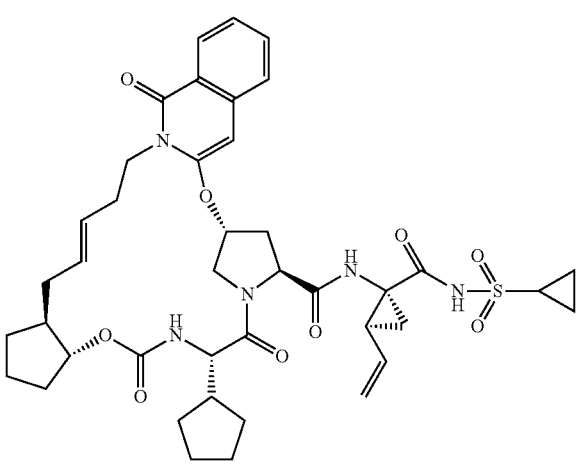 [SMILES: C=C[C@@H]1C[C@]1(NC(=O)[C@@H]1C[C@@H]2CN1C(=O)[C@H](C1CCCC1)NC(=O)O[C@@H]1CCC[C@H]1C/C=C/CCn1c(cc3ccccc3c1=O)O2)C(=O)NS(=O)(=O)C1CC1]

Step 1: 1-tert-Butyl 2-methyl (2S,4R)-4-[(2-but-3-en-1-yl-1-oxo-1,2-dihydroisoquinolin-3-yl)oxy]pyrrolidine-1,2-dicarboxylate

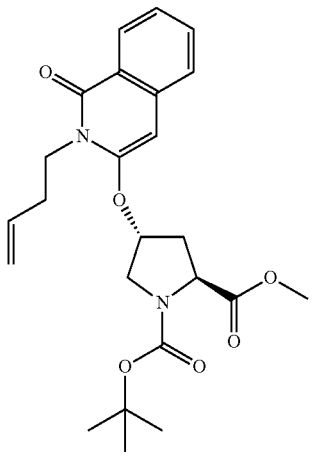 [SMILES: C=CCCn1c(O[C@@H]2C[C@@H](C(=O)OC)N(C(=O)OC(C)(C)C)C2)cc2ccccc2c1=O]

Cs₂CO₃ (1.1 g, 3.39 mmol) was added to a solution of 2-but-3-en-1-ylisoquinoline-1,3(2H,4H)-dione (0.49 g, 2.26 mmol) and 1-t-butyl 2-methyl (2S,4S)-4-{[(4-bromophenyl)sulfonyl]oxy}pyrrolidine-1,2-dicarboxylate (1.05 g, 2.26 mmol) in NMP (10 mL), and the reaction mixture was stirred for 16 hours at 40° C. An additional portion of 1-t-butyl 2-methyl (2S,4S)-4-{[(4-bromophenyl)sulfonyl]oxy}pyrrolidine-1,2-dicarboxylate (1.0 g, 2.16 mmol) was added, and the reaction mixture was stirred at 40° C. for 16 hours. The reaction mixture was cooled and poured onto a mixture of EtOAc and H₂O, and the layers were separated. The organic layer was washed with H₂O (2×), 1N HCl (1×) and brine, dried over Na₂SO₄, filtered and concentrated in vacuo. The resulting residue was purified by column chromatography (gradient elution, 10-40% EtOAc/Hexane) to afford the title compound (0.83 g, 83%) as an oil. LCMS (ES+) m/z 443.0 (M+H)⁺.

Step 2: Methyl (4R)-4-[(2-but-3-en-1-yl-1-oxo-1,2-dihydroisoquinolin-3-yl)oxy]-L-prolinate

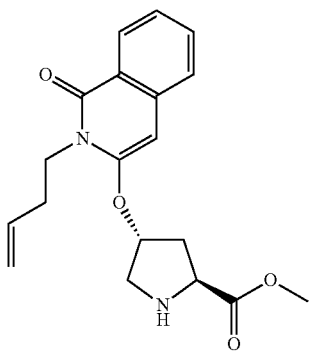 [SMILES: C=CCCn1c(O[C@H]2CN[C@H](C(=O)OC)C2)cc2ccccc2c1=O]

A portion of the product from Step 1 (150 mg, 0.34 mmol) was dissolved in CH₂Cl₂ (4 ml), cooled in an ice bath, and then added TFA (4 ml). The reaction was allowed to warm to room temperature and stir for 1.5 hours. The reaction was concentrated and the resulting oil was partitioned between CH₂Cl₂ and sated NaHCO₃, extracted with CH₂Cl₂ (2×), combined organics, washed with brine, dried organics over Na₂SO₄, filtered, concentrated in vacuo to yield the title compound as a oil (113 mg, 97%). LCMS (ES+) m/z 342.9 (M+H)⁺.

Step 3: Methyl (4R)-1-{(2S)-2-[({[(1R,2S)-2-allyl-cyclopentyl]oxy}carbonyl)amino]-2-cyclopentylacetyl}-4-[(2-but-3-en-1-yl-1-oxo-1,2-dihydroisoquinolin-3-yl)oxy]-L-prolinate

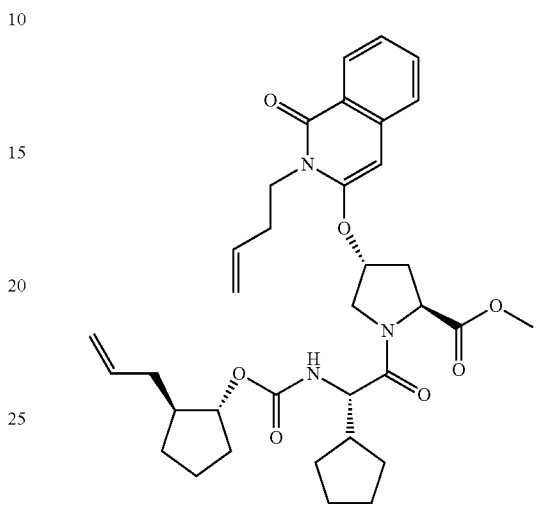

Intermediate B3 (356 mg, 1.2 mmol), HAM (424 mg, 1.115 mmol), and DIEA (0.487 ml, 2.79 mmol) were added to a solution of the product from Step 2 (318 mg, 0.929 mmol), in DMF (8 ml). After stirring 16 hours, the reaction mixture was diluted with EtOAc and washed with 1N HCl (2×), brine, sated NaHCO₃ (2×), brine. The organics were dried over Na₂SO₄, filtered, concentrated in vacuo, and the resulting residue was purified by column chromatography (gradient elution, 15-50% EtOAc/Hexane) to afford the title compound (0.276 g, 48%) as an oil. LCMS (ES+) m/z 620.2 (M+H)⁺.

Step 4: Methyl (3aR,7S,10S,12R,23E,25aS)-7-cyclopentyl-5,8,19-trioxo-1,2,3,3a,5,6,7,8,11,12,21,22,25,25a-tetradecahydro-10H,19H-9,12-methanocyclopenta[18,19][1,10,3,6,12]dioxatiazacyclononadecino[12,11-b]isoquinoline-10-carboxylate

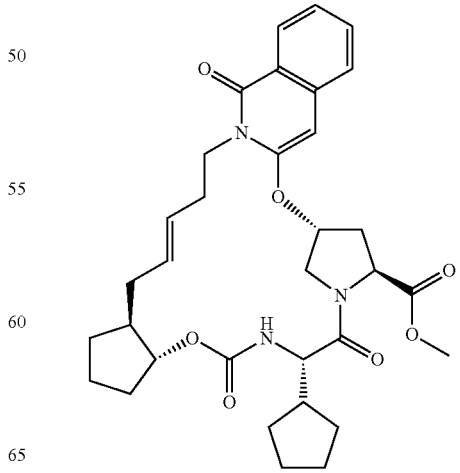

To a degassed solution of the product from Step 3 (390 mg, 0.63 mmol) in DCE (100 mL) was added p-benzoquinone (20.4 mg, 0.19 mmol) and Zhan 1b catalyst (73 mg, 0.094 mmol). After 16 hours, the reaction was concentrated in vacuo and the crude product was purified by column chromatography (gradient elution, 15-40% EtOAc/hexanes) to yield the title compound as a gray foam (215 mg, 53%). LCMS (ES+) m/z 592.1 (M+H)$^+$.

Step 5: (3aR,7S,10S,12R,23E,25aS)-7-cyclopentyl-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxylic acid

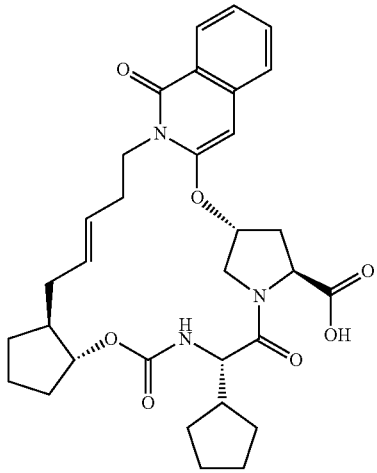 [SMILES: O=C1N[C@@H](C2CCCC2)C(=O)N2C[C@@H](C[C@H]2C(=O)O)Oc2cc3ccccc3c(=O)n2CC/C=C/C[C@@H]2CCC[C@H]2O1]

Lithium hydroxide monohydrate (5.77 μl, 0.208 mmol) was added to a solution of a portion of the product from Step 4 (40 mg, 0.068 mmol) in THF:MeOH:H$_2$O 2:1:1 (2 ml) and left stir 2 h. The reaction mixture was treated with 6N HCl (35 μL). The organics were removed under reduced pressure and the residual aqueous solution was extracted with EtOAc. The organics were washed with brine and dried over Na$_2$SO$_4$. Filtration and removal of the solvent afforded the title compound (39 mg, 100%) as a white solid. LCMS (ES+) m/z 578.1 (M+H)$^+$.

Step 6: (3aR,7S,10S,12R,23E,25aS)-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide Intermediate A1 (21.61 mg, 0.081 mmol), HATU (30.8 mg, 0.081 mmol), DIEA (0.047 ml, 0.270 mmol) were added to a solution of the product from Step 5 (39 mg, 0.068 mmol) in DMF (1 ml), and left stir 16 hours. The reaction was directly purified by reverse phase chromatography, and the resulting product was concentrated in vacuo to give the title compound as a white solid (30 mg, 56%). LCMS (ES+) m/z 790.2 (M+H)$^+$.

By following the procedures outlined in Example 1 and using the appropriate Intermediates A, B, and C, the following compounds were prepared.

| Ex. | Structure | Name | LRMS (M + H)$^+$ | Int. |
|---|---|---|---|---|
| 2 | 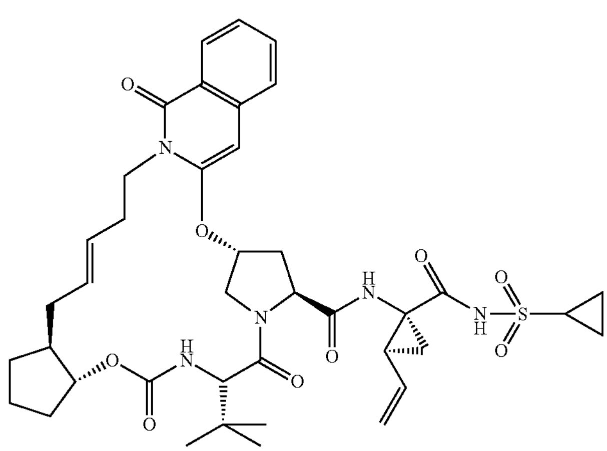 | (3aR,7S,10S,12R,23E,25aS)-7-tert-butyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | 778.1 | A1, B4, C1 |

| Ex. | Structure | Name | LRMS (M + H)+ | Int. |
|---|---|---|---|---|
| 3 | 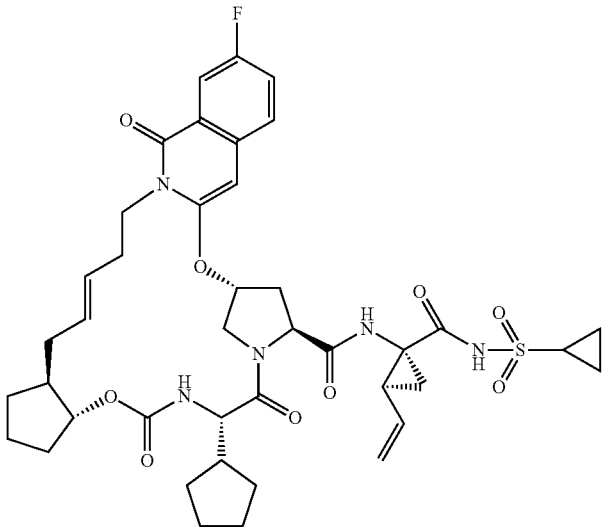 [SMILES: C=C[C@@H]1C[C@]1(NC(=O)[C@@H]1C[C@@H]2CN1C(=O)[C@H](C1CCCC1)NC(=O)O[C@@H]1CCC[C@H]1C/C=C/CCn1c(cc3ccc(F)cc3c1=O)O2)C(=O)NS(=O)(=O)C1CC1] | (3aR,7S,10S,12R,23E,25aS)-7-cyclopentyl-N-((1R,2S)-1-{[(cyclopropylsulfonyl)amino]carbonyl}-2-vinylcyclopropyl)-17-fluoro-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | 808.34 | A1, B3, C4 |
| 4 | 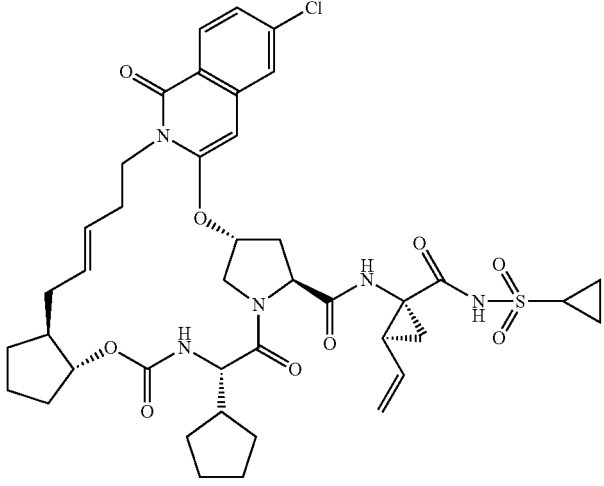 [SMILES: C=C[C@@H]1C[C@]1(NC(=O)[C@@H]1C[C@@H]2CN1C(=O)[C@H](C1CCCC1)NC(=O)O[C@@H]1CCC[C@H]1C/C=C/CCn1c(cc3cc(Cl)ccc3c1=O)O2)C(=O)NS(=O)(=O)C1CC1] | (3aR,7S,10S,12R,23E,25aS)-16-chloro-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | 824.31 | A1, B3, C3 |
| 5 | 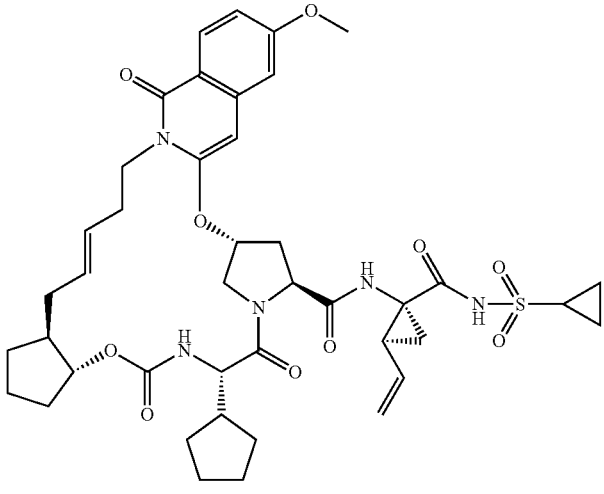 [SMILES: C=C[C@@H]1C[C@]1(NC(=O)[C@@H]1C[C@@H]2CN1C(=O)[C@H](C1CCCC1)NC(=O)O[C@@H]1CCC[C@H]1C/C=C/CCn1c(cc3cc(OC)ccc3c1=O)O2)C(=O)NS(=O)(=O)C1CC1] | (3aR,7S,10S,12R,23E,25aS)-7-cyclopentyl-N-((1R,2S)-1-{[(cyclopropylsulfonyl)amino]carbonyl}-2-vinylcyclopropyl)-16-methoxy-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | 792.2 | A1, B3, C2 |

-continued

| Ex. | Structure | Name | LRMS (M + H)+ | Int. |
|---|---|---|---|---|
| 6 | 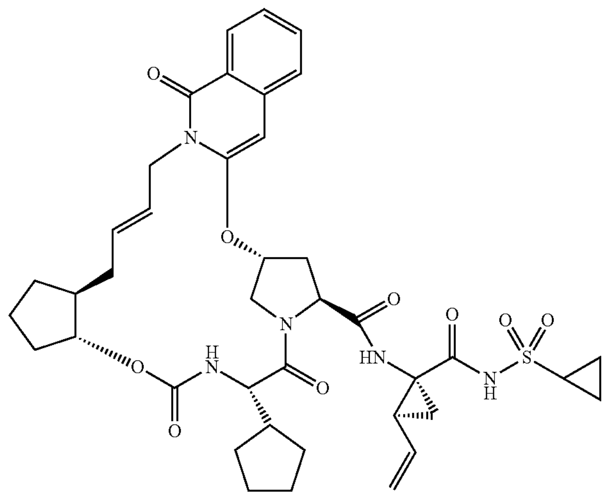 [SMILES: C=C[C@@H]1C[C@]1(NC(=O)[C@@H]1C[C@@H]2CN1C(=O)[C@H](C1CCCC1)NC(=O)O[C@@H]1CCC[C@H]1C/C=C/Cn1c(cc3ccccc3c1=O)O2)C(=O)NS(=O)(=O)C1CC1] | (3aR,7S,10S,12R,22E,24aS)-7-cyclopentyl-N-((1R,2S)-1-{[(cyclopropylsulfonyl)amino]carbonyl}-2-vinylcyclopropyl)-5,8,19-trioxo-2,3,3a,5,6,7,8,11,12,21,24,24a-dodecahydro-1H,10H,19H-9,12-methanocyclopenta[17,18][1,10,3,6,12]dioxatriazacyclooctadecino[12,11-b]isoquinoline-10-carboxamide | 776.15 | A1, B3, C5 |
| 7 | 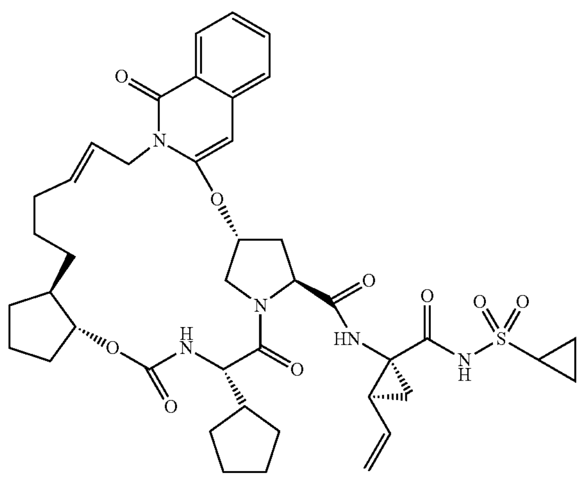 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCC/C=C/Cn1c(cc3ccccc3c1=O)O2)C(=O)NS(=O)(=O)C1CC1] | (3aR,7S,10S,12R,22E,26aR)-7-cyclopentyl-N-((1R,2S)-1-{[(cyclopropylsulfonyl)amino]carbonyl}-2-vinylcyclopropyl)-5,8,19-trioxo-2,3,3a,5,6,7,8,11,12,21,24,25,26,26a-tetradecahydro-1H,10H,19H-9,12-methanocyclopenta[19,20][1,10,3,6,12]dioxatriazacycloicosino[12,11-b]isoquinoline-10-carboxamide | 804.36 | A1, B1, C5 |
| 8 | 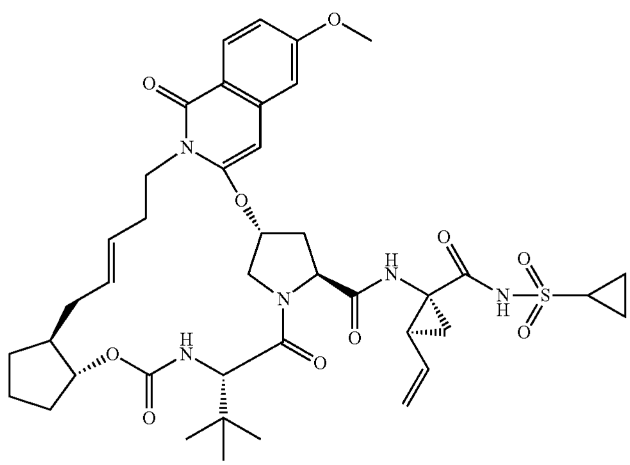 [SMILES: C=C[C@@H]1C[C@]1(NC(=O)[C@@H]1C[C@@H]2CN1C(=O)[C@H](C(C)(C)C)NC(=O)O[C@@H]1CCC[C@H]1C/C=C/CCn1c(cc3cc(OC)ccc3c1=O)O2)C(=O)NS(=O)(=O)C1CC1] | (3aR,7S,10S,12R,23E,25aS)-7-tert-butyl-N-((1R,2S)-1-{[(cyclopropylsulfonyl)amino]carbonyl}-2-vinylcyclopropyl)-16-methoxy-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | 808.18 | A1, B4, C2 |

-continued

| Ex. | Structure | Name | LRMS (M + H)+ | Int. |
|---|---|---|---|---|
| 9 | 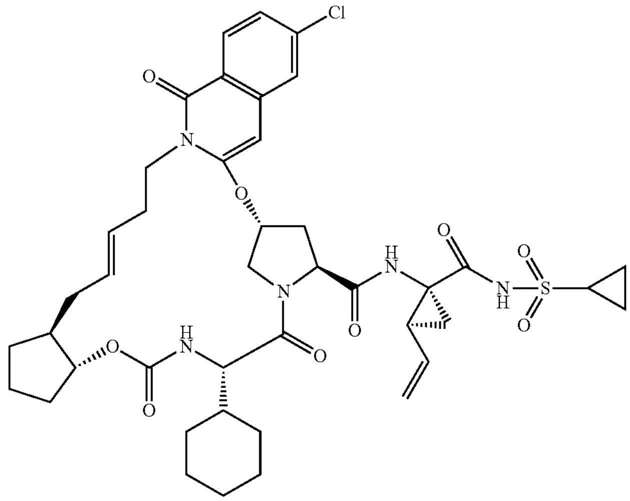 [SMILES: C=C[C@@H]1C[C@]1(NC(=O)[C@@H]1C[C@@H]2CN1C(=O)[C@H](C1CCCCC1)NC(=O)O[C@@H]1CCC[C@H]1C/C=C/CCn1c(cc3cc(Cl)ccc3c1=O)O2)C(=O)NS(=O)(=O)C1CC1] | (3aR,7S,10S,12R,23E,25aS)-16-chloro-7-cyclohexyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | 838.11 | A1, B2, C3 |
| 10 | 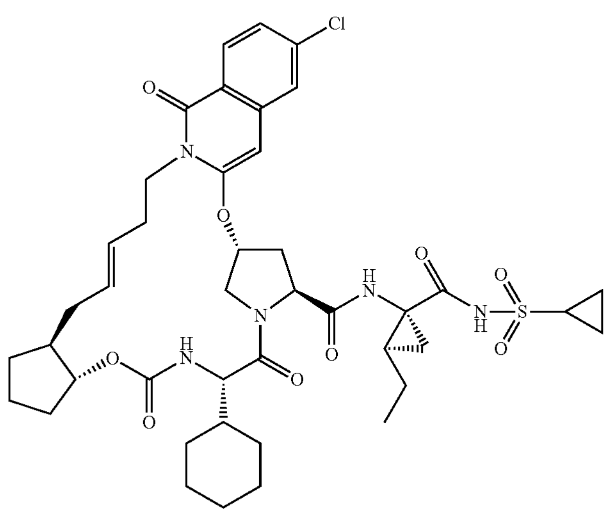 [SMILES: CC[C@@H]1C[C@]1(NC(=O)[C@@H]1C[C@@H]2CN1C(=O)[C@H](C1CCCCC1)NC(=O)O[C@@H]1CCC[C@H]1C/C=C/CCn1c(cc3cc(Cl)ccc3c1=O)O2)C(=O)NS(=O)(=O)C1CC1] | (3aR,7S,10S,12R,23E,25aS)-16-chloro-7-cyclohexyl-N-((1R,2R)-1-{[(cyclopropylsulfonyl)amino]carbonyl}-2-ethylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | 840.17 | A3, B2, C3 |

| Ex. | Structure | Name | LRMS (M + H)+ | Int. |
|---|---|---|---|---|
| 11 | 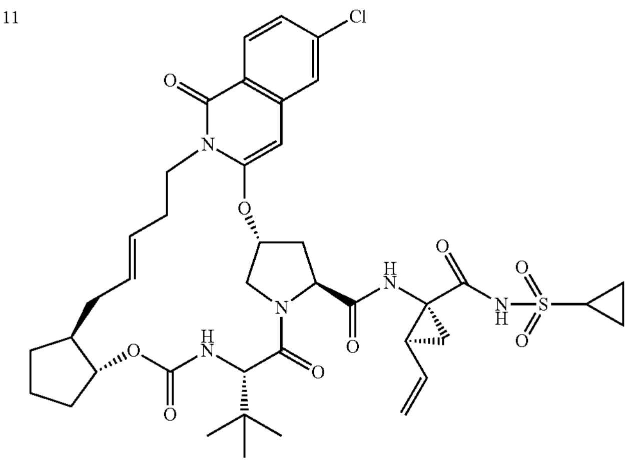 | (3aR,7S,10S,12R,23E,25aS)-7-tert-butyl-16-chloro-N-((1R,2S)-1-{[(cyclopropylsulfonyl)amino]carbonyl}-2-vinylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | 812.11 | A1, B4, C3 |
| 12 | 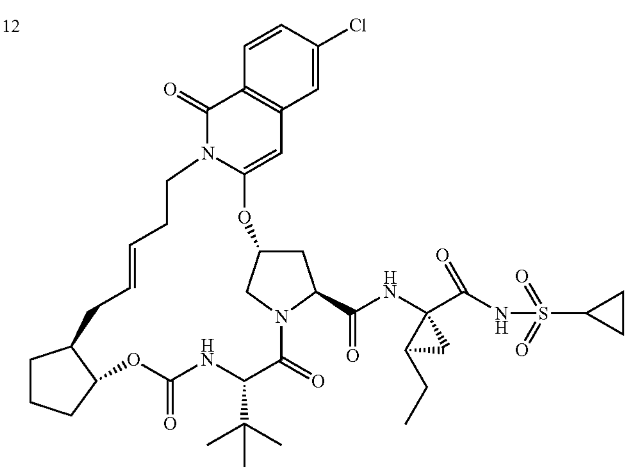 | (3aR,7S,10S,12R,23E,25aS)-7-tert-butyl-16-chloro-N-((1R,2R)-1-{[(cyclopropylsulfonyl)amino]carbonyl}-2-ethylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | 814.17 | A3, B4, C3 |

Example 13

(3aR,7S,10S,12R,25aR)-7-cyclopentyl-N-((1R,2S)-1-{[(cyclopropylsulfonyl)amino]carbonyl}-2-vinyl-cyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclotionadecino[12,11-b]isoquinoline-10-carboxamide

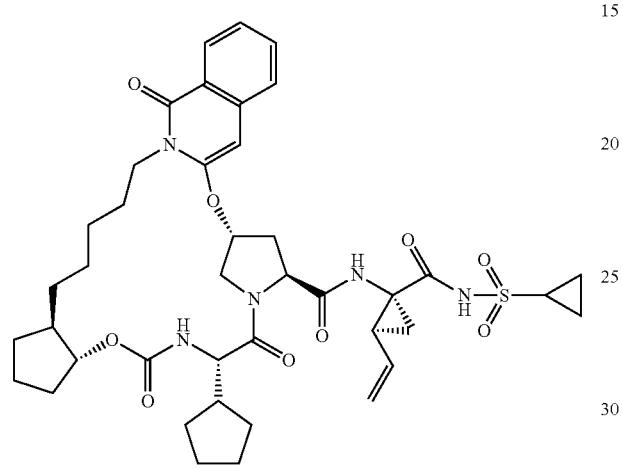

Step 1: Methyl (3aR,7S,10S,12R,25aR)-7-cyclopentyl-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxylate

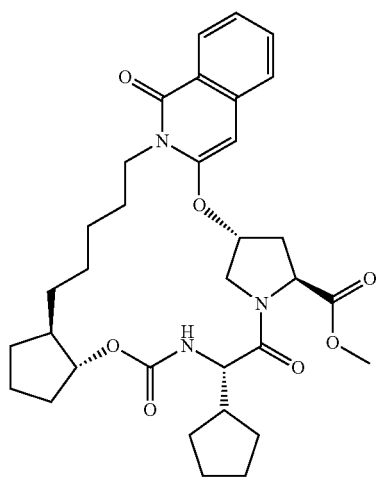 [SMILES: COC(=O)[C@@H]1C[C@@H]2CN1C(=O)[C@H](C1CCCC1)NC(=O)O[C@@H]1CCC[C@H]1CCCCCn1c(cc3ccccc3c1=O)O2]

Pd/C (21.58 mg, 0.020 mmol) was added to a solution of the product from Example 1, Step 4 (80 mg, 0.135 mmol) in THF (4 ml) and stirred under a hydrogen atmosphere for 16 hours. The reaction was filtered through a syringe filter and the organics were removed under reduced pressure. The resulting residue was purified by column chromatography (gradient elution, 20-45% EtOAc/hexanes) to yield the title compound as a gray foam (66 mg, 82%). LCMS (ES$^+$) m/z 594.1 (M+H)$^+$. Rh/C, EtOAc-MeOH (50:50).

Step 2: (3 aR,7S,10S,12R,25aR)-7-cyclopentyl-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxylic acid

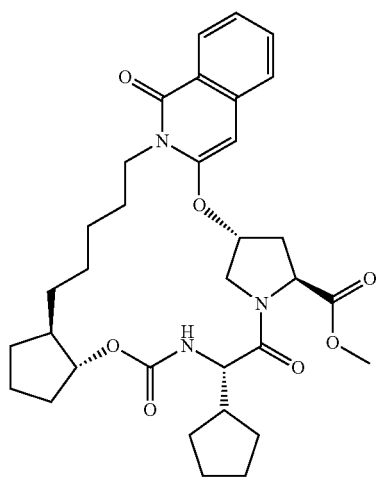 [SMILES: COC(=O)[C@@H]1C[C@@H]2CN1C(=O)[C@H](C1CCCC1)NC(=O)O[C@@H]1CCC[C@H]1CCCCCn1c(cc3ccccc3c1=O)O2]

Using the product from Step 1, the title compound was prepared according to the procedure in Example 1 Step 5. LCMS (ES$^+$) m/z 580.1 (M+H)$^+$.

Step 3: (3aR,7S,10S,12R,25aR)-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide Using the product from Step 2, the title compound was prepared according to the procedure in Example 1 Step 6. LCMS (ES$^+$) adz 792.2 (M+H)$^+$.

By following the procedures outlined in Example 1, Steps 1-4 through Example 13 and using the appropriate A, B, and C intermediates, the following compounds were prepared.

| Ex. | Structure | Name | LRMS (M + H)+ | Int. |
|---|---|---|---|---|
| 14 | 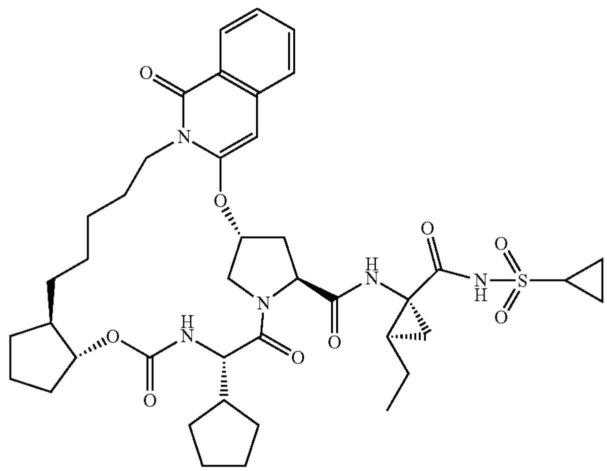 [SMILES: CC[C@@H]1C[C@]1(NC(=O)[C@@H]1C[C@@H]2CN1C(=O)[C@H](C1CCCC1)NC(=O)O[C@@H]1CCC[C@H]1CCCCCn1c(cc3ccccc3c1=O)O2)C(=O)NS(=O)(=O)C1CC1] | (3aR,7S,10S,12R,25aR)-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | 794.2 | A3, B3, C1 |
| 15 | 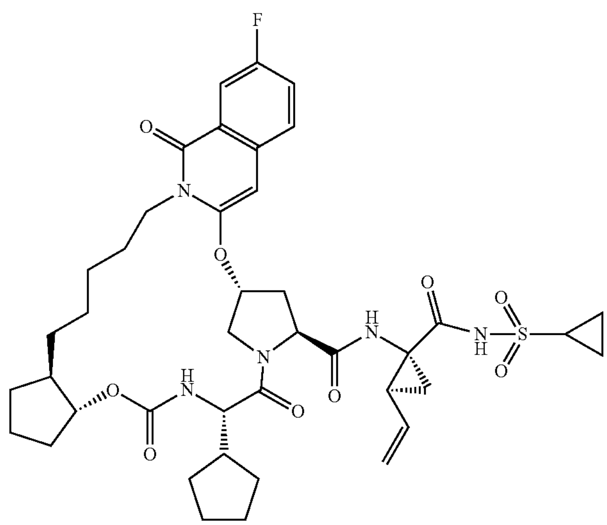 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(cc3ccc(F)cc3c1=O)O2)C(=O)NS(=O)(=O)C1CC1] | (3aR,7S,10S,12R,25aR)-7-cyclopentyl-N-((1R,2S)-1-{[(cyclopropylsulfonyl)amino]carbonyl}-2-vinylcyclopropyl)-17-fluoro-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | 810.35 | A1, B3, C4 |
| 16 | 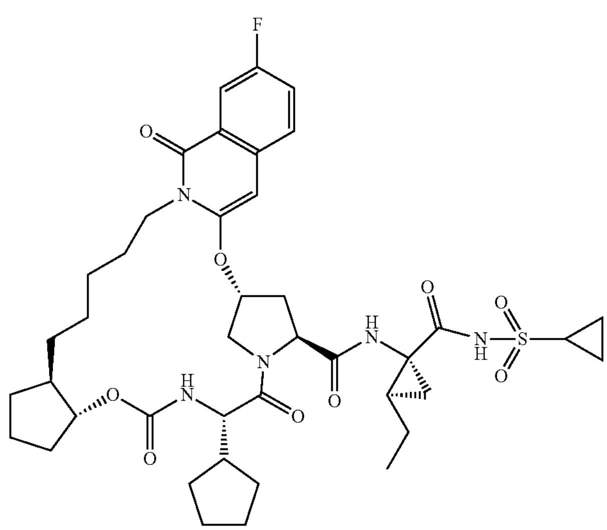 [SMILES: CC[C@@H]1C[C@]1(NC(=O)[C@@H]1C[C@@H]2CN1C(=O)[C@H](C1CCCC1)NC(=O)O[C@@H]1CCC[C@H]1CCCCCn1c(cc3ccc(F)cc3c1=O)O2)C(=O)NS(=O)(=O)C1CC1] | (3aR,7S,10S,12R,25aR)-7-cyclopentyl-N-((1R,2R)-1-{[(cyclopropylsulfonyl)amino]carbonyl}-2-ethylcyclopropyl)-17-flouoro-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | 812.37 | A3, B3, C4 |

| Ex. | Structure | Name | LRMS (M + H)+ | Int. |
|---|---|---|---|---|
| 17 | 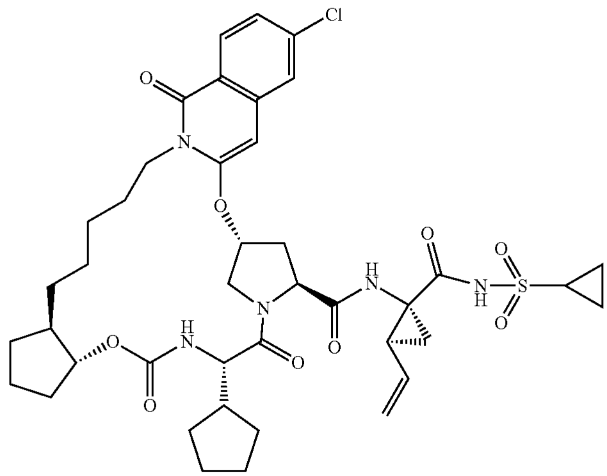 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(cc3cc(Cl)ccc3c1=O)O2)C(=O)NS(=O)(=O)C1CC1] | (3aR,7S,10S,12R,25aR)-16-chloro-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | 826.33 | A1, B3, C3 |
| 18 | 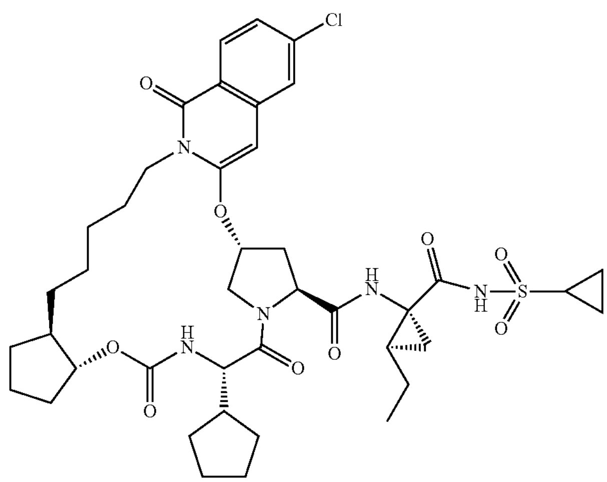 [SMILES: CC[C@@H]1C[C@]1(NC(=O)[C@@H]1C[C@@H]2CN1C(=O)[C@H](C1CCCC1)NC(=O)O[C@@H]1CCC[C@H]1CCCCCn1c(cc3cc(Cl)ccc3c1=O)O2)C(=O)NS(=O)(=O)C1CC1] | (3aR,7S,10S,12R,25aR)-16-chloro-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | 828.34 | A3, B3, C3 |
| 19 | 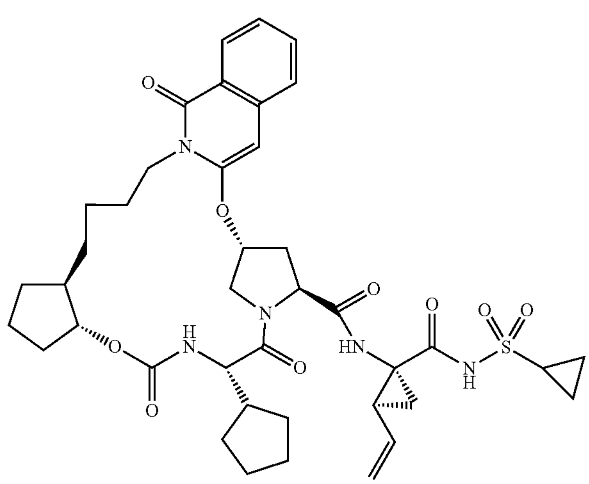 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCn1c(cc3ccccc3c1=O)O2)C(=O)NS(=O)(=O)C1CC1] | (3aR,7S,10S,12R,24aR)-7-cyclopentyl-N-((1R,2S)-1-{[(cycloproylsulfonyl)amino]carbonyl}-2-vinylcyclopropyl)-5,8,19-trioxo-2,3,3a,5,6,7,8,11,12,21,22,23,24,24a-tetradecahydro-1H,10H,19H-9,12-methanocyclopenta[17,18][1,10,3,6,12]dioxatriazacyclooctadecino[12,11-b]isoquinoline-10-carboxamide | 778.35 | A1, B3, C5 |

| Ex. | Structure | Name | LRMS (M + H)+ | Int. |
|---|---|---|---|---|
| 20 | 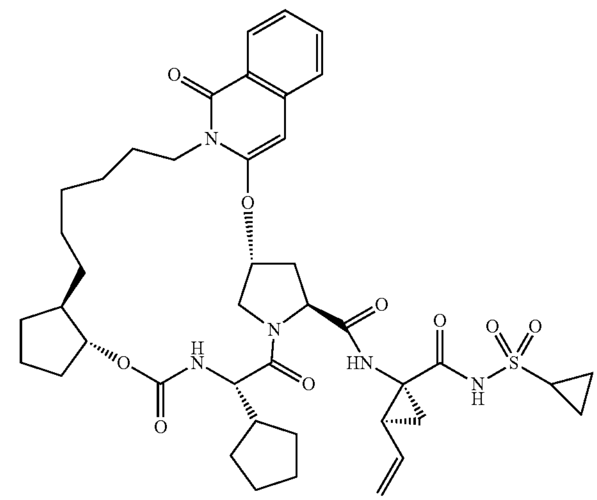 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCCn1c(cc3ccccc3c1=O)O2)C(=O)NS(=O)(=O)C1CC1] | (3aR,7S,10S,12R,26aR)-7-cyclopentyl-N-((1R,2S)-1-{[(cyclopropylsulfonyl)amino]carbonyl}-2-vinylcyclopropyl)-5,8,19-trioxo-2,3,3a,5,6,7,8,11,12,21,22,23,24,25,26,26a-hexadecahydro-1H,10H,19H-9,12-methanocyclopenta[19,20][1,10,3,6,12]dioxatriazacycloicosino[12,11-b]isoquinoline-10-carboxamide | 806.38 | A1, B1, C5 |
| 21 | 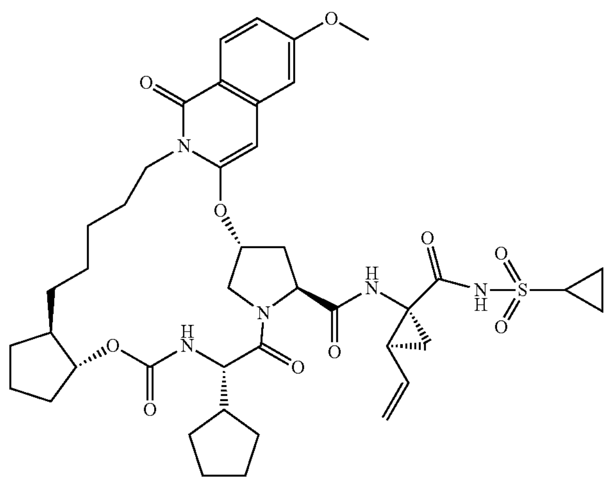 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(cc3cc(OC)ccc3c1=O)O2)C(=O)NS(=O)(=O)C1CC1] | (3aR,7S,10S,12R,25aR)-7-cyclopentyl-N-((1R,2S)-1-{[(cyclopropylsulfonyl)amino]carbonyl}-2-vinylcyclopropyl)-16-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | 822.16 | A1, B3, C2 |
| 22 | 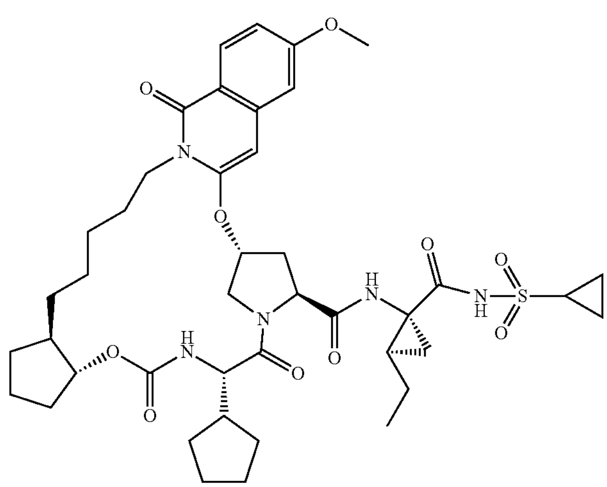 [SMILES: CC[C@@H]1C[C@]1(NC(=O)[C@@H]1C[C@@H]2CN1C(=O)[C@H](C1CCCC1)NC(=O)O[C@@H]1CCC[C@H]1CCCCCn1c(cc3cc(OC)ccc3c1=O)O2)C(=O)NS(=O)(=O)C1CC1] | (3aR,7S,10S,12R,25aR)-7-cyclopentyl-N-((1R,2R)-1-{[(cyclopropylsulfonyl)amino]carbonyl}-2-ethylcyclopropyl)-16-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | 824.18 | A3, B3, C2 |

| Ex. | Structure | Name | LRMS (M + H)+ | Int. |
|---|---|---|---|---|
| 23 | 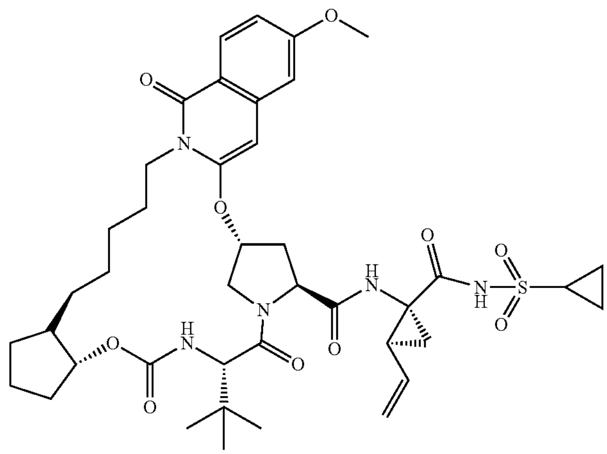 | (3aR,7S,10S,12R,25aR)-7-tert-butyl-N-((1R,2S)-1-{[(cyclopropylsulfonyl)amino]carbonyl}-2-vinylcyclopropyl)-16-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b] isoquinoline-10-carboxamide | 810.19 | A1, B4, C2 |
| 24 | 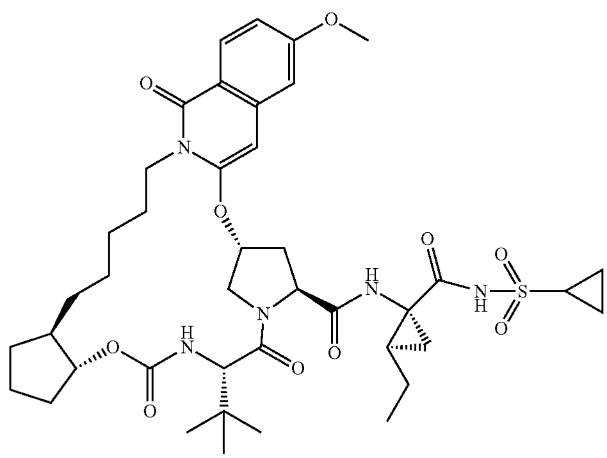 [SMILES: CC[C@@H]1C[C@]1(NC(=O)[C@@H]1C[C@@H]2CN1C(=O)[C@H](C(C)(C)C)NC(=O)O[C@@H]1CCC[C@H]1CCCCCn1c(cc3cc(OC)ccc3c1=O)O2)C(=O)NS(=O)(=O)C1CC1] | (3aR,7S,10S,12R,25aR)-7-tert-butyl-N-((1R,2R)-1-{[(cyclopropylsulfonyl)amino]carbonyl}-2-ethylcyclopropyl)-16-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b] isoquinoline-10-carboxamide | 812.19 | A3, B4, C2 |
| 25 | 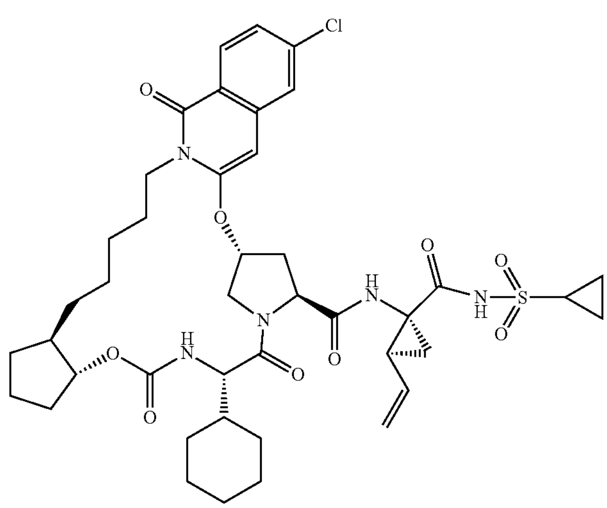 [SMILES: C=C[C@@H]1C[C@]1(NC(=O)[C@@H]1C[C@@H]2CN1C(=O)[C@H](C1CCCCC1)NC(=O)O[C@@H]1CCC[C@H]1CCCCCn1c(cc3cc(Cl)ccc3c1=O)O2)C(=O)NS(=O)(=O)C1CC1] | (3aR,7S,10S,12R,25aR)-16-chloro-7-cyclohexyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b] isoquinoline-10-carboxamide | 840.16 | A1, B2, C3 |

| Ex. | Structure | Name | LRMS (M + H)+ | Int. |
|---|---|---|---|---|
| 26 | 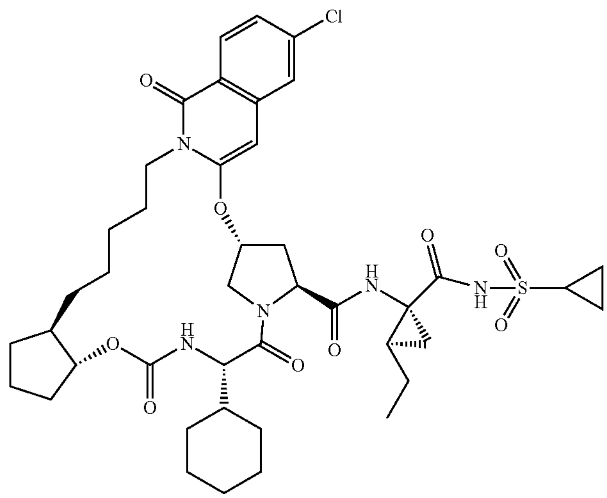 [SMILES: CC[C@@H]1C[C@]1(NC(=O)[C@@H]1C[C@@H]2CN1C(=O)[C@H](C1CCCCC1)NC(=O)O[C@@H]1CCC[C@H]1CCCCCn1c(cc3cc(Cl)ccc3c1=O)O2)C(=O)NS(=O)(=O)C1CC1] | (3aR,7S,10S,12R,25aR)-16-chloro-7-cyclohexyl-N-((1R,2R)-1-{[(cyclopropylsulfonyl)amino]carbonyl}-2-ethylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | 842.16 | A3, B2, C3 |
| 27 | 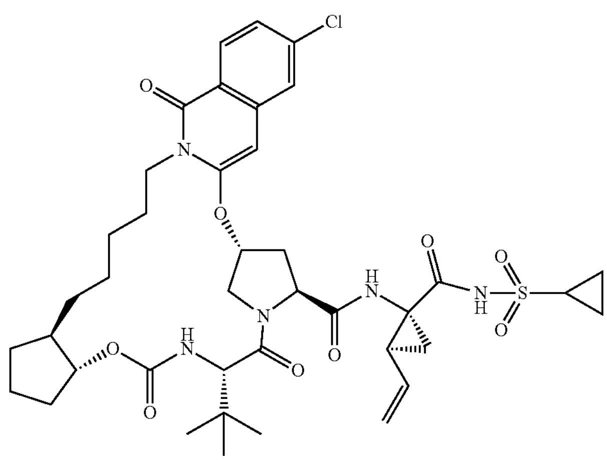 [SMILES: C=C[C@@H]1C[C@]1(NC(=O)[C@@H]1C[C@@H]2CN1C(=O)[C@H](C(C)(C)C)NC(=O)O[C@@H]1CCC[C@H]1CCCCCn1c(cc3cc(Cl)ccc3c1=O)O2)C(=O)NS(=O)(=O)C1CC1] | (3aR,7S,10S,12R,25aR)-7-tert-butyl-16-chloro-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | 814.12 | A1, B4, C3 |
| 28 | 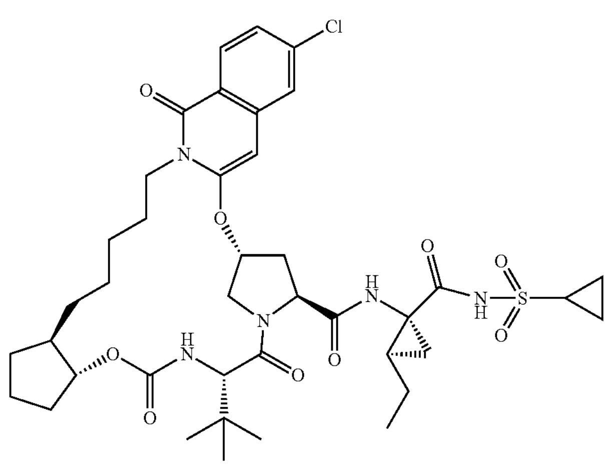 [SMILES: CC[C@@H]1C[C@]1(NC(=O)[C@@H]1C[C@@H]2CN1C(=O)[C@H](C(C)(C)C)NC(=O)O[C@@H]1CCC[C@H]1CCCCCn1c(cc3cc(Cl)ccc3c1=O)O2)C(=O)NS(=O)(=O)C1CC1] | (3aR,7S,10S,12R,25aR)-7-tert-butyl-16-chloro-N-((1R,2R)-1-{[(cyclopropylsulfonyl)amino]carbonyl}-2-ethylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinolin-10-carboxamide | 816.14 | A3, B4, C3 |

| Ex. | Structure | Name | LRMS (M + H)+ | Int. |
|---|---|---|---|---|
| 29 | 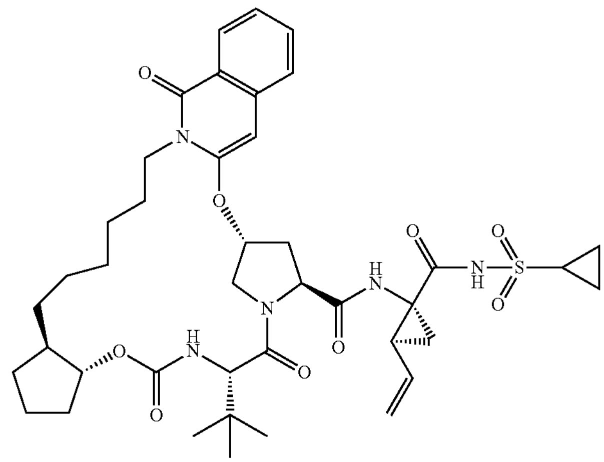 | (3aR,7S,10S,12R,26aR)-7-tert-butyl-N-((1R,2S)-1-{[(cyclopropylsulfonyl)amino]carbonyl}-2-vinylcyclopropyl)-5,8,19-trioxo-2,3,3a,5,6,7,8,11,12,21,22,23,24,25,26,26a-hexadecahydro-1H,10H,19H-9,12-methanocyclopenta[19,20][1,10,3,6,12]dioxatriazacycloicosino[12,11-b]isoquinoline-10-carboxamide | 794.21 | A1, B5, C1 |
| | Diastereomeric separation during purification as in Example 1, Step 4 | | | |
| 30 | 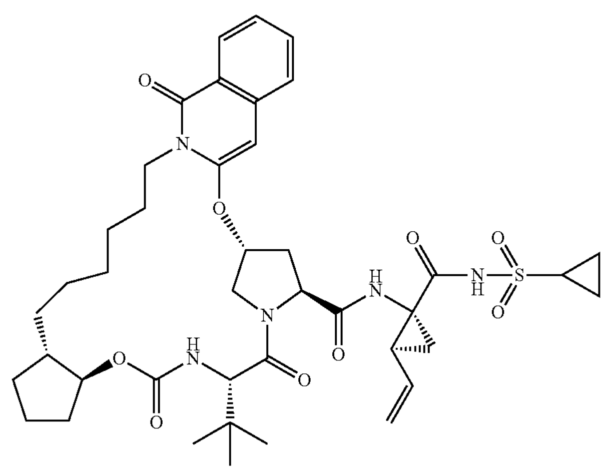 | (3aS,7S,10S,12R,26aS)-7-tert-butyl-N-((1R,2S)-1-{[(cyclopropylsulfonyl)amino]carbonyl}-2-vinylcyclopropyl)-5,8,19-trioxo-2,3,3a,5,6,7,8,11,12,21,22,23,24,25,26,26a-hexadecahydro-1H,10H,19H-9,12-methanocyclopenta[19,20][1,10,3,6,12]dioxatriazacycloicosino[12,11-b]isoquinoline-10-carboxamide | 794.20 | A1, B5, C1 |
| | Diastereomeric separation during purification as in Example 1, Step 4 | | | |

| Ex. | Structure | Name | LRMS (M + H)+ | Int. |
|---|---|---|---|---|
| 31 | 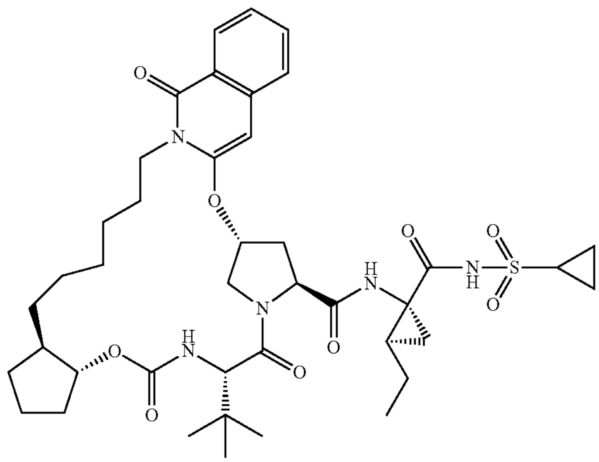 | (3aR,7S,10S,12R,26aR)-7-tert-butyl-N-((1R,2R)-1-{[(cyclopropylsulfonyl)amino]carbonyl}-2-ethylcyclopropyl)-5,8,19-trioxo-2,3,3a,5,6,7,8,11,12,21,22,23,24,25,26,26a-hexadecahydro-1H,10H,19H-9,12-methanocyclopenta[19,20][1,10,3,6,12]dioxatriazacycloicosino[12,11-b]isoquinoline-10-carboxamide | 796.23 | A3, B5, C1 |
| | Diastereomeric separation during purification as in Example 1, Step 4 | | | |
| 32 | 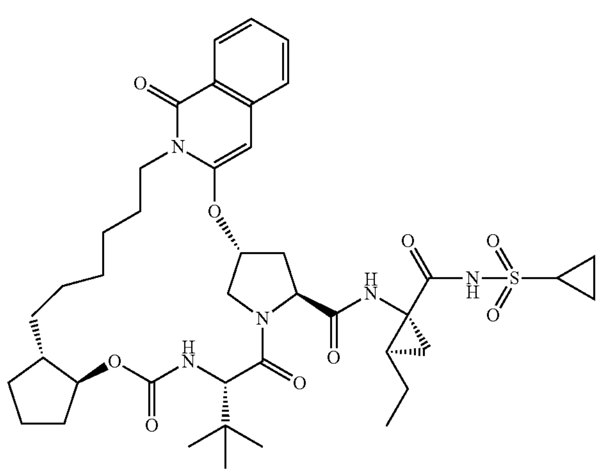 | (3aS,7S,10S,12R,26aS)-7-tert-butyl-N-((1R,2R)-1-{[(cyclopropylsulfonyl)amino]carbonyl}-2-ethylcyclopropyl)-5,8,19-trioxo-2,3,3a,5,6,7,8,11,12,21,22,23,24,25,26,26a-hexadecahydro-1H,10H,19H-9,12-methanocyclopenta[19,20][1,10,3,6,12]dioxatriazacycloicosino[12,11-b]isoquinoline-10-carboxamide | 796.22 | A3, B5, C1 |
| | Diastereomeric separation during purification as in Example 1, Step 4 | | | |

| Ex. | Structure | Name | LRMS (M + H)+ | Int. |
|---|---|---|---|---|
| 33 | 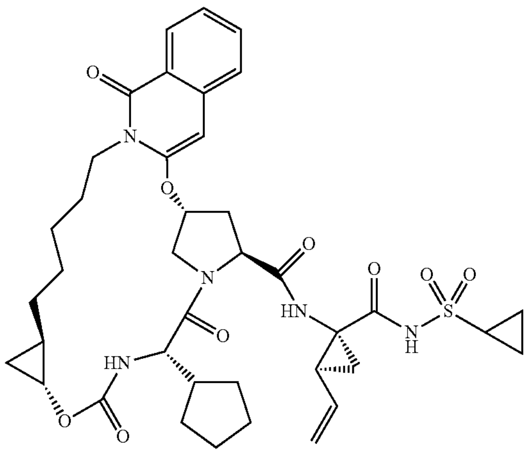 | (1aR,5S,8S,10R,23aR)-5-cyclopentyl-N-((1R,2S)-1-{[(cyclopropylsulfonyl)amino]carbonyl}-2-vinylcyclopropyl)-3,6,17-trioxo-1,1a,3,4,5,6,9,10,19,20,21,22,23,23a-tetradecahydro-8H,17H-7,10-methanocyclopropa[18,19][1,10,3,6,12]dioxatriazacyclononadecino[12,11-b] isoquinoline-8-carboxamide | 764.33 | A1, B6, C5 |
| | Diastereomeric separation during purification as in Example 1, Step 4 | | | |
| 34 | 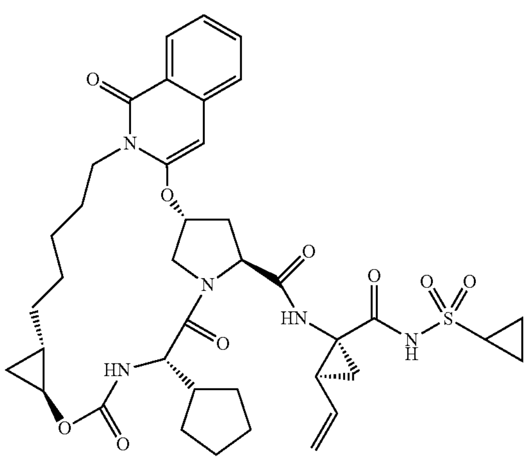 | (1aS,5S,8S,10R,23aS)-5-cyclopentyl-N-((1R,2S)-1-{[(cyclopropylsulfonyl)amino]carbonyl}-2-vinylcyclopropyl)-3,6,17-trioxo-1,1a,3,4,5,6,9,10,19,20,21,22,23,23a-tetradecahydro-8H,17H-7,10-methanocyclopropa[18,19][1,10,3,6,12]dioxatriazacyclononadecino[12,11-b] isoquinoline-8-carboxamide | 764.33 | A1, B6, C5 |
| | Diastereomeric separation during purification as in Example 1, Step 4 | | | |

| Ex. | Structure | Name | LRMS (M + H)+ | Int. |
|---|---|---|---|---|
| 35 | 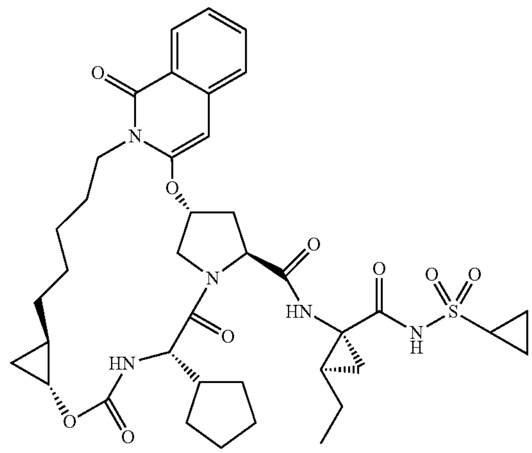 | (1aR,5S,8S,10R,23aR)-5-cyclopentyl-N-((1R,2R)-1-{[(cyclopropylsulfonyl)amino]carbonyl}-2-ethylcyclopropyl)-3,6,17-trioxo-1,1a,3,4,5,6,9,10,19,20,21,22,23,23a-tetradecahydro-8H,17H-7,10-methanocyclopropa[18,19][1,10,3,6,12]dioxatriazacyclononadecino[12,11-b] isoquinoline-8-carboxamide | 766.19 | A3, B6, C5 |
| | Diastereomeric separation during purification as in Example 1, Step 4 | | | |
| 36 | 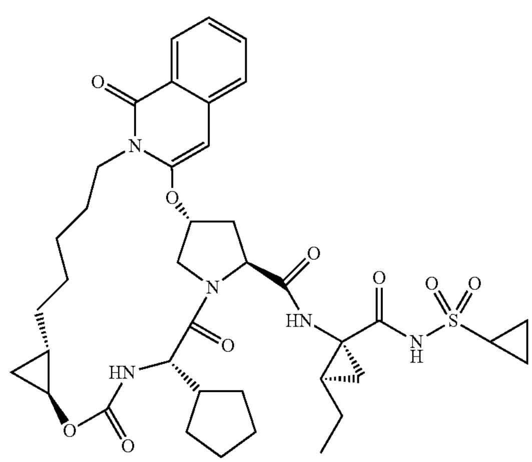 | (1aS,5S,8S,10R,23aS)-5-cyclopentyl-N-((1R,2R)-1-{[(cyclopropylsulfonyl)amino]carbonyl}-2-ethylcyclopropyl)-3,6,17-trioxo-1,1a,3,4,5,6,9,10,19,20,21,22,23,23a-tetradecahydro-8H,17H-7,10-methanocyclopropa[18,19][1,10,3,6,12]dioxatriazacyclononadecino[12,11-b] isoquinoline-8-carboxamide | 766.36 | A3, B6, C5 |
| | Diastereomeric separation during purification as in Example 1, Step 4 | | | |

Example 37

(3aR,7S,10S,12R,25aR)-7-cyclopentyl-N-((1R,2S)-1-{[(cyclopropylsulfonyl)amino]carbonyl}-2-vinyl-cyclopropyl)-5,8,19-trioxo-1,2,3,3a,5,6,7,8,11,12,21,21a,22,22a,23,24,25,25a-octadecahydro-10H,19H-9,12-methanocyclopenta[19,20]cyclopropa[14,15][1,10,3,6,12]dioxatriazacycloicosino[12,11-b]isoquinoline-10-carboxamide

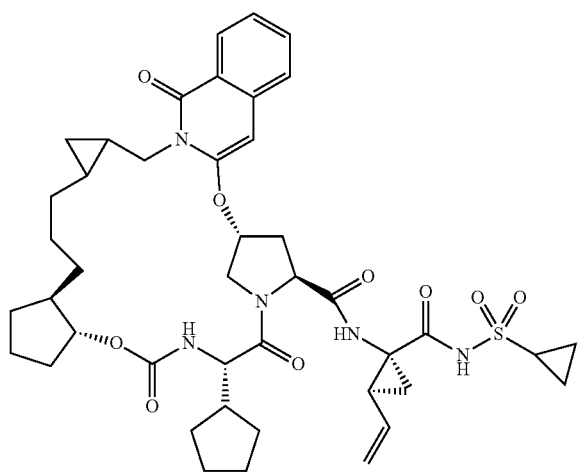 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCC1CC1Cn1c(cc3ccccc3c1=O)O2)C(=O)NS(=O)(=O)C1CC1]

Step 1: Methyl (3aR,7S,10S,12R,22E,26aR)-7-cyclopentyl-5,8,19-trioxo-2,3,3a,5,6,7,8,11,12,21,24,25,26,26a-tetradecahydro-1H,10H,19H-9,12-methanocyclopenta[19,20][1,10,3,6,12]dioxatriazacycloicosino[12,11-b]isoquinoline-10-carboxylate

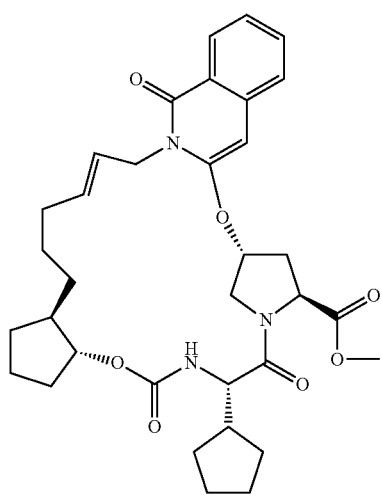 [SMILES: COC(=O)[C@@H]1C[C@@H]2CN1C(=O)[C@H](C1CCCC1)NC(=O)O[C@@H]1CCC[C@H]1CCC/C=C/Cn1c(cc3ccccc3c1=O)O2]

The title compound was prepared utilizing a similar procedure for Example 1 utilizing Intermediates C5 and B1. LCMS (ES⁺) m/z 606.2 (M+H)⁺.

Step 2: Methyl (3aR,7S,10S,12R,25aR)-7-cyclopentyl-5,8,19-trioxo-1,2,3,3a,5,6,7,8,11,12,21,21a,22,22a,23,24,25,25a-octadecahydro-10H,19H-9,12-methanocyclopenta[19,20]cyclopropa[14,15][1,10,3,6,12]dioxatriazacycloicosino[12,11-b]isoquinoline-10-carboxylate

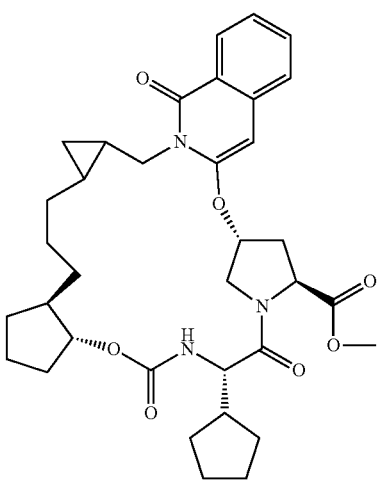 [SMILES: COC(=O)[C@@H]1C[C@@H]2CN1C(=O)[C@H](C1CCCC1)NC(=O)O[C@@H]1CCC[C@H]1CCCC1CC1Cn1c(cc3ccccc3c1=O)O2]

PdOAc$_2$ (6.67 mg, 0.030 mmol) was added to a mixture of methyl (3aR,7S,10S,12R,22E,26aR)-7-cyclopentyl-5,8,19-trioxo-2,3,3a,5,6,7,8,11,12,21,24,25,26,26a-tetradecahydro-1H,10H,19H-9,12-methanocyclopenta[19,20][1,10,3,6,12]dioxatriazacycloicosino[12,11-b]isoquinoline-10-carboxylate (90 mg, 0.149 mmol) in diethyl ether/THF (2 ml), and the mixture allowed to stir for 5 min. To this mixture was added dropwise a solution of diazomethane (0.97 mmol, 10 eq) in diethyl ether (2 mL). The reaction was stirred for 10 min, and an additional charge of diazomethane (2 mL) and catalyst added. An additional 2 charges of diazomethane solution (2 mL) and catalyst were added over 1 hr resulting in ~95% conversion. The reaction mixture was allowed to evaporate with a nitrogen bleed and the residue purified by preparatory HPLC to give the title compound. (60 mg, 65%). LCMS (ES+) m/z 620.1 (M+H)+.

Step 3: (3aR,7S,10S,12R,25aR)-7-cyclopentyl-5,8,19-trioxo-1,2,3,3a,5,6,7,8,11,12,21,21a,22,22a,23,24,25,25a-octadecahydro-10H,19H-9,12-methanocyclopenta[19,20]cyclorora[14,15][1,10,3,6,12]dioxatriazacycloicosino[12,11-b]isoquinoline-10-carboxylic acid

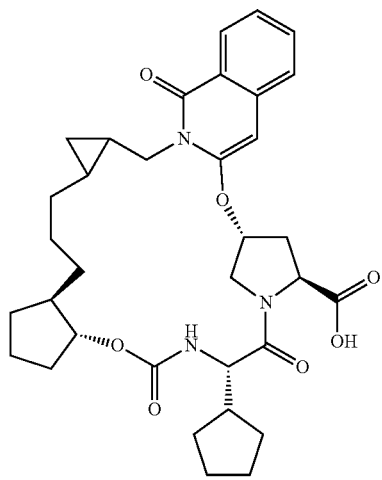 [SMILES: O=C1N[C@@H](C2CCCC2)C(=O)N2C[C@@H](C[C@H]2C(=O)O)Oc2cc3ccccc3c(=O)n2CC2CC2CCC[C@@H]2CCC[C@H]2O1]

The title compound was prepared in a similar manner as Example 1 Step 5 utilizing methyl (3aR,7S,10S,12R,25aR)-7-cyclopentyl-5,8,19-trioxo-1,2,3,3a,5,6,7,8,11,12,21,21a,22,22a,23,24,25,25a-octadecahydro-10H,19H-9,12-methanocyclopenta[19,20]cyclopropa[14,15][1,10,3,6,12]dioxatriazacycloicosino[12,11-b]isoquinoline-10-carboxylate in 100% yield. LCMS (ES+) tri/z 606.1 (M+H)+.

Step 4: (3aR,7S,10S,12R,25aR)-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,21a,22,22a,23,24,25,25a-octadecahydro-10H,19H-9,12-methanocyclopenta[19,20]cyclopropa[14,15][1,10,3,6,12]dioxatriazacycloicosino[12,11-b]isoquinoline-10-carboxamide

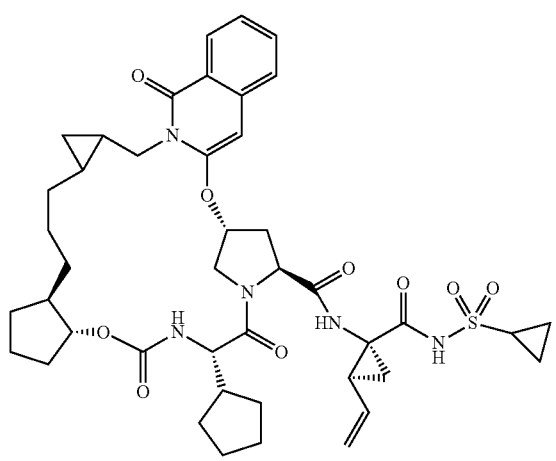 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCC1CC1Cn1c(cc3ccccc3c1=O)O2)C(=O)NS(=O)(=O)C1CC1]

The title compound was prepared in a similar manner as Example 1 Step 6, utilizing (3aR,7S,10S,12R,25aR)-7-cyclopentyl-5,8,19-trioxo-1,2,3,3a,5,6,7,8,11,12,21,21a,22,22a,23,24,25,25a-octadecahydro-10H,19H-9,12-methanocyclopenta[19,20]cyclopropa[14,15][1,10,3,6,12]dioxatriazacycloicosino[12,11-b]isoquinoline-10-carboxylic acid in 66% yield. LCMS (ES+) m/z 818.4 (M+H)+.

Example 38

(3aR,7S,10S,12R,24aS)-16-chloro-7-cyclopentyl-N-((1R,2S)-1-{[(cyclopropylsulfonyl)amino]carbonyl}-2-vinylcyclopropyl)-5,8,19-trioxo-2,3,3a,5,6,7,8,11,12,21,22,22a,23,23a,24,24a-hexadecahydro-1H,10H,19H-9,12-methanocyclopenta[18,19]cyclopropa[15,16][1,10,3,6,12]dioxatriazacyclononadecino[12,11-b]isoquinoline-10-carboxamide

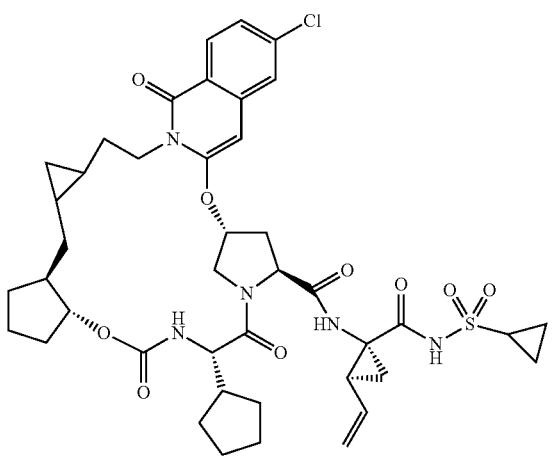 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC1CC1CCn1c(cc3cc(Cl)ccc3c1=O)O2)C(=O)NS(=O)(=O)C1CC1]

The title compound was prepared in a similar manner as Example 37, utilizing Intermediates C3 and B3. LCMS (ES+) m/z 838.2 (M+H)+.

Example 39

(3aR,7S,10S,12R,22E,25aS)-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide The title compound was prepared in a similar manner as Example 1 Step 1 utilizing 3-allylquinazoline-2,4(1H,3H)-dione in 83% yield. LCMS (ES⁻) m/z 430.0 (M+H)⁺.

Step 2: Methyl (4R)-4-[(3-allyl-4-oxo-3,4-dihydroquinazolin-2-yl)oxy]-L-prolinate

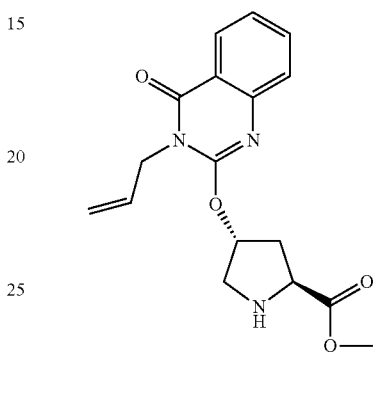

The title compound was prepared utilizing a similar procedure for Example 1 Step 2, utilizing 1-tert-butyl 2-methyl (2S,4R)-4-[(3-allyl-4-oxo-3,4-dihydroquinazolin-2-yl)oxy]pyrrolidine-1,2-dicarboxylate in 99% yield. LCMS (ES⁺) m/z 330.0 (M+H)⁺.

Step 3: Methyl (4R)-4-[(3-allyl-4-oxo-3,4-dihydroquinazolin-2-yl)oxy]-1-{(2S)-2-[({[(1R,2S)-2-but-3-en-1-ylcyclopentyl]oxy}carbonyl)amino]-2-cyclopentylacetyl}-L-prolinate

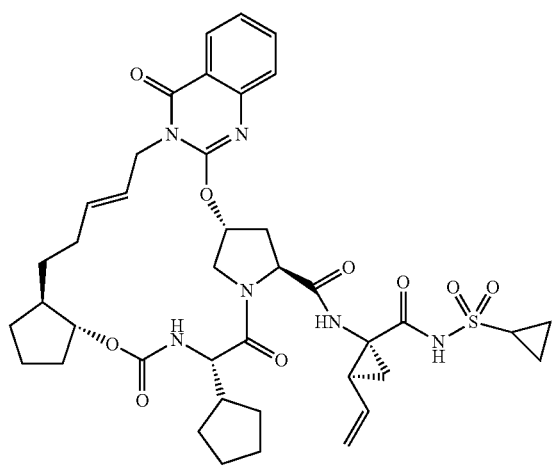 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3ccccc3c1=O)O2)C(=O)NS(=O)(=O)C1CC1]

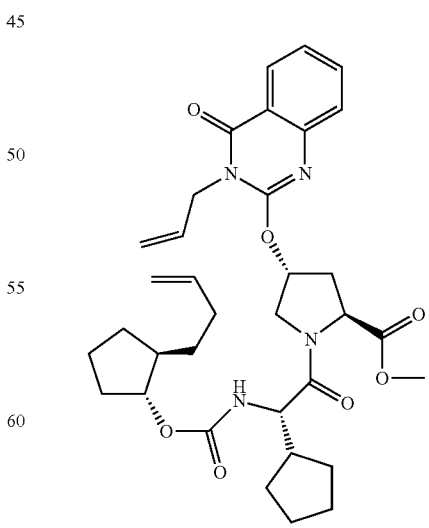

Step 1: 1-text-butyl 2-methyl (2S,4R)-4-[(3-allyl-4-oxo-3,4-dihydroquinazolin-2-yl)oxy]pyrrolidine-1,2-dicarboxylate

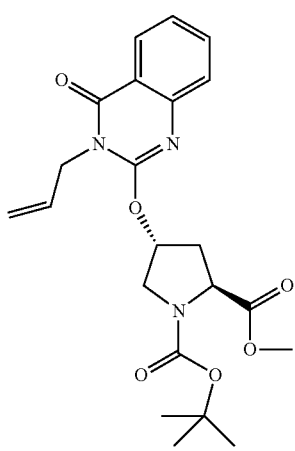 [SMILES: C=CCn1c(O[C@@H]2C[C@@H](C(=O)OC)N(C(=O)OC(C)(C)C)C2)nc2ccccc2c1=O]

The title compound was prepared in a similar manner as Example 1 Step 3, utilizing methyl (4R)-4-[(3-allyl-4-oxo-3, 4-dihydroquinazolin-2-yl)oxy]-L-prolinate and Intermediate B7 in 64% yield. LCMS (ES+) m/z 621.1 (M+H)+.

Step 4: Methyl (3aR,7S,10S,12R,22E,25aS)-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate

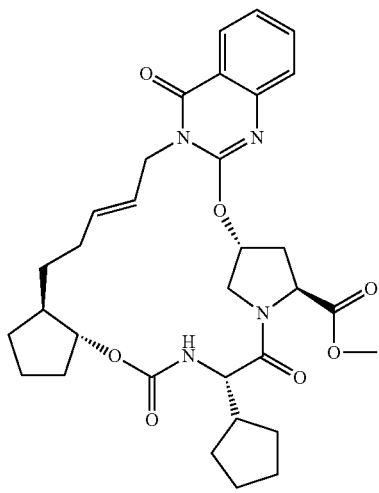 [SMILES: COC(=O)[C@@H]1C[C@@H]2CN1C(=O)[C@H](C1CCCC1)NC(=O)O[C@@H]1CCC[C@H]1CC/C=C/Cn1c(nc3ccccc3c1=O)O2]

The title compound was prepared in a similar manner as Example 1 Step 4, utilizing methyl (4R)-4-[(3-allyl-4-oxo-3,4-dihydroquinazolin-2-yl)oxy]-1-{(2S)-2-[({[(1R,2S)-2-but-3-en-1-ylcyclopentyl]oxy}carbonyl)amino]-2-cyclopentylacetyl}-L-prolinate in 93% yield. LCMS (ES+) m/z 593.1 (M+H)+.

Step 5: (3aR,7S,10S,12R,22E,25aS)-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylic acid

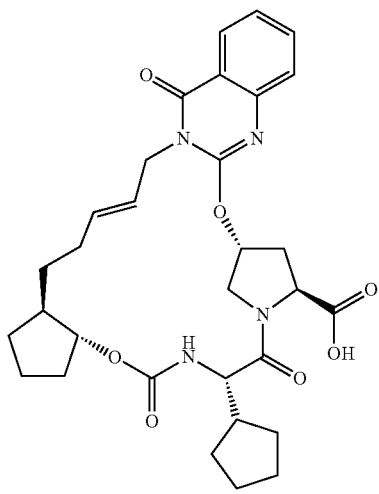

The title compound was prepared in a similar manner as Example 1 Step 5 utilizing methyl (3aR,7S,10S,12R,22E,25aS)-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate in 100% yield. LCMS (ES+) m/z 579.1 (M+H)+.

Step 6: (3aR,7S,10S,12R,22E,25aS)-7-cyclopentyl-N-((1R,2,5)-1-{[(cyclopropylsulfonyl)amino]carbonyl}-2-vinylcyclopropyl)-5,8,19-trioxo-1,2,3,3a,5,6,7,8,11,12,21,24,25,25a-tetradecahydro-10H,19H-9,12-methanocyclopenta[18,19][11,10,3,6,12]dioxatriazacyclononadecino[11,12-b]quinazoline-10-carboxamide

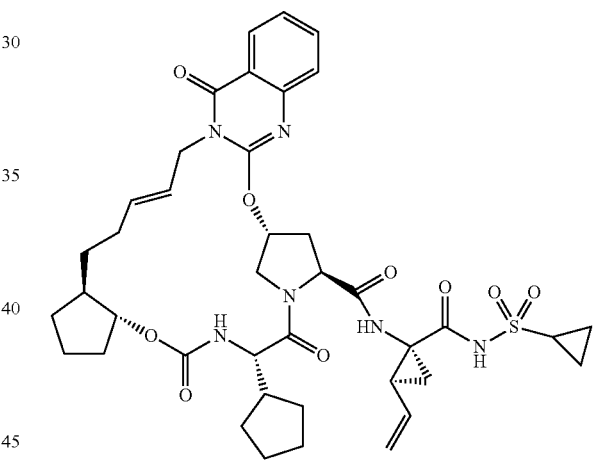

The title compound was prepared in a similar manner as Example 1 Step 6, utilizing (3aR,7S,10S,12R,22E,25aS)-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylic acid in 64% yield. LCMS (ES+) m/z 791.2 (M+H)+.

By following the procedures outlined in Example 39 and using the appropriate A, B, and D intermediates, the following compounds were prepared.

| Ex. | Structure | Name | LRMS (M + H)+ | Int. |
|---|---|---|---|---|
| 40 | 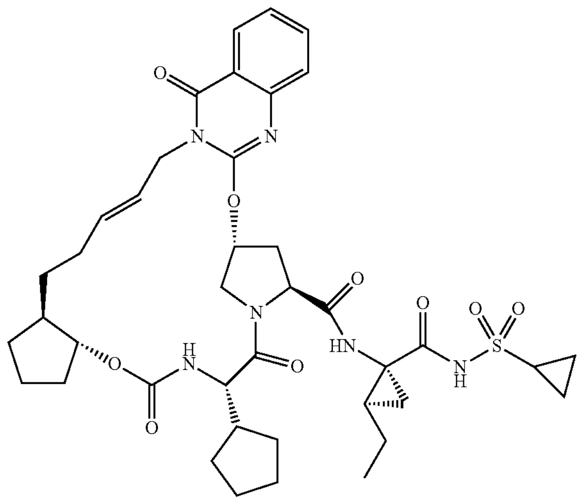 [SMILES: CC[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3ccccc3c1=O)O2)C(=O)NS(=O)(=O)C1CC1] | (3aR,7S,10S,12R,22E,25aS)-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 793.4 | A3, B7, D1 |
| 41 | 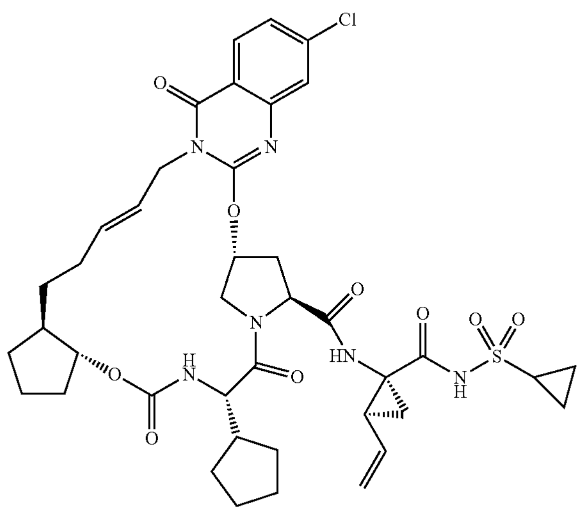 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3cc(Cl)ccc3c1=O)O2)C(=O)NS(=O)(=O)C1CC1] | (3aR,7S,10S,12R,22E,25aS)-16-chloro-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 825.1 | A1, B7, D3 |
| 42 | 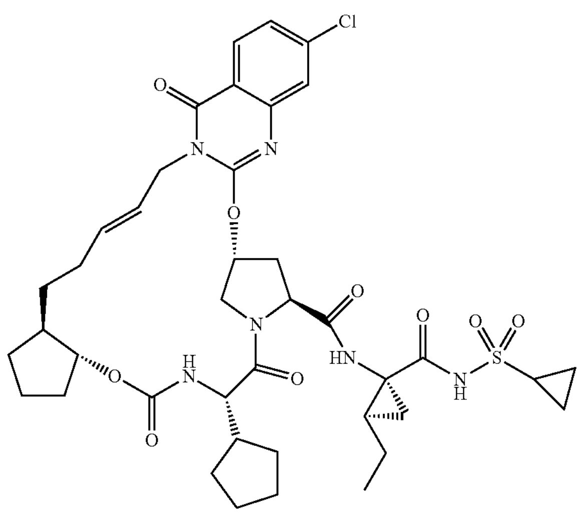 [SMILES: CC[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3cc(Cl)ccc3c1=O)O2)C(=O)NS(=O)(=O)C1CC1] | (3aR,7S,10S,12R,22E,25aS)-16-chloro-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 827.3 | A3, B7, D3 |

| Ex. | Structure | Name | LRMS (M + H)+ | Int. |
|---|---|---|---|---|
| 43 | 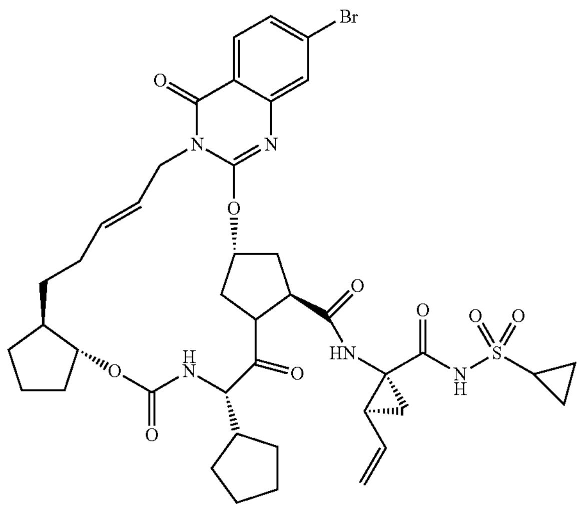 [SMILES: C=C[C@@H]1C[C@]1(NC(=O)[C@@H]1C[C@@H]2CC1C(=O)[C@H](C1CCCC1)NC(=O)O[C@@H]1CCC[C@H]1CC/C=C/Cn1c(nc3cc(Br)ccc3c1=O)O2)C(=O)NS(=O)(=O)C1CC1] | (3aR,7S,10S,12R,22E,25aS)-16-bromo-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazatriazacyclononadecino[11,12-b]quinazoline-10-carboxamide | 869.3 | A1, B7, D2 |
| 44 | 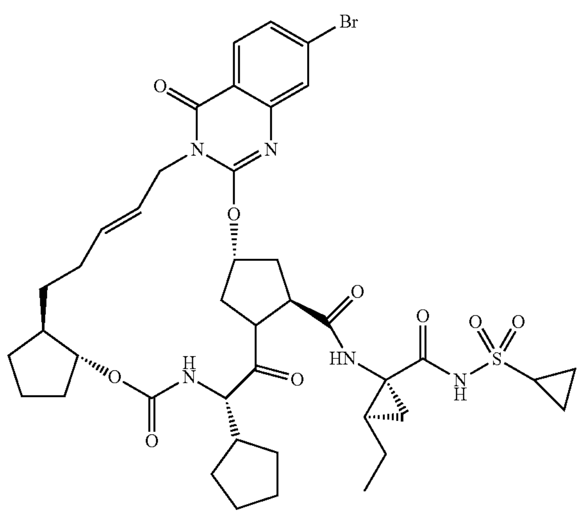 | (3aR,7S,10S,12R,22E,25aS)-16-bromo-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 871.3 | A3, B7, D2 |
| 45 | 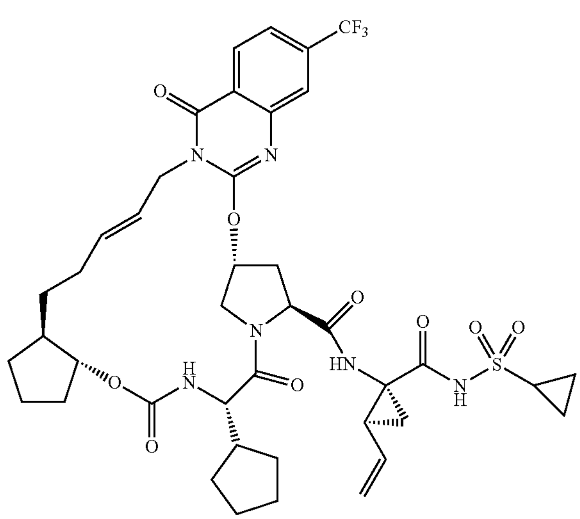 | (3aR,7S,10S,12R,22E,25aS)-7-cyclopentyl-N-((1R,2S)-1-{[(cyclopropylsulfonyl)amino]carbonyl}-2-vinylcyclopropyl)-5,8,19-trioxo-16-(trifluoromethyl)-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 859.3 | A1, B7, D4 |

| Ex. | Structure | Name | LRMS (M + H)+ | Int. |
|---|---|---|---|---|
| 46 | 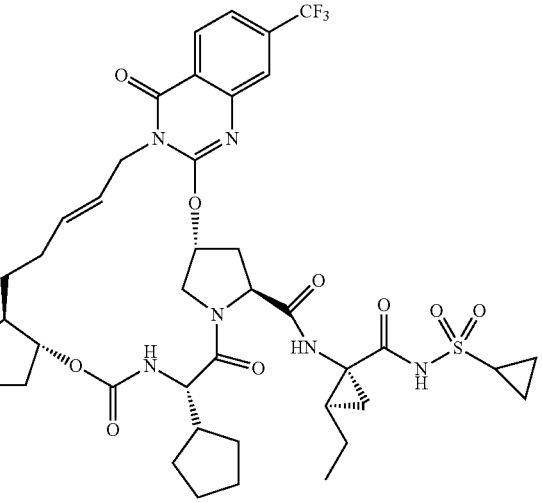 | (3aR,7S,10S,12R,22E,25aS)-7-cyclopentyl-N-((1R,2R)-1-{[(cyclopropylsulfonyl)amino]carbonyl}-2-ethylcyclopropyl)-5,8,19-trioxo-16-(trifluoromethyl)-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 861.3 | A3, B7, D4 |
| 47 | 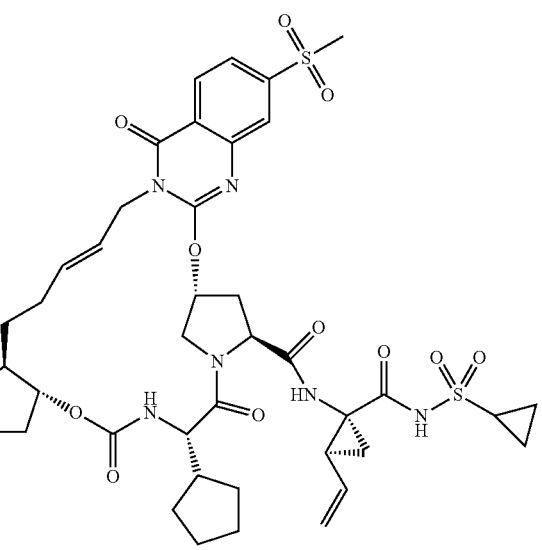 | (3aR,7S,10S,12R,22E,25aS)-7-cyclopentyl-N-((1R,2S)-1-{[(cyclopropylsulfonyl)amino]carbonyl}-2-vinylcyclopropyl)-16-(methylsulfonyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 869.3 | A1, B7, D5 |
| 48 | 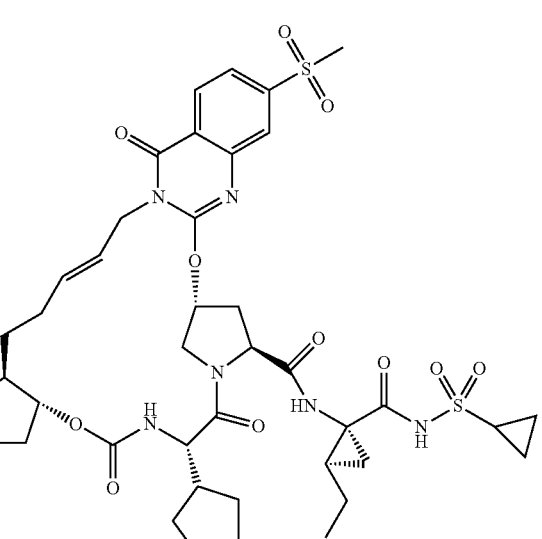 | (3aR,7S,10S,12R,22E,25aS)-7-cyclopentyl-N-((1R,2R)-1-{[(cyclopropylsulfonyl)amino]carbonyl}-2-ethylcyclopropyl)-16-(methylsulfonyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 871.3 | A3, B7, D5 |

| Ex. | Structure | Name | LRMS (M + H)+ | Int. |
|---|---|---|---|---|
| 49 | 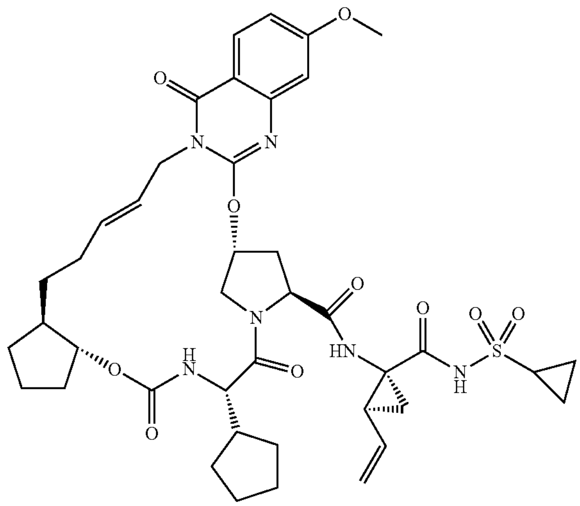 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3cc(OC)ccc3c1=O)O2)C(=O)NS(=O)(=O)C1CC1] | (3aR,7S,10S,12R,22E,25aS)-7-cyclopentyl-N-((1R,2S)-1-{[(cyclopropylsulfonyl)amino]carbonyl}-2-vinylcyclopropyl)-16-methoxy-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 821.1 | A1, B7, D6 |
| 50 | 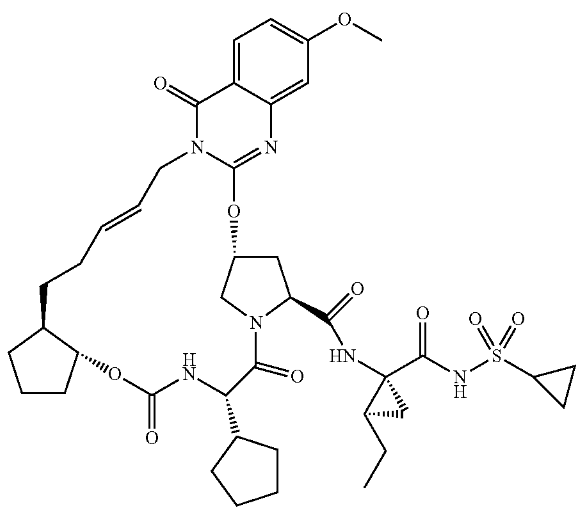 [SMILES: CC[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3cc(OC)ccc3c1=O)O2)C(=O)NS(=O)(=O)C1CC1] | (3aR,7S,10S,12R,22E,25aS)-7-cylcopentyl-N-((1R,2R)-1-{[(cyclopropylsulfonyl)amino]carbonyl}-2-ethylcyclopropyl)-16-methoxy-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 823.2 | A3, B7, D6 |
| 51 | 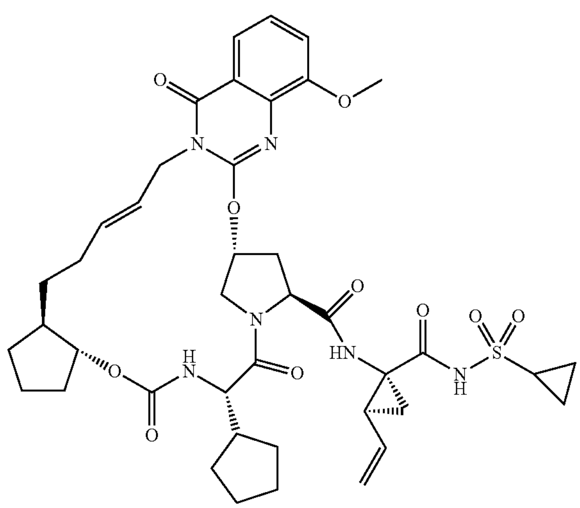 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3c(OC)cccc3c1=O)O2)C(=O)NS(=O)(=O)C1CC1] | (3aR,7S,10S,12R,22E,25aS)-7-cyclopentyl-N-((1R,2S)-2-{[(cyclopropylsulfonyl)amino]carbonyl}-2-vinylcyclopropyl)-15-methoxy-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 821.3 | A1, B7, D7 |

-continued

| Ex. | Structure | Name | LRMS (M + H)+ | Int. |
|---|---|---|---|---|
| 52 | 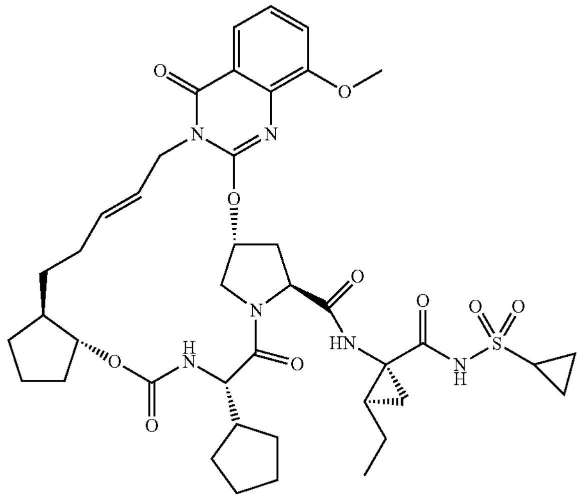 [SMILES: CC[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3c(OC)cccc3c1=O)O2)C(=O)NS(=O)(=O)C1CC1] | (3aR,7S,10S,12R,22E,25aS)-7-cyclopentyl-N-((1R,2R)-1-{[(cyclopropylsulfonyl)amino]carbonyl}-2-ethylcyclopropyl)-15-methoxy-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 823.3 | A3, B7, D7 |
| 53 | 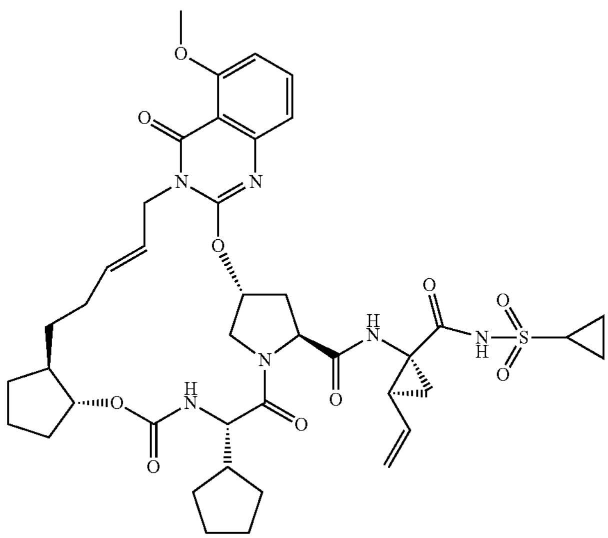 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3cccc(OC)c3c1=O)O2)C(=O)NS(=O)(=O)C1CC1] | (3aR,7S,10S,12R,22E,25aS)-7-cyclopentyl-N-((1R,2S)-1-{[(cyclopropylsulfonyl)amino]carbonyl}-2-vinylcyclopropyl)-18-methoxy-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 821.1 | A1, B7, D8 |
| 54 | 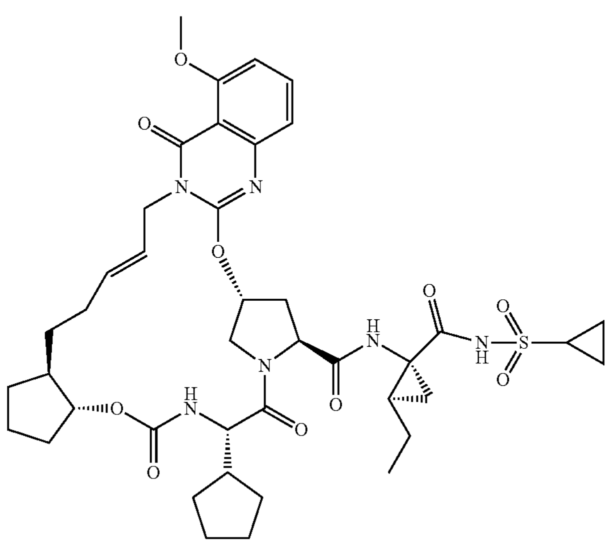 [SMILES: CC[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3cccc(OC)c3c1=O)O2)C(=O)NS(=O)(=O)C1CC1] | (3aR,7S,10S,12R,22E,25aS)-7-cyclopentyl-N-((1R,2R)-1-{[(cyclopropylsulfonyl)amino]carbonyl}-2-ethylcyclopropyl)-18-methoxy-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | 823.2 | A3, B7, D8 |

| Ex. | Structure | Name | LRMS (M + H)+ | Int. |
|---|---|---|---|---|
| 55 | 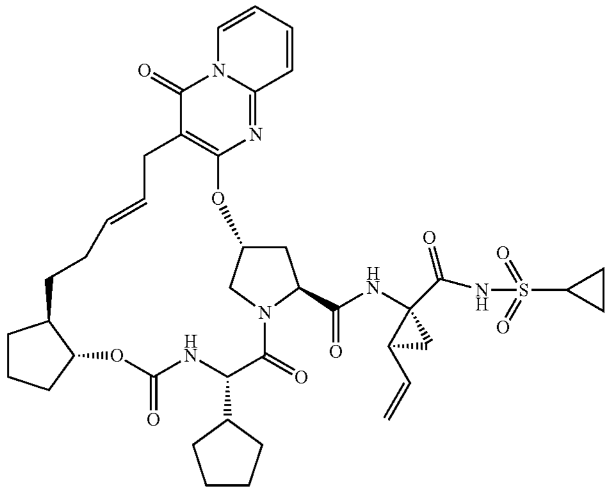 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccn3c1=O)O2)C(=O)NS(=O)(=O)C1CC1] | (3aR,7S,10S,12R,22E,25aS)-7-cyclopentyl-N-((1R,2S)-1-{[(cyclopropylsulfonyl)amino]carbonyl}-2-vinylcyclopropyl)-5,8,20-trioxo-1,2,3,3a,5,6,7,8,11,12,21,24,25,25a-tetradecahydro-10H,20H-9,12-methanocyclopenta[r]pyrido[1',2':1,2]pyrimido[4,5-k][1,10,3,6]dioxadiazacyclononadecine-10-carboxamide | 791.1 | A1, B7, D9 |
| 56 | 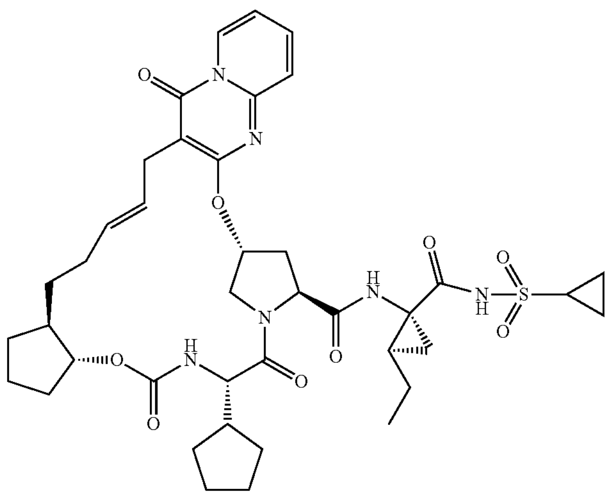 [SMILES: CC[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3ccccn3c1=O)O2)C(=O)NS(=O)(=O)C1CC1] | (3aR,7S,10S,12R,22E,25aS)-7-cyclopentyl-N-((1R,2R)-1-{[(cyclopropylsulfonyl)amino]carbonyl}-2-ethylcyclopropyl)-5,8,20-trioxo-1,2,3,3a,5,6,7,8,11,12,21,24,25,25a-tetradecahydro-10H,20H-9,12-methanocyclopenta[r]pyrido[1',2':1,2]pyrimido[4,5-k][1,10,3,6]dioxadiazacyclononadecine-10-carboxamide | 793.13 | A3, B7, D9 |
| 57 | 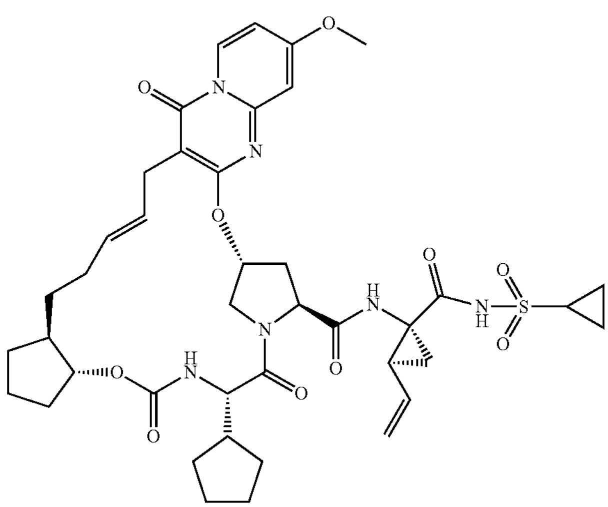 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cc1c(nc3cc(OC)ccn3c1=O)O2)C(=O)NS(=O)(=O)C1CC1] | (3aR,7S,10S,12R,22E,25aS)-7-cyclopentyl-N-((1R,2S)-1-{[(cyclopropylsulfonyl)amino]carbonyl}-2-vinylcylcopropyl)-16-methoxy-5,8,20-trioxo-1,2,3,3a,5,6,7,8,11,12,21,24,25,25a-tetradecahydro-10H,20H-9,12-methanocyclopenta[r]pyrido[1',2':1,2]pyrimido[4,5-k][1,10,3,6]dioxadiazacyclononadecine-10-carboxamide | 821.1 | A1, B7, D10 |

| Ex. | Structure | Name | LRMS (M + H)⁺ | Int. |
|---|---|---|---|---|
| 58 | 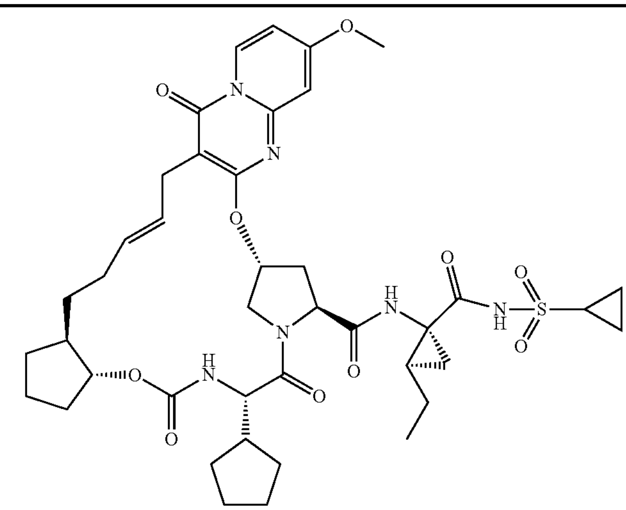 | (3aR,7S,10S,12R,22E,25aS)-7-cyclopentyl-N-((1R,2R)-1-{[(cyclopropylsulfonyl)amino]carbonyl}-2-ethylcyclopropyl)-16-methoxy-5,8,20-trioxo-1,2,3,3a,5,6,7,8,11,12,21,24,25,25a-tetradecahydro-10H,20H-9,12-methanocyclopenta[r]pyrido[1',2':1,2]pyrimido[4,5-k][1,10,3,6]dioxadiazacyclononadecine-10-carboxamide | 823.2 | A3, B7, D10 |

Example 59

(3aR,7S,10S,12R,22E,25aS)-7-cyclopentyl-N-((1R,2S)-1-{[(cyclopropylsulfonyl)amino]carbonyl}-2-vinylcyclopropyl)-5,8,19-trioxo-16-phenyl-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide Step 1: Methyl (3aR,7S,10S,12R,22E,25aS)-16-bromo-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate The title compound was prepared in a similar manner as Example 39 starting from intermediate D2. LCMS (ES+) m/z 671.0 (M+H)+.

91

Step 2: Methyl (3aR,7S,10S,12R,22E,25aS)-7-cyclopentyl-5,8,19-trioxo-16-phenyl-1,2,3,3a,5,6,7,8,11,12,21,24,25,25a-tetradecahydro-10H,19H-9,12-methanocyclopenta[18,19][1,10,3,6,12]dioxatriazacyclononadecino[1,12-b]quinazoline-10-carboxylate

92

Step 3 (3aR,7S,10S,12R,22E,25aS)-7-cyclopentyl-N-((1R,2S)-1-{[(cyclopropylsulfonyl)amino]carbonyl}-2-vinylcyclopropyl)-5,8,19-trioxo-16-phenyl-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide

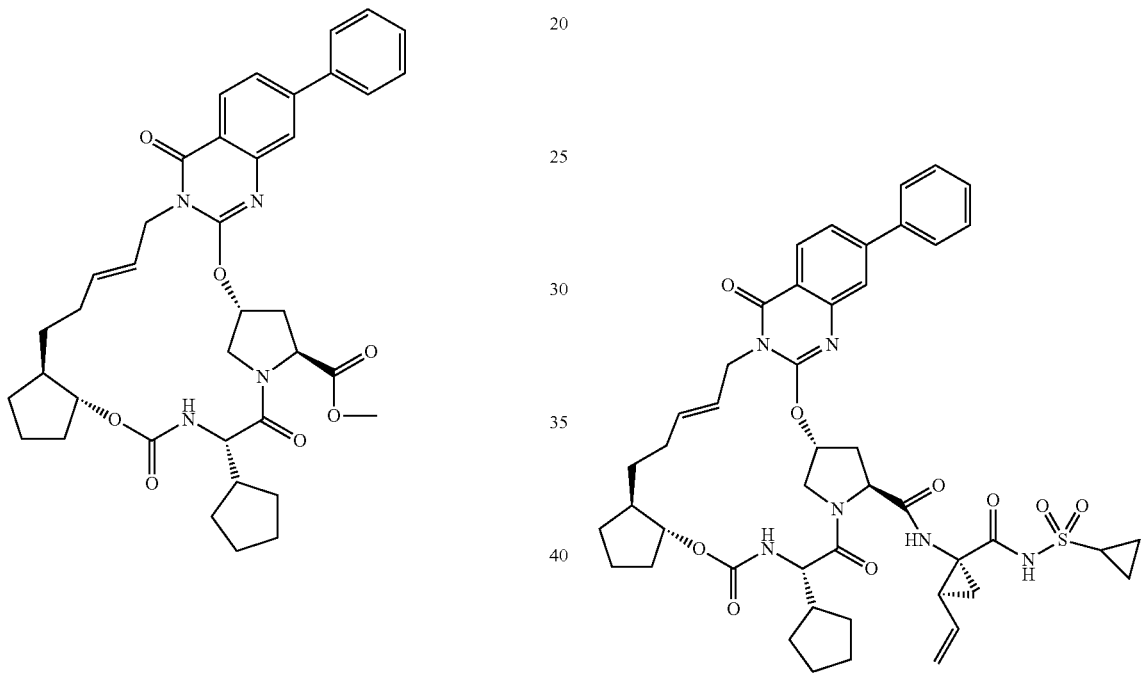

Aqueous sodium carbonate (2 M, 0223 ml, 0.447 mmol) and Pd(Ph₃P)₄ (17.21 mg, 0.015 mmol) were added to a solution of methyl (3aR,7S,10S,12R,22E,25aS)-16-bromo-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate (100 mg, 0.149 mmol) in toluene (1.5 mL) in a sealed tube. Phenylboronic acid (27.2 mg, 0.223 mmol) was added and the mixture heated to 90° C. The reaction was let stir for 2 hours, allowed to cool and diluted with aqueous. KHSO₄. The product was extracted into ethyl acetate, washed with aqueous sodium bicarbonate, dried over sodium sulfate, filtered and concentrated to a foam. The foam was chromatographed on silica using 20-50% ethyl acetate/hexane to give 81 mg foam. LCMS (ES+) m/z 669.0 (M+H)+.

The title compound was prepared in a similar manner as Example 39, utilizing methyl (3aR,7S,10S,12R,22E,25aS)-7-cyclopentyl-5,8,19-trioxo-16-phenyl-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate. LCMS (ES+) m/z 867.37 (M+H)+.

Example 60

(3aR,7S,10S,12R,22E,25aS)-7-cyclopentyl-N-((1R,2R)-1-{[(cyclopropylsulfonyl)amino]carbonyl}-2-ethylcyclopropyl)-5,8,19-trioxo-16-phenyl-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide

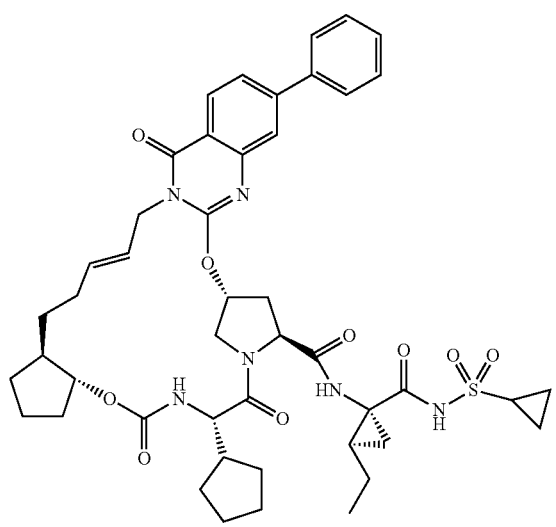 [SMILES: CC[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3cc(-c4ccccc4)ccc3c1=O)O2)C(=O)NS(=O)(=O)C1CC1]

The title compound was prepared in a similar manner as Example 39 utilizing methyl (3aR,7S,10S,12R,22E,25aS)-7-cyclopentyl-5,8,19-trioxo-16-phenyl-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate. LCMS (ES+) m/z 869.39 (M+H)+.

Example 61

(3aR,7S,10S,12R,22E,25aS)-7-cyclopentyl-N-((1R,2S)-1-[(cyclopropylsulfonyl)amino]carbonyl)-2-vinylcyclopropyl)-16-methyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide

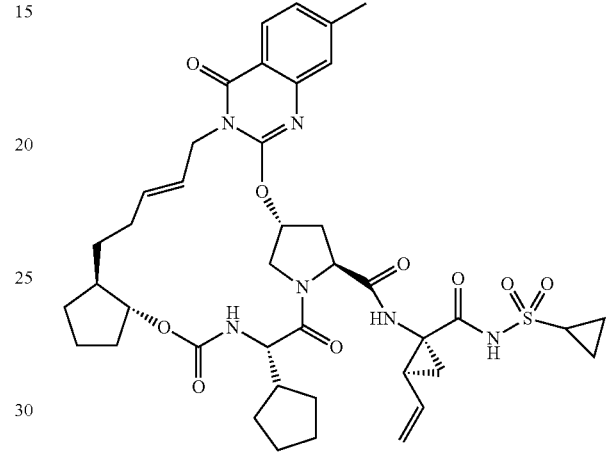

Step 1: Methyl(3aR,7S,10S,12R,22E,25aS)-7-cyclopentyl-16-methyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate

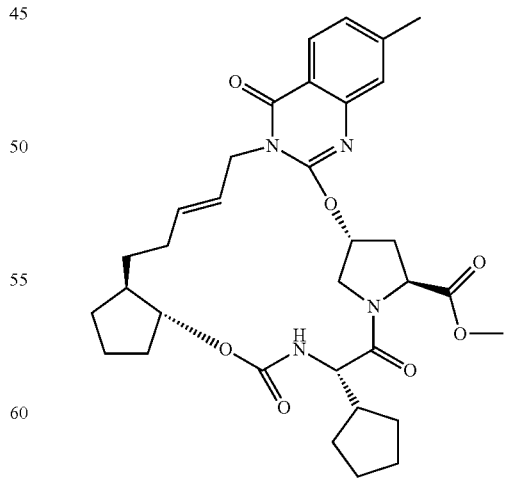

Tetramethyltin (0.041 ml, 0.298 mmol), lithium chloride (50.5 mg, 1.191 mmol), triphenylphosphine (15.62 mg, 0.060 mmol) and bis(triphenylphosphine)palladium(II) chloride (15.68 mg, 0.022 mmol) were added to a nitrogen purged solution of methyl (3aR,7S,10S,12R,22E,25aS)-16-bromo-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate, Example 59 Step 1 (100 mg, 0.149 mmol) in DMF (2 ml). The mixture was heated to 90° C. for 3 hr. The reaction was diluted with aqueous. KHSO$_4$ and product extracted into ethyl acetate. The organic extract was washed with aqueous sodium bicarbonate, dried over sodium sulfate, filtered, concentrated and chromatographed on silica using 20-50% ethyl acetate/hexane to give the title compound as a foam, (74 mg, 82%). LCMS (ES+) m/z 607.3 (M+H)+.

Step 2: (3aR,7S,10S,12R,22E,25aS)-7-cyclopentyl-N-((1R,2S)-1-{[(cyclopropylsulfonyl)amino]carbonyl}-2-vinylcyclopropyl)-16-methyl-5,8,19-trioxo-1,2,3,3a,5,6,7,8,11,12,21,24,25,25a-tetradecahydro-10H,19H-9,12-methanocyclopenta[18,19][1,10,3,6,12]dioxatiazacyclononadecino[11,12-b]quinazoline-10-carboxamide

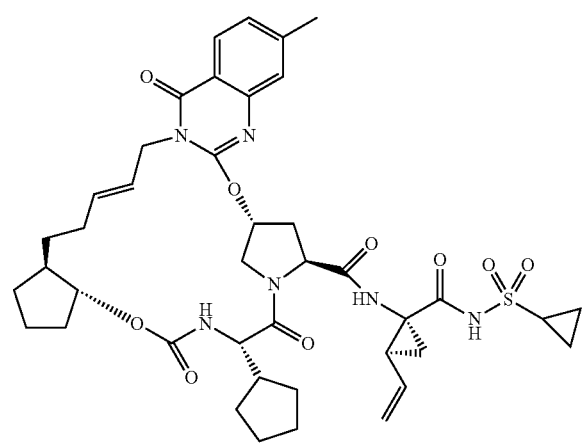 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3cc(C)ccc3c1=O)O2)C(=O)NS(=O)(=O)C1CC1]

The title compound was prepared in a similar manner as Example 39, utilizing methyl(3aR,7S,10S,12R,22E,25aS)-7-cyclopentyl-16-methyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate. LCMS (ES+) m/z 805.3 (M+H)+.

Example 62

(1R,14E,18S,22R,26S,29S)-26-cyclopentyl-N-((1R,2R)-1-{[(cyclopropylsulfonyl)amino]carbonyl}-2-ethyl cyclopropyl)-7-methyl-11,24,27-tri oxo-2,23-dioxa-4,12,25,28-tetraazapentacyclo[26.2.1.0$^{3,12}$.0$^{5,10}$.0$^{18,22}$]hentriaconta-3,5,7,9,14-pentaene-29-carboxamide

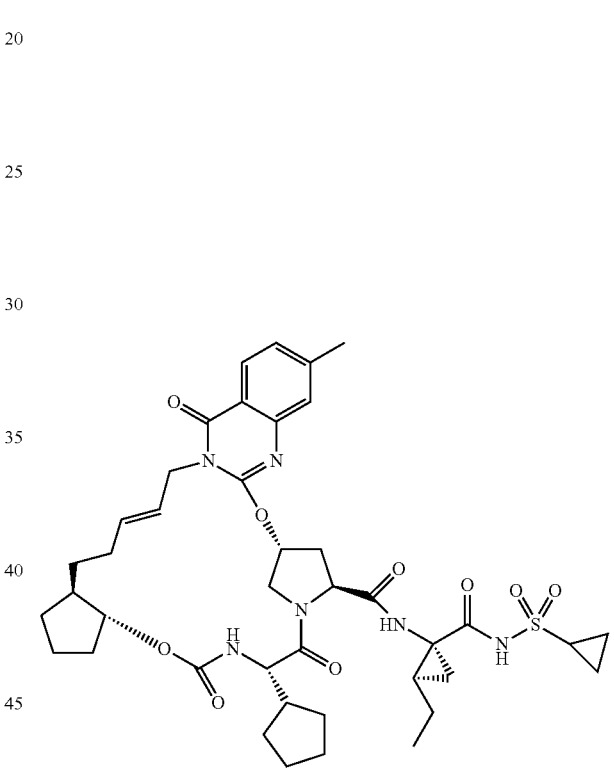

The title compound was prepared in a similar manner as Example 39 utilizing methyl(3aR,7S,10S,12R,22E,25aS)-7-cyclopentyl-16-methyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate. LCMS (ES+) m/z 807.3 (M+H)+.

Example 63

(3aR,7S,10S,12R,22E,25a8)-16-cyano-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide

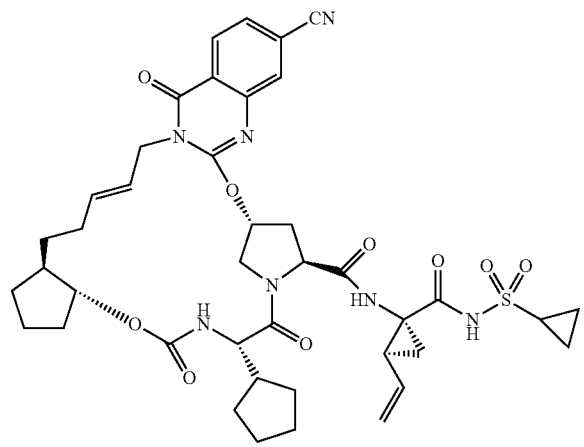 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3cc(C#N)ccc3c1=O)O2)C(=O)NS(=O)(=O)C1CC1]

Step 1: Methyl (3aR,7S,10S,12R,22E,25aS)-16-cyano-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate

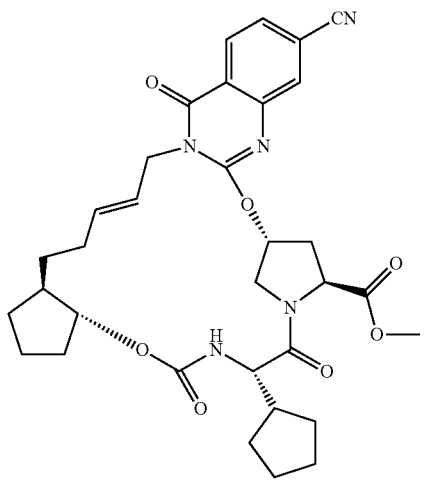 [SMILES: COC(=O)[C@@H]1C[C@@H]2CN1C(=O)[C@H](C1CCCC1)NC(=O)O[C@@H]1CCC[C@H]1CC/C=C/Cn1c(nc3cc(C#N)ccc3c1=O)O2]

Zinc cyanide (5.20 µl, 0.082 mmol) was added to a nitrogen-purged solution of methyl (3aR,7S,10S,12R,22E,25aS)-16-bromo-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate, Example 59 Step 1 (50 mg, 0.074 mmol) in DMF (1 ml), followed by Pd(Ph₃P)₄ (8.60 mg, 7.45 µmol), and the mixture was heated at 100° C. for 3 hrs. The reaction was filtered and purified by reverse phase chromatography to give the title compound. (36 mg, 78%) LCMS (ES+) m/z 618.3 (M+H)+.

Step 2: (3aR,7S,10S,12R,22E,25aS)-16-cyano-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide

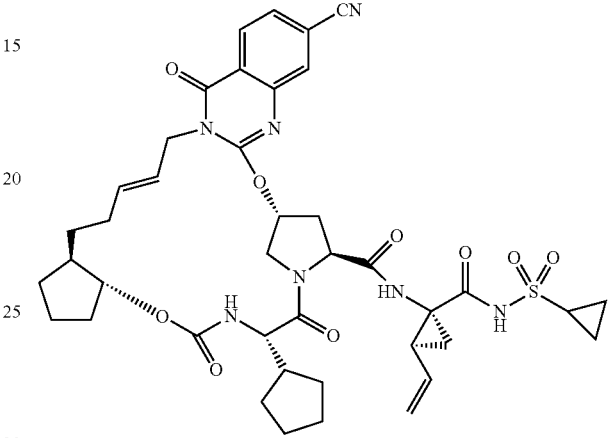

The title compound was prepared in a similar manner as Example 39, utilizing methyl (3aR,7S,10S,12R,22E,25aS)-16-cyano-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate. (ES+) m/z 816.3 (M+H)+.

Example 64

(3aR,7S,10S,12R,22E,25aS)-16-cyano-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide

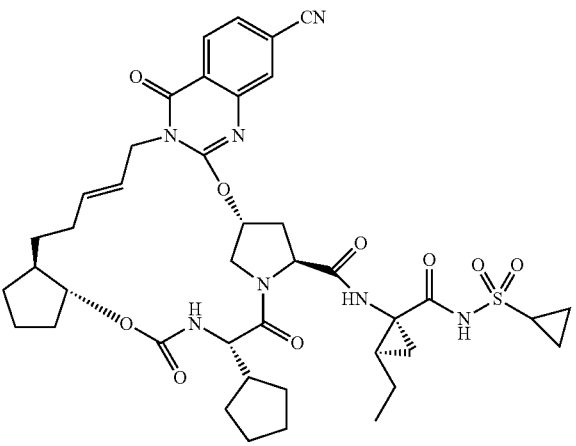 [SMILES: CC[C@@H]1C[C@]1(NC(=O)[C@@H]1C[C@@H]2CN1C(=O)[C@H](C1CCCC1)NC(=O)O[C@@H]1CCC[C@H]1CC/C=C/Cn1c(nc3cc(C#N)ccc3c1=O)O2)C(=O)NS(=O)(=O)C1CC1]

The title compound was prepared in a similar manner as Example 39, utilizing methyl (3aR,7S,10S,12R,22E,25a3)-16-cyano-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate. (ES+) m/z 818.3 (M+H)+.

Example 65

(3aR,7S,10S,12R,25aR)-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide

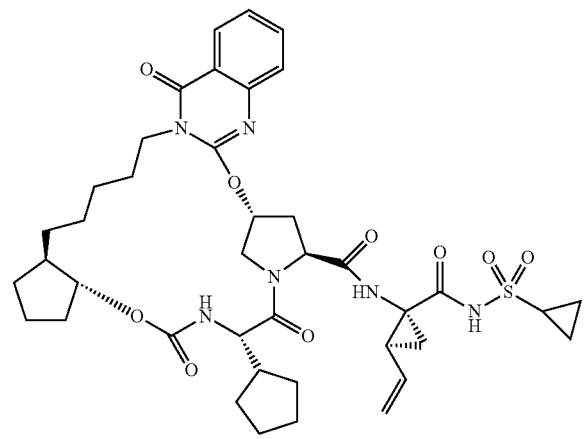 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3ccccc3c1=O)O2)C(=O)NS(=O)(=O)C1CC1]

Step 1: Methyl (3aR,7S,10S,12R,22E,25aS)-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate The title compound was prepared in a similar manner as Example 13, utilizing methyl (4R)-4-[(3-allyl-4-oxo-3,4-dihydroquinazolin-2-yl)oxy]-1-{(2S)-2-[({[(1R,2S)-2-but-3-en-1-ylcyclopentyl]oxy}carbonyl)amino]-2-cyclopentylacetyl}-L-prolinate and 5% Rhodium on carbon as catalyst in 1:1 EtOAc:MeOH. LCMS (ES+) m/z 595.1 (M+H)+.

Step 2: (3aR,7S,10S,12R,22E,25aS)-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylic acid

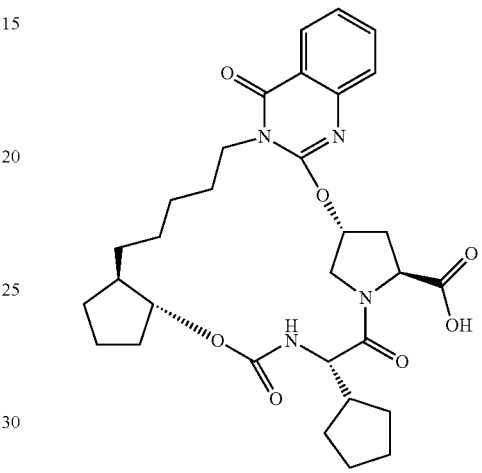

The title compound was prepared in a similar manner as Example 1 Step 5, utilizing methyl (3aR,7S,10S,12R,22E,25aS)-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxylate in 90% yield. LCMS (ES+) m/z 581.1 (M+H)+.

Step 3: (3aR,7S,10S,12R,25aR)-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide

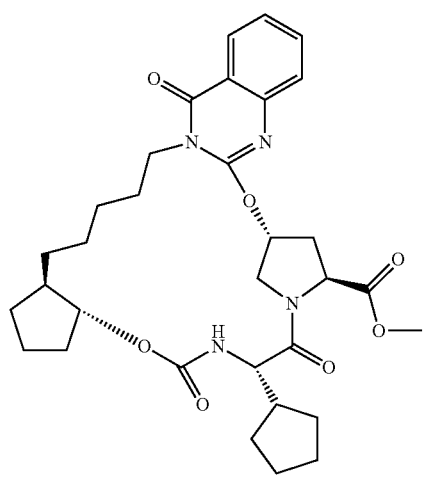 [SMILES: COC(=O)[C@@H]1C[C@@H]2CN1C(=O)[C@H](C1CCCC1)NC(=O)O[C@@H]1CCC[C@H]1CCCCCn1c(nc3ccccc3c1=O)O2]

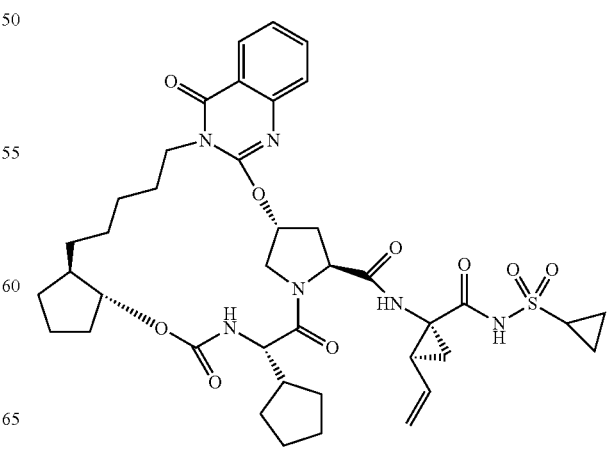

The title compound was prepared in a similar manner as Example 1 Step 6, utilizing (3aR,7S,10S,12R,22E,25aS)-7-cyclopentyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b] quinazoline-10-carboxylic acid in 60% yield. LCMS (ES+) m/z 793.1 (M+H)+.

By following the procedures outlined in Examples 59-65 and using the appropriate A, B, and D intermediates, the following compounds were prepared.

| Ex. | Structure | Name | LRMS (M + H)+ | Int. |
|---|---|---|---|---|
| 66 | 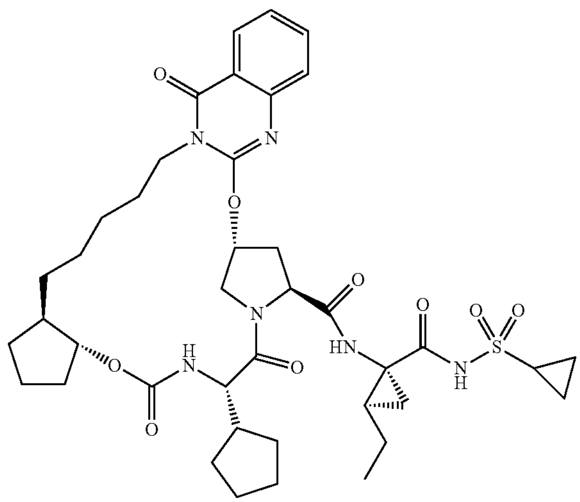 [SMILES: CC[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3ccccc3c1=O)O2)C(=O)NS(=O)(=O)C1CC1] | (3aR,7S,10S,12R,25aR)-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | 795.2 | A3, B7, D1 |
| 67 | 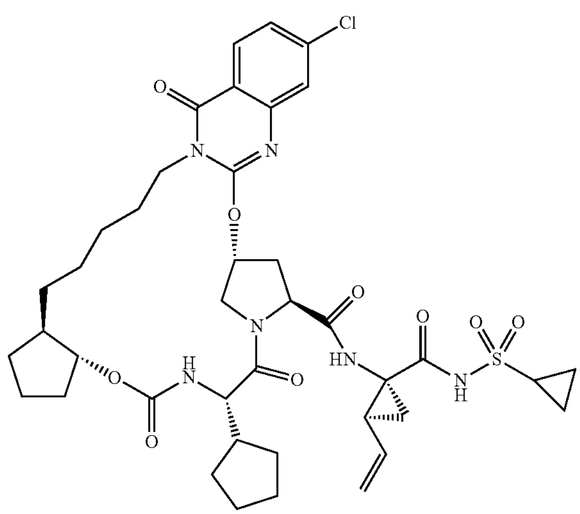 | (3aR,7S,10S,12R,25aR)-16-chloro-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | 827.2 | A1, B7, D3 |

-continued

| Ex. | Structure | Name | LRMS (M + H)+ | Int. |
|---|---|---|---|---|
| 68 | 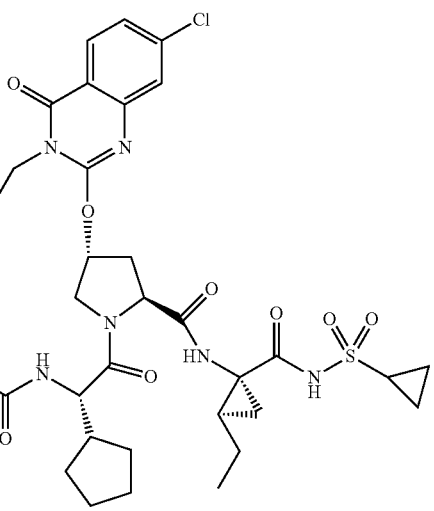 | (3aR,7S,10S,12R,25aR)-16-chloro-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | 829.1 | A3, B7, D3 |
| 69 | 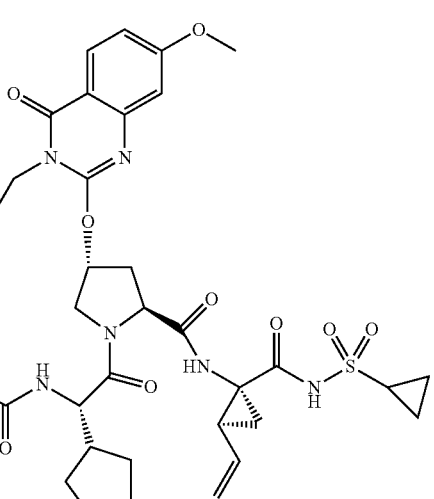 | (3aR,7S,10S,12R,25aR)-7-cyclopentyl-N-((1R,2S)-1-{[(cyclopropylsulfonyl)amino]carbonyl}-2-vinylcyclopropyl)-16-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | 823.2 | A1, B7, D6 |
| 70 | 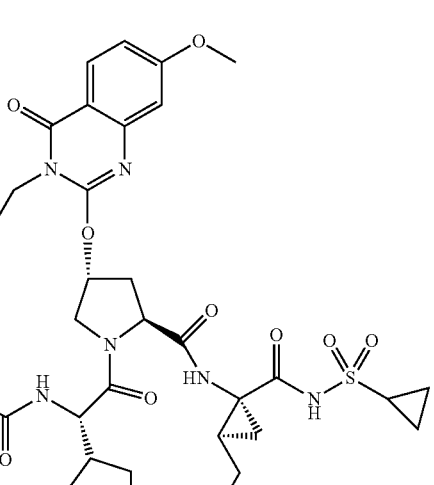 | (3aR,7S,10S,12R,25aR)-7-cyclopentyl-N-((1R,2R)-1-{[(cyclopropylsulfonyl)amino]carbonyl}-2-ethylcyclopropyl)-16-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | 825.1 | A3, B7, D6 |

-continued

| Ex. | Structure | Name | LRMS (M + H)+ | Int. |
|---|---|---|---|---|
| 71 | 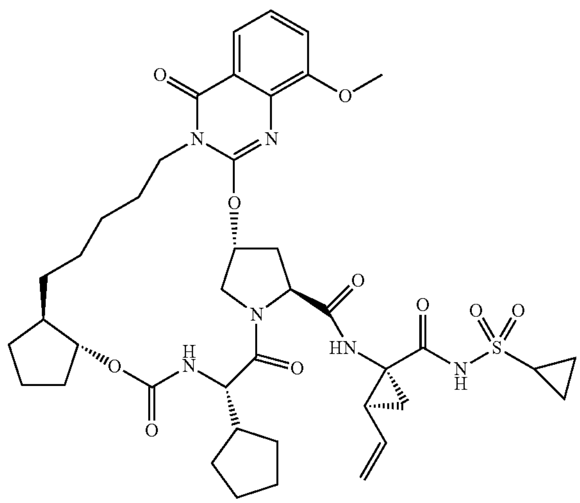 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3c(OC)cccc3c1=O)O2)C(=O)NS(=O)(=O)C1CC1] | (3aR,7S,10S,12R,25aR)-7-cyclopentyl-N-((1R,2S)-1-{[(cyclopropylsulfonyl)amino]carbonyl}-2-vinylcyclopropyl)-15-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | 823.3 | A1, B7, D7 |
| 72 | 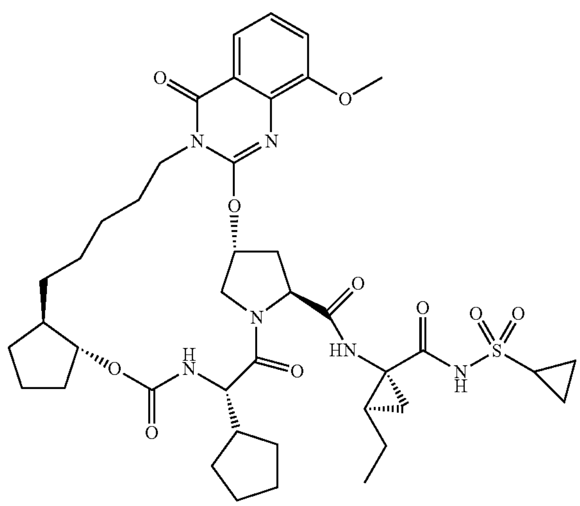 [SMILES: CC[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3c(OC)cccc3c1=O)O2)C(=O)NS(=O)(=O)C1CC1] | (3aR,7S,10S,12R,25aR)-7-cyclopentyl-N-((1R,2R)-1-{[(cyclopropylsulfonyl)amino]carbonyl}-2-ethylcyclopropyl)-15-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | 825.3 | A3, B7, D7 |
| 73 | 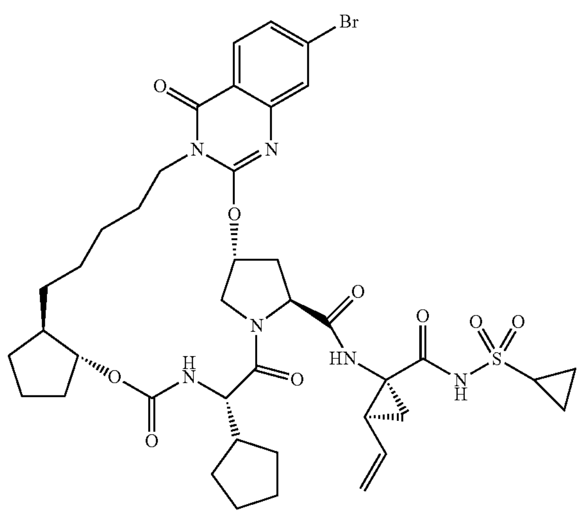 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3cc(Br)ccc3c1=O)O2)C(=O)NS(=O)(=O)C1CC1] | (3aR,7S,10S,12R,25aR)-16-bromo-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | | A1, B7, D2 |

-continued

| Ex. | Structure | Name | LRMS (M + H)+ | Int. |
|---|---|---|---|---|
| 74 | 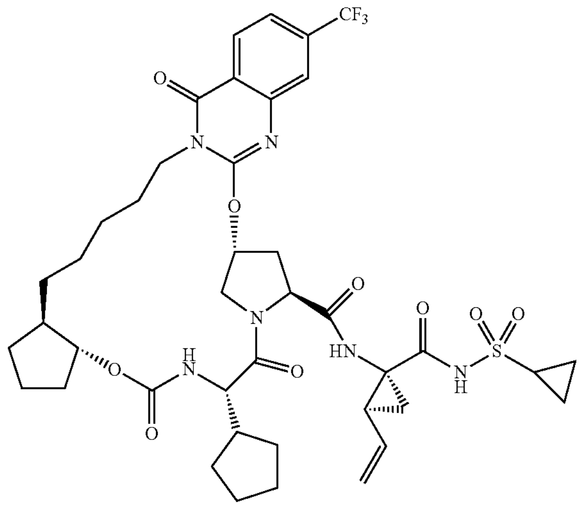 | (3aR,7S,10S,12R,25aR)-7-cyclopentyl-N-((1R,2S)-1-{[(cyclopropylsulfonyl)amino]carbonyl}-2-vinylcyclopropyl)-5,8,19-trioxo-16-(trifluoromethyl)-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | 861.2 | A1, B7, D4 |
| 75 | 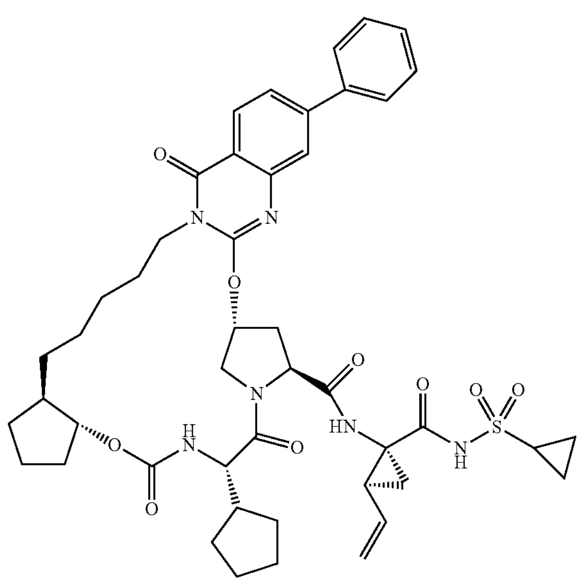 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3cc(-c4ccccc4)ccc3c1=O)O2)C(=O)NS(=O)(=O)C1CC1] | (3aR,7S,10S,12R,25aR)-7-cyclopentyl-N-((1R,2S)-1-{[(cyclopropylsulfonyl)amino]carbonyl}-2-vinylcyclopropyl)-5,8,19-trioxo-16-phenyl-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | | A1, B7, D2 |

| Ex. | Structure | Name | LRMS (M + H)+ | Int. |
|---|---|---|---|---|
| 76 | 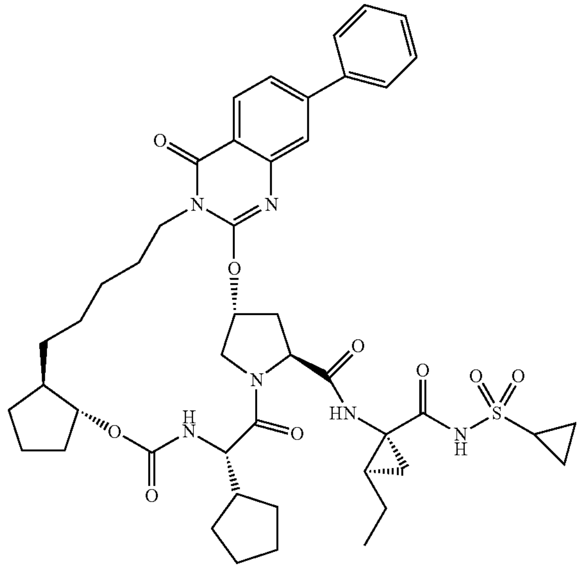 [SMILES: CC[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3cc(-c4ccccc4)ccc3c1=O)O2)C(=O)NS(=O)(=O)C1CC1] | (3aR,7S,10S,12R,25aR)-7-cyclopentyl-N-((1R,2R)-1-{[(cyclopropylsulfonyl)amino]carbonyl}-2-ethylcyclopropyl)-5,8,19-trioxo-16-phenyl-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | | A3, B7, D2 |
| 77 | 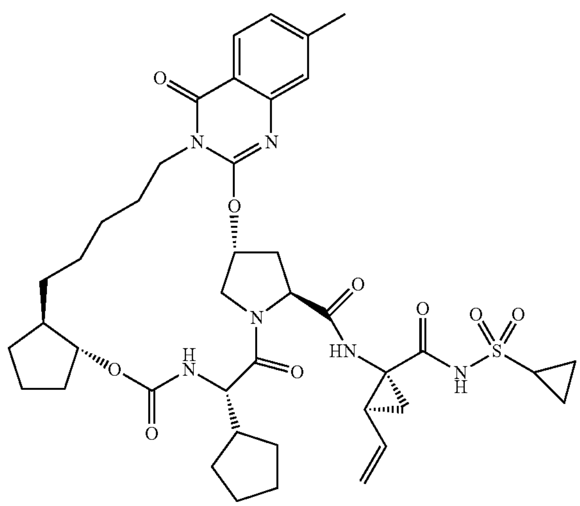 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3cc(C)ccc3c1=O)O2)C(=O)NS(=O)(=O)C1CC1] | (3aR,7S,10S,12R,25aR)-7-cyclopentyl-N-((1R,2S)-1-{[(cyclopropylsulfonyl)amino]carbonyl}-2-vinylcyclopropyl)-16-methyl-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | 807.2 | A1, B7, D2 |
| 78 | 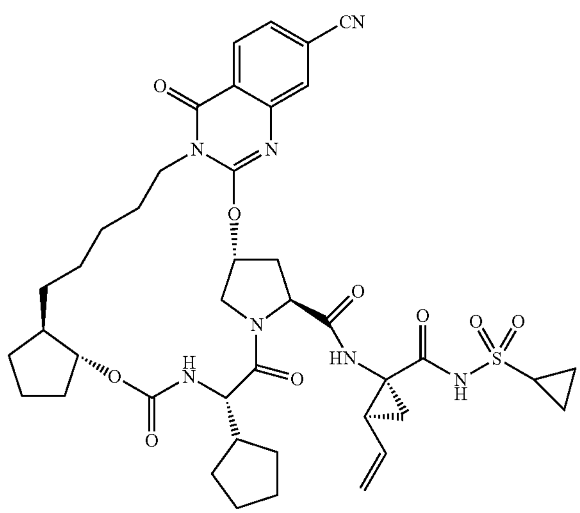 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3cc(C#N)ccc3c1=O)O2)C(=O)NS(=O)(=O)C1CC1] | (3aR,7S,10S,12R,25aR)-16-cyano-7-cyclopentyl-N-((1R,2S)-1-{[(cycyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | 818.2 | A1, B7, D2 |

| Ex. | Structure | Name | LRMS (M + H)+ | Int. |
|---|---|---|---|---|
| 79 | 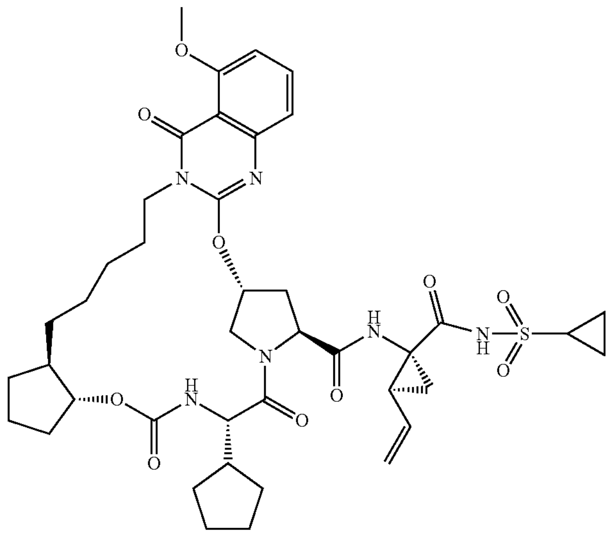 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3cccc(OC)c3c1=O)O2)C(=O)NS(=O)(=O)C1CC1] | (3aR,7S,10S,12R,25aR)-7-cyclopentyl-N-((1R,2S)-1-{[(cyclopropylsulfonyl)amino]carbonyl}-2-vinylcyclopropyl)-18-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | 823.2 | A1, B7, D8 |
| 80 | 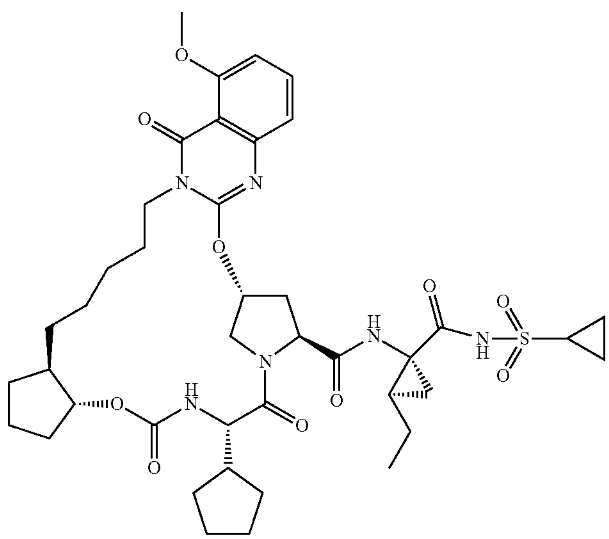 [SMILES: CC[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3cccc(OC)c3c1=O)O2)C(=O)NS(=O)(=O)C1CC1] | (3aR,7S,10S,12R,25aR)-7-cyclopentyl-N-((1R,2R)-1-{[(cyclopropylsulfonyl)amino]carbonyl}-2-ethylcyclopropyl)-18-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | 825.2 | A3, B7, D8 |
| 85 | 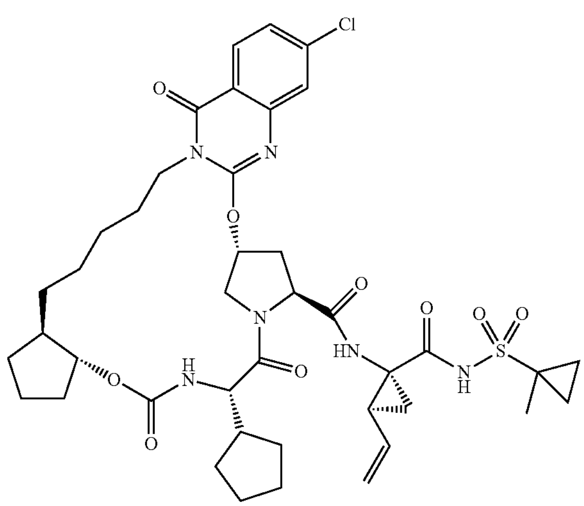 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3cc(Cl)ccc3c1=O)O2)C(=O)NS(=O)(=O)C1(C)CC1] | (1R,18R,22R,26S,29S)-7-chloro-26-cyclopentyl-N-[(1R,2S)-1-({[(1-methylcyclopropyl)sulfonyl]amino}carbonyl)-2-vinylcyclopropyl]-11,24,27-trioxo-2,23-dioxa-4,12,25,28-tetraazapentacyclo[26.2.1.0$^{3,12}$.0$^{5,10}$.0$^{18,22}$]hentriaconta-3,5,7,9-tetraene-29-carboxamide | 841.3 | A13, B7, D3 |

| Ex. | Structure | Name | LRMS (M + H)+ | Int. |
|---|---|---|---|---|
| 86 | 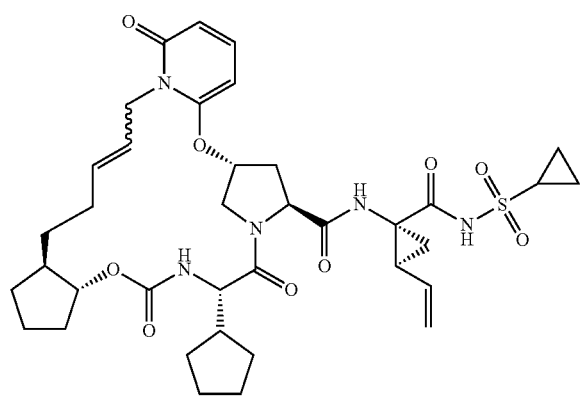 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCC=CCn1c(cccc1=O)O2)C(=O)NS(=O)(=O)C1CC1] | (1R,18R,22R,26S,29S)-26-cyclopentyl-7-methoxy-N-[(1R,2S)-1-({[(1-methylcyclopropyl)sulfonyl]amino}carbonyl)-2-vinylcyclopropyl]-11,24,27-trioxo-2,23-dioxa-4,12,25,28-tetraazapentacyclo[26.2.1.0$^{3,12}$.0$^{5,10}$.0$^{18,22}$]hentriaconta-3,5,7,9-tetraene-29-carboxamide | 837.3 | A13, B7, D6 |

Example 81

(1R,10E, and 10Z,14S,18R,22S,25S)-22-Cyclopentyl-N-((1R,2S)-1-{[(cyclopropyl-sulfonyl)amino]carbonyl}-2-vinylcyclopropyl)-7,20,23-trioxo-2,19-dioxa-8,21,24-tri azatetracyclo[22.2.1.0$^{3,8}$.0$^{14,18}$]heptacosa-3,5,10-triene-25-carboxamide

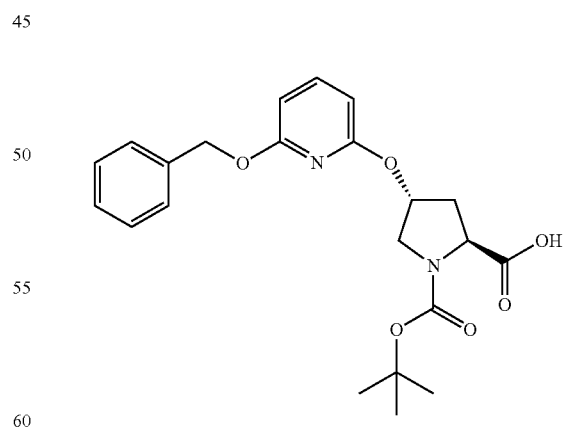

Step 1: 2-(Benzyloxy)-6-fluoropyridine

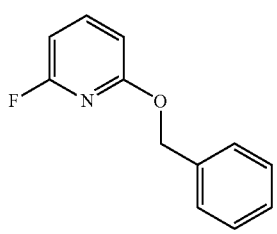 [SMILES: Fc1cccc(OCc2ccccc2)n1]

An oven-dried 3-neck 2 L round bottom flask under nitrogen was charged with benzyl alcohol (9.04 ml, 87 mmol) and tetrahydrofuran (75 ml). Attached an addition funnel containing a solution of 2,6-difluoropyridine (10.00 g, 87 mmol) in tetrahydrofuran (30 ml). Sodium hydride (3.82 g, 96 mmol) was added in small portions with stirring. Heated in a 50° C. oil bath for 45 minutes; cooled to room temperature. Added contents of addition funnel dropwise. After 18 hours poured into water. Extracted three times with ethyl acetate, washed combined organic portions with brine, dried with anhydrous magnesium sulfate, filtered and rotary evaporated filtrate. The crude product was subjected to flash column chromatography eluting with hexane. Evaporation of fractions gave the title compound as a colorless oil. (17.70 g, 87 mmol, 100% yield). LCMS (ES+) m/z 204.3 (M+H)+.

Step 2: (4R)-4-{[6-(Benzyloxy)pyridin-2-yl]oxy}-1-(tert-butoxycarbonyl)-L-proline A 500 mL 3-neck round bottom flask under nitrogen was charged with Boc-L-4-hydroxyproline (Chem Impex) (2.00 g, 8.65 mmol) and DMSO (80 ml). Attached an addition funnel containing a solution of the product of Step 1 (1.758 g, 8.65 mmol) in DMSO (10 ml). Cooled reaction in an ice bath to +18° C. Added potassium-t-butoxide (2.91 g, 25.9 mmol)

slowly keeping the internal temperature<20° C. Stirred 45 minutes at room temperature. Cooled to 15° C. Added contents of addition funnel dropwise. Warmed to room temperature. Stirred 1.5 hours. Poured into 2.5% potassium bisulfate. Extracted three times with ethyl acetate, washed combined organic portions with water then brine, dried with anhydrous magnesium sulfate, filtered and rotary evaporated filtrate to give the title compound as a white foam. (3.58 g, 8.65 mmol, 100% yield). LCMS (ES+) m/z 415.3 (M+H)$^+$.

Step 3: 1-tert-Butyl 2-methyl (2S,4R)-4-{[6-(benzyloxy)pyridin-2-yl]oxy}pyrrolidine-1,2-dicarboxylate

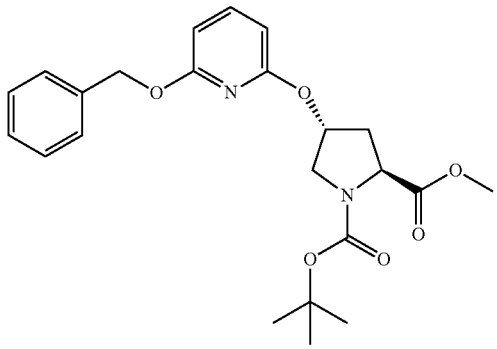 [SMILES: COC(=O)[C@@H]1C[C@@H](Oc2cccc(OCc3ccccc3)n2)CN1C(=O)OC(C)(C)C]

A 500 mL round bottom flask under nitrogen was charged with the product of Step 2 (7.17 g, 17.30 mmol), methanol (50 ml), and dichloromethane (50 ml). Attached an addition funnel containing trimethylsilyldiazomethane in diethyl ether (2.0M) (25.9 ml, 51.9 mmol). Cooled reaction flask in an ice bath. Added contents of addition funnel dropwise. Bubbles. HPLC/MS looks good after 0.5 hours. Quenched by dropwise addition of 2.5% potassium bisulfate. Evaporated to remove methanol. Added water. Extracted three times with ethyl acetate, dried with anhydrous magnesium sulfate, filtered and rotary evaporated filtrate. Subjected to flash column chromatography eluting with 80 hexane/20 ethyl acetate. Evaporation of fractions containing product gave the title compound as a colorless oil. (6.50 g, 15.17 mmol, 88% yield). LCMS (ES+) m/z 429.3 (M+H)$^+$.

Step 4: 1-tert-Butyl 2-methyl (2S,4R)-4-[(6-hydroxypyridin-2-yl)oxy]pyrrolidine-1,2-dicarboxylate

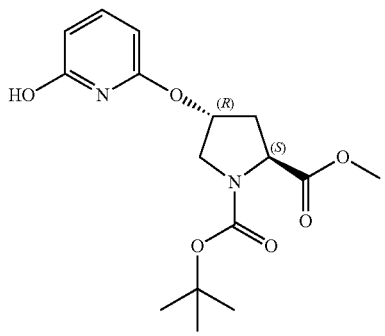

A Parr jar was charged with the product of Step 3 (6.50 g, 15.17 mmol), EtOH (100 ml), and 10% Pd/C (0.250 g, 2.349 mmol). Hydrogenated at 48 psi. Reaction complete after 18 hours. Filtered through celite. Evaporation of the filtrate gave the title compound as a white foam. (4.95 g, 14.63 mmol, 96% yield). LCMS (ES+) m/z 339.3 (M+H)$^+$.

Step 5: 1-tert-Butyl 2-methyl (2S,4R)-4-{[6-(allyloxy)pyridin-2-yl]oxy}pyrrolidine-1,2-dicarboxylate

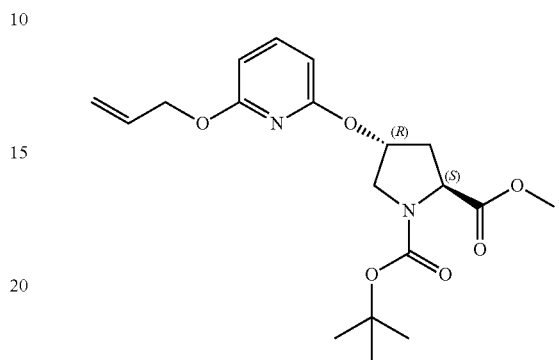

A 500 mL round bottom flask under nitrogen was charged with the product of Step 4 (4.95 g, 14.63 mmol), tetrahydrofuran (200 ml), allyl bromide (2.53 ml, 29.3 mmol), and cesium carbonate (4.77 g, 14.63 mmol). Heated in a 60° C. oil bath for 18 hours. HPLC/MS o.k. Cooled. Evaporated. Added 2.5% potassium bisulfate. Extracted three times with ethyl acetate, washed combined organic portions with brine, dried with anhydrous magnesium sulfate, filtered and rotary evaporated filtrate. Subjected to flash column chromatography eluting with 70 hexane/30 ethyl acetate. Evaporation of fractions containing product gave the title compound as a pale oil. (4.56 g, 12.05 mmol, 82% yield). LCMS (ES+) m/z 379.3 (M+H)$^+$.

Step 6: 1-tert-Butyl 2-methyl (2S,4R)-4-[(1-allyl-6-oxo-1,6-dihydropyridin-2-yl)oxy]pyrrolidine-1,2-dicarboxylate

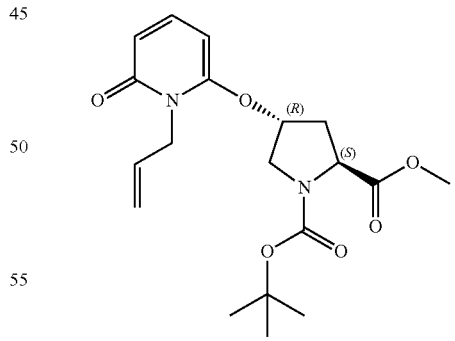

An oven-dried 100 mL Kjeldahl Flask under nitrogen was charged with the product of Step 5 (2.82 g, 7.45 mmol) and toluene (15 ml). Degassed 5 minutes with nitrogen. Added tetrakis(triphenylphosphine)palladium(0) (0.431 g, 0.373 mmol). Heated in a 60° C. oil bath for 1 hour. HPLC/MS shows product. HPLC/MS looks good after 2 hours. Cooled. Evaporated. Subjected to flash column chromatography eluting with 99 methylene chloride/1 methanol. Evaporation of fractions containing product gave the title compound as an oil/foam. (1.91 g, 5.05 mmol, 67.7% yield). LCMS (ES+) m/z 379.3 (M+H)+.

Step 7: (2S,4R)-4-[(1-Allyl-6-oxo-1,6-dihydropyridin-2-yl)oxy]-2-(methoxycarbonyl)-pyrrolidinium chloride

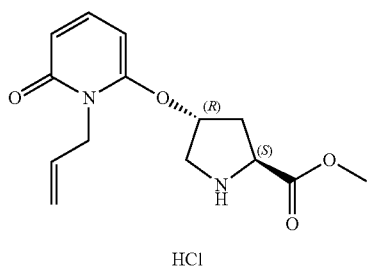

A 100 mL round bottom flask was charged with the product of Step 6 (1.91 g, 5.05 mmol). Added HCl (4.0M in dioxane) (30 mL, 120 mmol). Stirred at room temperature for 1 hour. Evaporated. Added ethanol. Evaporated. Repeated. The title compound remained as a pale foam. (1.59 g, 5.05 mmol, 100% yield). LCMS (ES+) m/z 279.3 (M+H)+.

Step 8: Methyl (4R)-4-[(1-allyl-6-oxo-1,6-dihydropyridin-2-yl)oxy]-1-{(2S)-2-[({[(1R,2S)-2-but-3-en-1-ylcyclopentyl]oxy}carbonyl)amino]-2-cyclopentylacetyl}-L-prolinate

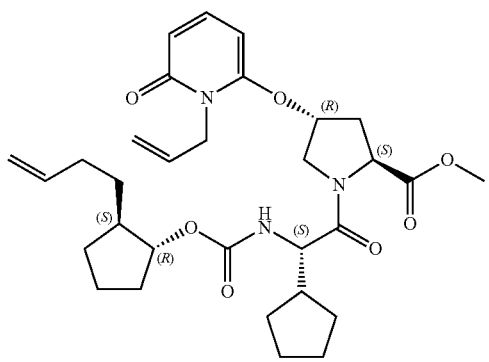

The title compound was prepared in a similar manner as Example 1 Step 3, utilizing (2S,4R)-4-[(1-allyl-6-oxo-1,6-dihydropyridin-2-yl)oxy]-2-(methoxycarbonyl)-pyrrolidinium chloride and Intermediate B7 in 71% yield. LCMS (ES+) m/z 570.3 (M+H)+.

Step 9: Methyl (1R,10E, and 10Z,14S,18R,22S,25S)-22-cyclopentyl-7,20,23-trioxo-2,19-dioxa-8,21,24-triazatetracyclo[22.2.1.0³,⁸.0¹⁴,¹⁸]heptacosa-3,5,10-triene-25-carboxylate

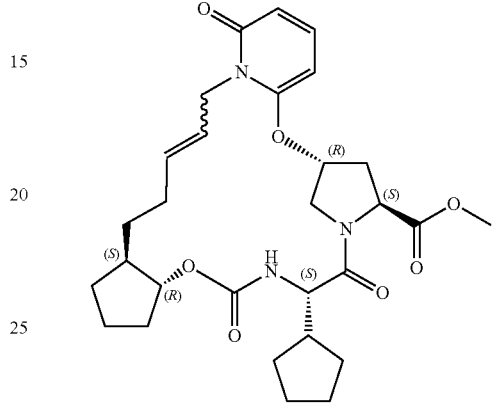

The title compound was prepared in a similar manner as Example 1 Step 4, utilizing methyl (4R)-4-[(1-allyl-6-oxo-1,6-dihydropyridin-2-yl)oxy]-1-{(2S)-2-[({[(1R,2S)-2-but-3-en-1-ylcyclopentyl]oxy}carbonyl)amino]-2-cyclopentylacetyl}-L-prolinate in 100% yield. LCMS (ES+) m/z 542.3 (M+H)+.

Step 10: (1R,10E, and 10Z,14S,18R,22S,25S)-22-Cyclopentyl-7,20,23-trioxo-2,19-dioxa-8,21,24-triazatetracyclo[22.2.1.0³,⁸.0¹⁴,¹⁸]heptacosa-3,5,10-triene-25-carboxylic acid

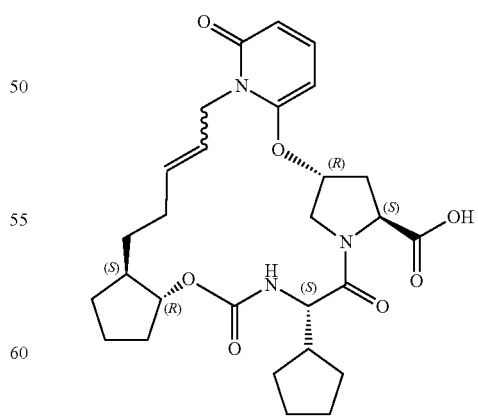

The title compound was prepared in a similar manner as Example 1 Step 5, utilizing methyl (1R,10E, and 10Z,14S, 18R,22S,25S)-22-cyclopentyl-7,20,23-trioxo-2,19-dioxa-8, 21,24-triazatetracyclo[22.2.1.0$^{3,8}$.0$^{14,18}$]heptacosa-3,5,10-triene-25-carboxylate in 83% yield. LCMS (ES+) m/z 528.3 (M+H)$^+$.

Step 11: (1R,10E, and 10Z,14S,18R,22S,25S)-22-Cyclopentyl-N-((1R,1S)-1-{[(cyclo-propylsulfonyl)amino]carbonyl}-2-vinylcyclopropyl)-7,20,23-trioxo-2,19-dioxa-8,21,24-triazatetracyclo[22.2.1.0$^{3,8}$.0$^{14,18}$]heptacosa-3,5,10-triene-25-carboxamide

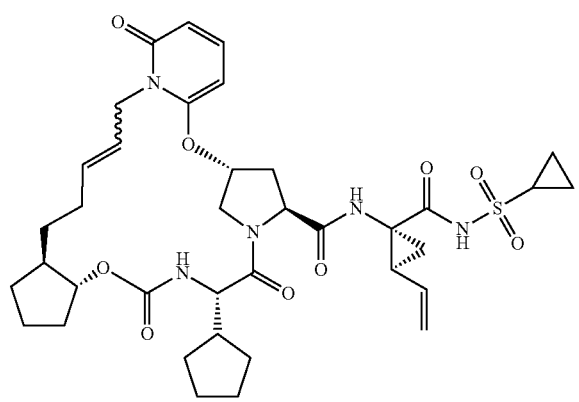 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCC=CCn1c(cccc1=O)O2)C(=O)NS(=O)(=O)C1CC1]

The title compound was prepared in a similar manner as Example 1 Step 6, utilizing (1R,10E, and 10Z,14S,18R,22S,25S)-22-Cyclopentyl-7,20,23-trioxo-2,19-dioxa-8,21,24-triazatetracyclo[22.2.1.0$^{3,8}$.0$^{14,18}$]heptacosa-3,5,10-triene-25-carboxylic acid to give a 31% yield. LCMS (ES+) m/z 740.3 (M+H)$^+$.

Example 82

(1R,14R,18R,22S,25S)-22-cyclopentyl-N-((1R,2S)-1-{[(cyclopropylsulfonyl)amino]carbonyl}-2-vinylcyclopropyl)-7,20,23-tri oxo-2,19-dioxa-8,21,24-triazatetracyclo[22.2.1.0$^{3,8}$.0$^{14,18}$]heptacosa-3,5-diene-25-carboxamide

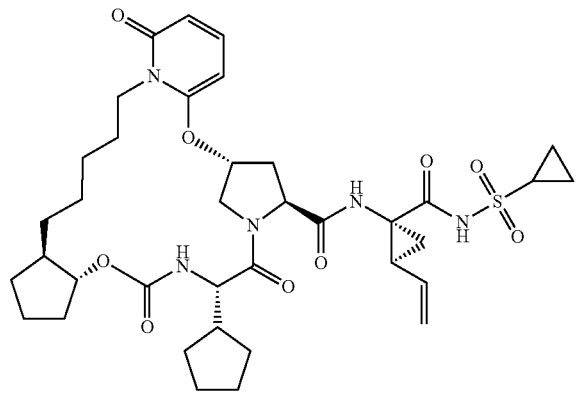 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(cccc1=O)O2)C(=O)NS(=O)(=O)C1CC1]

Step 1: Methyl (1R,14R,18R,22S,25S)-22-cyclopentyl-7,20,23-trioxo-2,19-dioxa-8,21,24-triazatetracyclo[22.2.1.0$^{3,8}$.0$^{14,18}$]heptacosa-3,5-diene-25-carboxylate

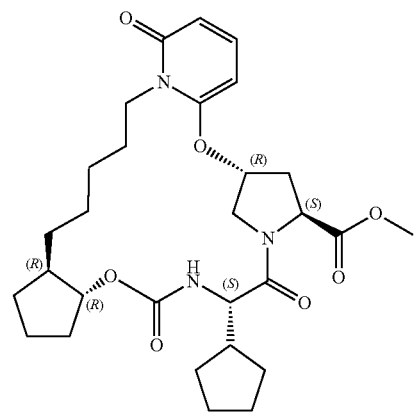

The title compound was prepared in a similar manner as Example 13 Step 1, utilizing methyl (1R,10E, and 10Z,14S,18R,22S,25S)-22-cyclopentyl-7,20,23-trioxo-2,19-dioxa-8,21,24-triazatetracyclo[22.2.1.0$^{3,8}$.0$^{14,18}$]heptacosa-3,5,10-triene-25-carboxylate and replacing THF with ethanol as the solvent to give a 94% yield. LCMS (ES+) m/z 544.3 (M+H)$^+$.

Step 2: (1R,14R,18R,22S,25S)-22-Cyclopentyl-7,20,23-trioxo-2,19-dioxa-8,21,24-triazatetracyclo[22.2.1.0$^{3,8}$.0$^{14,18}$]heptacosa-3,5-diene-25-carboxylic acid

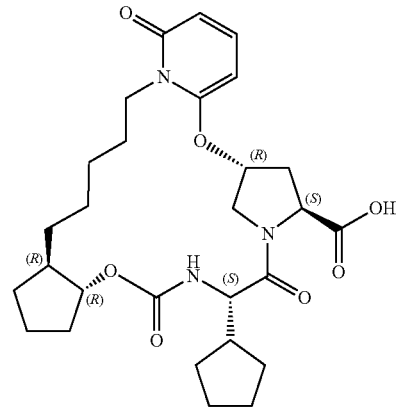

The title compound was prepared in a similar manner as Example 1 Step 5, utilizing methyl (1R,14R,18R,22S,25S)-22-cyclopentyl-7,20,23-trioxo-2,19-dioxa-8,21,24-triazatetracyclo[22.2.1.0³,⁸.0¹⁴,¹⁸]heptacosa-3,5-diene-25-carboxylate to give a 100% yield. LCMS (ES+) m/z 530.3 (M+H)⁺.

Step 3: (1R,14R,18R,22S,25S)-22-cyclopentyl-N-((1R,2S)-1-{[(cyclopropylsulfonyl)-amino]carbonyl}-2-vinylcyclopropyl)-7,20,23-trioxo-2,19-dioxa-8,21,24-triazatetracyclo[22.2.1.0³,⁸.0¹⁴,¹⁸]heptacosa-3,5-diene-25-carboxamide

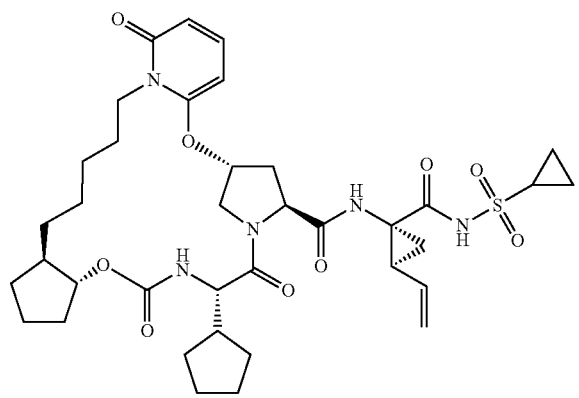 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(cccc1=O)O2)C(=O)NS(=O)(=O)C1CC1]

The title compound was prepared in a similar manner as Example 1 Step 6, utilizing (1R,14R,18R,22S,25S)-22-Cyclopentyl-7,20,23-trioxo-2,19-dioxa-8,21,24-triazatetracyclo[22.2.1.0³,⁸.0¹⁴,¹⁸]heptacosa-3,5-diene-25-carboxylic acid to give a 61% yield. LCMS (ES+) m/z 742.3 (M+H)⁺.

Example 83

(1R,14R,18R,22S,25S)-6-bromo-22-cyclopentyl-N-((1R,2S)-1-{[(cyclopropylsulfonyl)amino]carbonyl}-2-vinylcyclopropyl)-7,20,23-trioxo-2,19-dioxa-8,21,24-triazatetracyclo[22.2.1.0³,⁸.0¹⁴,¹⁸]heptacosa-3,5-diene-25-carboxamide

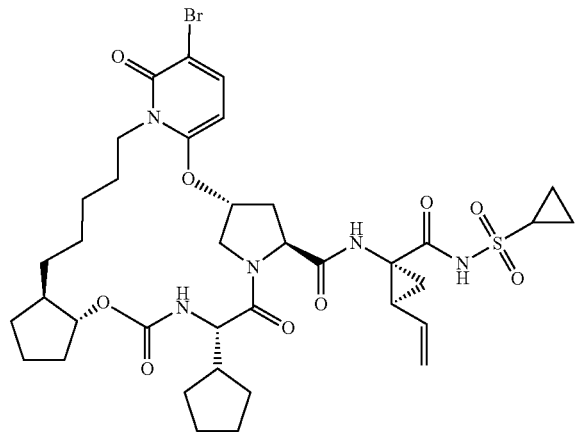 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(ccc(Br)c1=O)O2)C(=O)NS(=O)(=O)C1CC1]

Step 1: Methyl (1R,14R,18R,22S,25S)-6-bromo-22-cyclopentyl-7,20,23-trioxo-2,19-dioxa-8,21,24-triazatetracyclo[22.2.1.0³,⁸.0¹⁴,¹⁸]heptacosa-3,5-diene-25-carboxylate

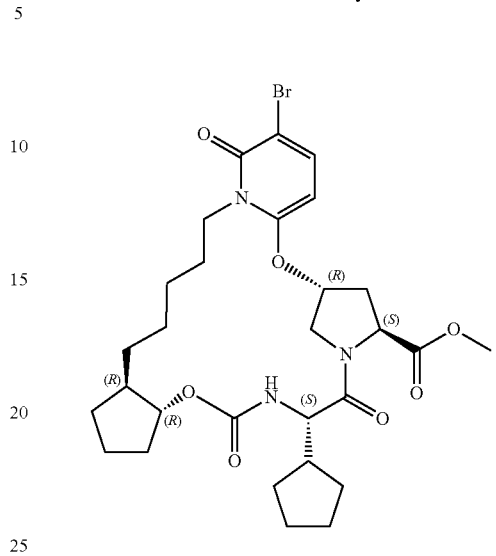

A 25 mL round bottom flask under nitrogen was charged with the product of Example 82 Step 1 (238 mg, 0.438 mmol), NBS (39.0 mg, 0.219 mmol), and acetonitrile (15 ml). Stirred at room temperature 10 minutes. HPLC/MS shows mainly desired; little starting material. Added an additional 10 mg NBS. Still a little starting material remaining. Added another 10 mg NES. HPLC/MS looks good. Cooled. Evaporated. Subjected to ISCO chromatography eluting with a hexane/ethyl acetate gradient. Evaporated fractions containing product to give the title compound as a white solid. (224 mg, 0.360 mmol, 82% yield). LCMS (ES+) m/z 623.3 (M+H)⁺.

Step 2: (1R,14R,18R,22S,25S)-6-bromo-22-cyclopentyl-7,20,23-trioxo-2,19-dioxa-8,21,24-triazatetracyclo[22.2.1.0³,⁸.0¹⁴,¹⁸]heptacosa-3,5-diene-25-carboxylic acid

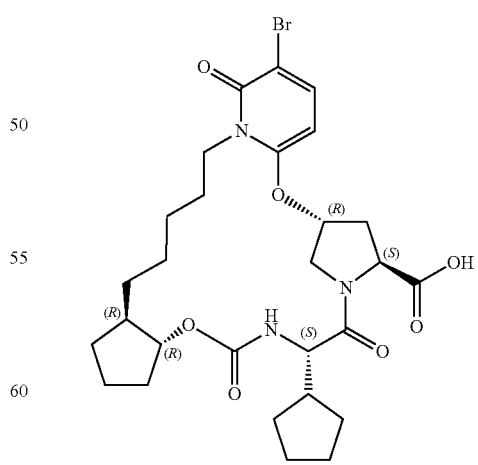

The title compound was prepared in a similar manner as Example 1 Step 5, utilizing methyl (1R,14R,18R,22S,25S)-6-bromo-22-cyclopentyl-7,20,23-trioxo-2,19-dioxa-8,21, 24-triazatetracyclo[22.2.1.0³,⁸.0¹⁴,¹⁸]heptacosa-3,5-diene-25-carboxylate to give a 100% yield. LCMS (ES+) m/z 609.8 (M+H)⁺.

Step 3: (1R,14R,18R,22S,25S)-6-bromo-22-cyclopentyl-N-((1R,2S)-1-{[(cyclopropylsulfonyl)amino]carbonyl}-2-vinylcyclopropyl)-7,20,23-trioxo-2,19-dioxa-8,21,24-triazatetracyclo[22.2.1.0³,⁸.0¹⁴,¹⁸]heptacosa-3,5-diene-25-carboxamide

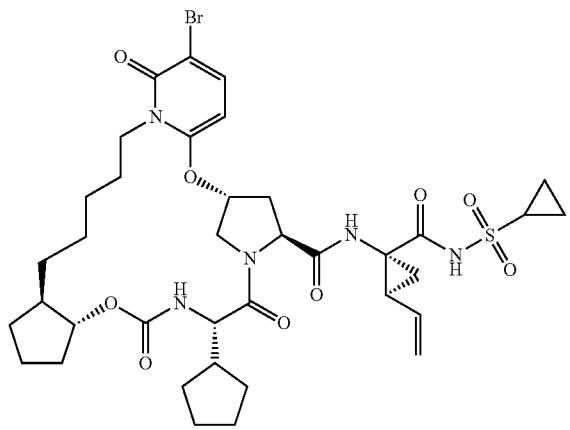 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(ccc(Br)c1=O)O2)C(=O)NS(=O)(=O)C1CC1]

The title compound was prepared in a similar manner as Example 1 Step 6, utilizing (1R,14R,18R,22S,25S)-6-bromo-22-cyclopentyl-7,20,23-trioxo-2,19-dioxa-8,21,24-triazatetracyclo[22.2.1.0³,⁸.0¹⁴,¹⁸]heptacosa-3,5-diene-25-carboxylic acid to give a 49% yield. LCMS (ES+) m/z, 821.3 (M+H)⁺.

Example 84

(1R,14R,18R,22S,25S)-22-cyclopentyl-N-((1R,2S)-1-{[(cyclopropylsulfonyl)amino]carbonyl}-2-vinylcyclopropyl)-7,20,23-trioxo-6-phenyl-2,19-dioxa-8,21,24-triazatetracyclo[22.2.1.0³,⁸.0¹⁴,¹⁸]heptacosa-3,5-diene-25-carboxamide

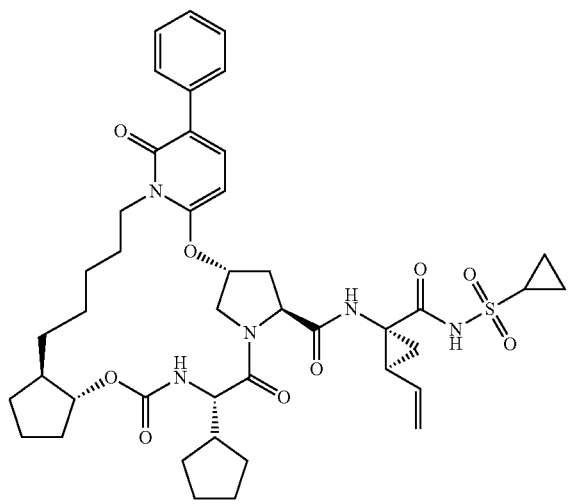 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(ccc(-c3ccccc3)c1=O)O2)C(=O)NS(=O)(=O)C1CC1]

Step 1: Methyl (1R,14R,18R,22S,25S)-22-cyclopentyl-7,20,23-trioxo-6-phenyl-2,19-dioxa-8,21,24-triazatetracyclo[22.2.1.0³,⁸.0¹⁴,¹⁸]heptacosa-3,5-diene-25-carboxylate

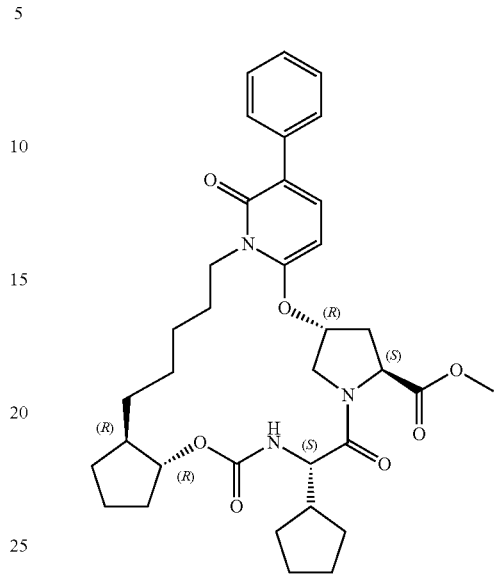

An oven-dried 100 mL Kjeldahl Flask under nitrogen was charged with the product of Example 83 Step 1 (100 mg, 0.161 mmol), dioxane (5 ml), phenylboronic acid (24.48 mg, 0.201 mmol), cesium carbonate (65.4 mg, 0.201 mmol), tricyclohexylphosphine (13.51 mg, 0.048 mmol), and tris(dibenzylideneacetone)dipalladium(0) (17.65 mg, 0.019 mmol). Heated in an 80° C. oil bath for 20 hours. HPLC/MS looks good. Cooled. Poured into 2.5% potassium bisulfate. Extracted three times with ethyl acetate, washed combined organic portions with brine, dried with anhydrous magnesium sulfate, filtered and rotary evaporated filtrate. Subjected to ISCO chromatography eluting with a hexane/ethyl acetate gradient. Evaporation of fractions containing product gave the title compound as a white solid remained. (75 mg, 0.121 mmol, 75% yield). LCMS (ES+) m/z 620.3 (M+H)⁺.

Step 2: (1R,14R,18R,22S,25S)-22-cyclopentyl-7,20,23-trioxo-6-phenyl-2,19-dioxa-8,21,24-triazatetracyclo[22.2.1.0³,⁸.0¹⁴,¹⁸]heptacosa-3,5-diene-25-carboxylic acid

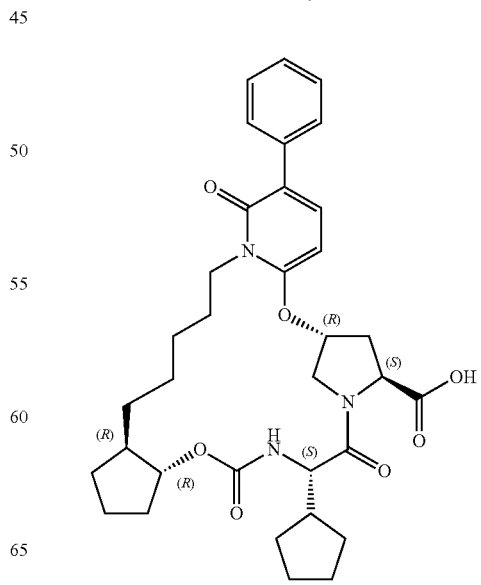

The title compound was prepared in a similar manner as Example 1 Step 5, utilizing methyl (1R,14R,18R,22S,25S)-22-cyclopentyl-7,20,23-trioxo-6-phenyl-2,19-dioxa-8,21,24-triazatetracyclo[22.2.1.0$^{3,8}$.0$^{14,18}$]heptacosa-3,5-diene-25-carboxylate to give a 100% yield. LCMS (ES+) m/z 606.3 (M+H)$^+$.

Step 3: (1R,14R,18R,22S,25S)-22-cyclopentyl-N-((1R,2S)-1-{[(cyclopropylsulfonyl)amino]carbonyl}-2-vinylcyclopropyl)-7,20,23-trioxo-6-phenyl-2,19-dioxa-8,21,24-triazatetracyclo[22.2.1.0$^{3,8}$.0$^{14,18}$] heptacosa-3,5-diene-25-carboxamide

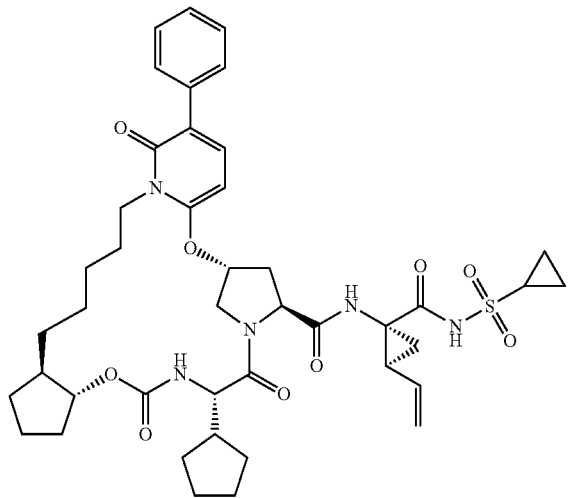 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(ccc(-c3ccccc3)c1=O)O2)C(=O)NS(=O)(=O)C1CC1]

The title compound was prepared in a similar manner as Example 1 Step 6, utilizing (1R,14R,18R,22S,25S)-22-cyclopentyl-7,20,23-trioxo-6-phenyl-2,19-dioxa-8,21,24-triazatetracyclo[22.2.1.0$^{3,8}$.0$^{14,18}$]heptacosa-3,5-diene-25-carboxylic acid to give a 50% yield. LCMS (ES+) m/z 818.3 (M+H)$^+$.

Example 87

NS3 protease 1b R155K K$_i$ Activity

The HCV NS3 protease inhibitory activity was measured using the protease time-resolved fluorescence (TRF) assay as described below and in International Patent Application Publication WO 2006/102087. The assay was performed with HCV genotype 1b (BK) NS3 modified with a R155K mutation.

The assay was performed in a final volume of 100 µl in assay buffer containing 50 mM HEPES, pH 7.5, 150 mM NaCl, 15% glycerol, 0.15% TRITON X-100, 10 mM DTT, and 0.1% PEG 8000. NS3 and NS4A protease is pre-incubated with various concentrations of inhibitors in DMSO for 30 minutes. The reaction is initiated by adding the TRF peptide substrate (final concentration 100 nM). NS3 mediated hydrolysis of the substrate is quenched after 1 hour at room temperature with 100 µl of 500 mM MES, pH 5.5. Product fluorescence is detected using either a VICTOR V2 or FUSION fluorophotometer (Perkin Elmer Life and Analytical Sciences) with excitation at 340 nm and emission at 615 nm with a 400 µs delay. Testing concentrations of the enzyme containing the R155K mutation were selected to result in a signal to background ratio (S/B) of 10-30. IC$_{50}$ values are derived using a standard four-parameter fit to the data. K$_i$ values are derived from IC$_{50}$ values using the following formula, $$IC_{50}=K_i(1+[S]/K_M),  \quad\quad\quad\quad \text{Eqn (1),}$$

where [S] is the concentration of substrate peptide in the reaction and K$_M$ is the Michaelis constant. See P. Gallinari et al., 38 BIOCHEM. 5620-32 (1999); P. Gallinari et al., 72 J. VIROL. 6758-69 (1998); M. Taliani et al., 240 ANAL. BIOCHEM. 60-67 (1996).

The activity table provided below illustrates the observed activity, where compound activity fell within the following ranges:

A: K$_i$ 1 nM to 5 nM
B: K$_i$ 0.5 nM to 1 nM
C: K$_i$ 0.1 nM to 0.5 nM
D: K$_i$ <0.1 nM

| Activity Table | |
|---|---|
| Name | Activity |
| (3aR,7S,10S,12R,26aR)-7-tert-butyl-N-((1R,2R)-1-{[(cyclopropylsulfonyl)amino]carbonyl}-2-ethylcyclopropyl)-5,8,19-trioxo-2,3,3a,5,6,7,8,11,12,21,22,23,24,25,26,26a-hexadecahydro-1H,10H,19H-9,12-methanocyclopenta[19,20][1,10,3,6,12]dioxatriazacycloicosino[12,11-b]isoquinoline-10-carboxamide | A |
| (3aS,7S,10S,12R,26aS)-7-tert-butyl-N-((1R,2R)-1-{[(cyclopropylsulfonyl)amino]carbonyl}-2-ethylcyclopropyl)-5,8,19-trioxo-2,3,3a,5,6,7,8,11,12,21,22,23,24,25,26,26a-hexadecahydro-1H,10H,19H-9,12-methanocyclopenta[19,20][1,10,3,6,12]dioxatriazacycloicosino[12,11-b]isoquinoline-10-carboxamide | A |
| (3aS,7S,10S,12R,26aS)-7-tert-butyl-N-((1R,2S)-1-{[(cyclopropylsulfonyl)amino]carbonyl}-2-vinylcyclopropyl)-5,8,19-trioxo-2,3,3a,5,6,7,8,11,12,21,22,23,24,25,26,26a-hexadecahydro-1H,10H,19H-9,12-methanocyclopenta[19,20][1,10,3,6,12]dioxatriazacycloicosino[12,11-b]isoquinoline-10-carboxamide | B |
| (3aR,7S,10S,12R,25aR)-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,21a,22,22a,23,24,25,25a-octadecahydro-10H,19H-9,12-methanocyclopenta[19,20]cyclopropa[14,15][1,10,3,6,12]dioxatriazacycloicosino[12,11-b]isoquinoline-10-carboxamide | B |
| (3aR,7S,10S,12R,25aR)-7-cyclopentyl-N-((1R,2R)-1-{[(cyclopropylsulfonyl)amino]carbonyl}-2-ethylcyclopropyl)-18-methoxy-5,8,19-trioxo-1,2,3,3a,5,6,7,8,11,12,21,22,23,24,25,25a-hexadecahydro-10H,19H-9,12- | B |

Activity Table

| Name | Activity |
|---|---|
| methanocyclopenta[18,19][1,10,3,6,12]dioxatriazacyclononadecino[11,12-b]quinazoline-10-carboxamide | |
| (1aR,5S,8S,10R,23aR)-5-cyclopentyl-N-((1R,2R)-1-{[(cyclopropylsulfonyl)amino]carbonyl}-2-ethylcyclopropyl)-3,6,17-trioxo-1,1a,3,4,5,6,9,10,19,20,21,22,23,23a-tetradecahydro-8H,17H-7,10-methanocyclopropa[18,19][1,10,3,6,12]dioxatriazacyclononadecino[12,11-b]isoquinoline-8-carboxamide | C |
| (1aS,5S,8S,10R,23aS)-5-cyclopentyl-N-((1R,2R)-1-{[(cyclopropylsulfonyl)amino]carbonyl}-2-ethylcyclopropyl)-3,6,17-trioxo-1,1a,3,4,5,6,9,10,19,20,21,22,23,23a-tetradecahydro-8H,17H-7,10-methanocyclopropa[18,19][1,10,3,6,12]dioxatriazacyclononadecino[12,11-b]isoquinoline-8-carboxamide | C |
| (1aS,5S,8S,10R,23aS)-5-cyclopentyl-N-((1R,2S)-1-{[(cyclopropylsulfonyl)amino]carbonyl}-2-vinylcyclopropyl)-3,6,17-trioxo-1,1a,3,4,5,6,9,10,19,20,21,22,23,23a-tetradecahydro-8H,17H-7,10-methanocyclopropa[18,19][1,10,3,6,12]dioxatriazacyclononadecino[12,11-b]isoquinoline-8-carboxamide | C |
| (1R,10E,and 10Z,14S,18R,22S,25S)-22-Cyclopentyl-N-((1R,2S)-1-{[(cyclopropyl-sulfonyl)amino]carbonyl}-2-vinylcyclopropyl)-7,20,23-trioxo-2,19-dioxa-8,21,24-triazatetracyclo[22.2.1.0$^{3,8}$.0$^{14,18}$]heptacosa-3,5,10-triene-25-carboxamide | C |
| (1R,14E,18S,22R,26S,29S)-26-cyclopentyl-N-((1R,2R)-1-{[(cyclopropylsulfonyl)amino]carbonyl}-2-ethylcyclopropyl)-7-methyl-11,24,27-trioxo-2,23-dioxa-4,12,25,28-tetraazapentacyclo[26.2.1.0$^{3,12}$.0$^{5,10}$.0$^{18,22}$]hentriaconta-3,5,7,9,14-pentaene-29-carboxamide | C |
| (1R,14R,18R,22S,25S)-22-cyclopentyl-N-((1R,2S)-1-{[(cyclopropylsulfonyl)amino]carbonyl}-2-vinylcyclopropyl)-7,20,23-trioxo-2,19-dioxa-8,21,24-triazatetracyclo[22.2.1.0$^{3,8}$.0$^{14,18}$]heptacosa-3,5-diene-25-carboxamide | C |
| (1R,14R,18R,22S,25S)-22-cyclopentyl-N-((1R,2S)-1-{[(cyclopropylsulfonyl)amino]carbonyl}-2-vinylcyclopropyl)-7,20,23-trioxo-6-phenyl-2,19-dioxa-8,21,24-triazatetracyclo[22.2.1.0$^{3,8}$.0$^{14,18}$]heptacosa-3,5-diene-25-carboxamide | C |
| (1R,14R,18R,22S,25S)-6-bromo-22-cyclopentyl-N-((1R,2S)-1-{[(cyclopropylsulfonyl)amino]carbonyl}-2-vinylcyclopropyl)-7,20,23-trioxo-2,19-dioxa-8,21,24-triazatetracyclo[22.2.1.0$^{3,8}$.0$^{14,18}$]heptacosa-3,5-diene-25-carboxamide | C |
| (3aR,7S,10S,12R,22E,24aS)-7-cyclopentyl-N-((1R,2S)-1-{[(cyclopropylsulfonyl)amino]carbonyl}-2-vinylcyclopropyl)-5,8,19-trioxo-2,3,3a,5,6,7,8,11,12,21,24,24a-dodecahydro-1H,10H,19H-9,12-methanocyclopenta[17,18][1,10,3,6,12]dioxatriazacyclooctadecino[12,11-b]isoquinoline-10-carboxamide | C |
| (3aR,7S,10S,12R,22E,25aS)-16-bromo-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,22E,25aS)-16-chloro-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,22E,25aS)-16-cyano-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,22E,25aS)-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,22E,25aS)-7-cyclopentyl-N-((1R,2R)-1-{[(cyclopropylsulfonyl)amino]carbonyl}-2-ethylcyclopropyl)-16-methoxy-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,22E,25aS)-7-cyclopentyl-N-((1R,2R)-1-{[(cyclopropylsulfonyl)amino]carbonyl}-2-ethylcyclopropyl)-15-methoxy-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,22E,25aS)-7-cyclopentyl-N-((1R,2R)-1-{[(cyclopropylsulfonyl)amino]carbonyl}-2-ethylcyclopropyl)-18-methoxy-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,22E,25aS)-7-cyclopentyl-N-((1R,2R)-1-{[(cyclopropylsulfonyl)amino]carbonyl}-2-ethylcyclopropyl)-5,8,20-trioxo-1,2,3,3a,5,6,7,8,11,12,21,24,25,25a-tetradecahydro-10H,20H-9,12-methanocyclopenta[r]pyrido[1',2':1,2]pyrimido[4,5-k][1,10,3,6]dioxadiazacyclononadecine-10-carboxamide | C |

Activity Table

| Name | Activity |
|---|---|
| (3aR,7S,10S,12R,22E,25aS)-7-cyclopentyl-N-((1R,2R)-1-{[(cyclopropylsulfonyl)amino]carbonyl}-2-ethylcyclopropyl)-16-methoxy-5,8,20-trioxo-1,2,3,3a,5,6,7,8,11,12,21,24,25,25a-tetradecahydro-10H,20H-9,12-methanocyclopenta[r]pyrido[1',2':1,2]pyrimido[4,5-k][1,10,3,6]dioxadiazacyclononadecine-10-carboxamide | C |
| (3aR,7S,10S,12R,22E,25aS)-7-cyclopentyl-N-((1R,2R)-1-{[(cyclopropylsulfonyl)amino]carbonyl}-2-ethylcyclopropyl)-5,8,19-trioxo-16-phenyl-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,22E,26aR)-7-cyclopentyl-N-((1R,2S)-1-{[(cyclopropylsulfonyl)amino]carbonyl}-2-vinylcyclopropyl)-5,8,19-trioxo-2,3,3a,5,6,7,8,11,12,21,24,25,26,26a-tetradecahydro-1H,10H,19H-9,12-methanocyclopenta[19,20][1,10,3,6,12]dioxatriazacycloicosino[12,11-b]isoquinoline-10-carboxamide | C |
| (3aR,7S,10S,12R,23E,25aS)-16-chloro-7-cyclohexyl-N-((1R,2R)-1-{[(cyclopropylsulfonyl)amino]carbonyl}-2-ethylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | C |
| (3aR,7S,10S,12R,23E,25aS)-7-cyclopentyl-N-((1R,2S)-1-{[(cyclopropylsulfonyl)amino]carbonyl}-2-vinylcyclopropyl)-17-fluoro-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | C |
| (3aR,7S,10S,12R,23E,25aS)-7-tert-butyl-16-chloro-N-((1R,2R)-1-{[(cyclopropylsulfonyl)amino]carbonyl}-2-ethylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | C |
| (3aR,7S,10S,12R,23E,25aS)-7-tert-butyl-N-((1R,2S)-1-{[(cyclopropylsulfonyl)amino]carbonyl}-2-vinylcyclopropyl)-16-methoxy-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | C |
| (3aR,7S,10S,12R,24aR)-7-cyclopentyl-N-((1R,2S)-1-{[(cyclopropylsulfonyl)amino]carbonyl}-2-vinylcyclopropyl)-5,8,19-trioxo-2,3,3a,5,6,7,8,11,12,21,22,23,24,24a-tetradecahydro-1H,10H,19H-9,12-methanocyclopenta[17,18][1,10,3,6,12]dioxatriazacyclooctadecino[12,11-b]isoquinoline-10-carboxamide | C |
| (3aR,7S,10S,12R,24aS)-16-chloro-7-cyclopentyl-N-((1R,2S)-1-{[(cyclopropylsulfonyl)amino]carbonyl}-2-vinylcyclopropyl)-5,8,19-trioxo-2,3,3a,5,6,7,8,11,12,21,22,22a,23,23a,24,24a-hexadecahydro-1H,10H,19H-9,12-methanocyclopenta[18,19]cyclopropa[15,16][1,10,3,6,12]dioxatriazacyclononadecino[12,11-b]isoquinoline-10-carboxamide | C |
| (3aR,7S,10S,12R,25aR)-16-bromo-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,25aR)-16-chloro-7-cyclohexyl-N-((1R,2R)-1-{[(cyclopropylsulfonyl)amino]carbonyl}-2-ethylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | C |
| (3aR,7S,10S,12R,25aR)-16-chloro-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | C |
| (3aR,7S,10S,12R,25aR)-16-chloro-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,25aR)-16-cyano-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,25aR)-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | C |
| (3aR,7S,10S,12R,25aR)-7-cyclopentyl-N-((1R,2R)-1-{[(cyclopropylsulfonyl)amino]carbonyl}-2-ethylcyclopropyl)-17-fluoro-5,8,19-trioxo- | C |

Activity Table

| Name | Activity |
|---|---|
| 1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | |
| (3aR,7S,10S,12R,25aR)-7-cyclopentyl-N-((1R,2R)-1-{[(cyclopropylsulfonyl)amino]carbonyl}-2-ethylcyclopropyl)-16-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | C |
| (3aR,7S,10S,12R,25aR)-7-cyclopentyl-N-((1R,2R)-1-{[(cyclopropylsulfonyl)amino]carbonyl}-2-ethylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,25aR)-7-cyclopentyl-N-((1R,2R)-1-{[(cyclopropylsulfonyl)amino]carbonyl}-2-ethylcyclopropyl)-16-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,25aR)-7-cyclopentyl-N-((1R,2R)-1-{[(cyclopropylsulfonyl)amino]carbonyl}-2-ethylcyclopropyl)-5,8,19-trioxo-16-phenyl-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,25aR)-7-cyclopentyl-N-((1R,2S)-1-{[(cyclopropylsulfonyl)amino]carbonyl}-2-vinylcyclopropyl)-5,8,19-trioxo-16-(trifluoromethyl)-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,25aR)-7-cyclopentyl-N-((1R,2S)-1-{[(cyclopropylsulfonyl)amino]carbonyl}-2-vinylcyclopropyl)-18-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | C |
| (3aR,7S,10S,12R,25aR)-7-tert-butyl-16-chloro-N-((1R,2R)-1-{[(cyclopropylsulfonyl)amino]carbonyl}-2-ethylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | C |
| (3aR,7S,10S,12R,25aR)-7-tert-butyl-N-((1R,2R)-1-{[(cyclopropylsulfonyl)amino]carbonyl}-2-ethylcyclopropyl)-16-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | C |
| (3aR,7S,10S,12R,26aR)-7-cyclopentyl-N-((1R,2S)-1-{[(cyclopropylsulfonyl)amino]carbonyl}-2-vinylcyclopropyl)-5,8,19-trioxo-2,3,3a,5,6,7,8,11,12,21,22,23,24,25,26,26a-hexadecahydro-1H,10H,19H-9,12-methanocyclopenta[19,20][1,10,3,6,12]dioxatriazacycloicosino[12,11-b]isoquinoline-10-carboxamide | C |
| (3aR,7S,10S,12R,26aR)-7-tert-butyl-N-((1R,2S)-1-{[(cyclopropylsulfonyl)amino]carbonyl}-2-vinylcyclopropyl)-5,8,19-trioxo-2,3,3a,5,6,7,8,11,12,21,22,23,24,25,26,26a-hexadecahydro-1H,10H,19H-9,12-methanocyclopenta[19,20][1,10,3,6,12]dioxatriazacycloicosino[12,11-b]isoquinoline-10-carboxamide | C |
| (1aR,5S,8S,10R,23aR)-5-cyclopentyl-N-((1R,2S)-1-{[(cyclopropylsulfonyl)amino]carbonyl}-2-vinylcyclopropyl)-3,6,17-trioxo-1,1a,3,4,5,6,9,10,19,20,21,22,23,23a-tetradecahydro-8H,17H-7,10-methanocyclopropa[18,19][1,10,3,6,12]dioxatriazacyclononadecino[12,11-b]isoquinoline-8-carboxamide | D |
| (3aR,7S,10S,12R,22E,25aS)-16-bromo-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,22E,25aS)-16-chloro-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,22E,25aS)-16-cyano-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,22E,25aS)-7-cyclopentyl-N-((1R,2R)-1-{[(cyclopropylsulfonyl)amino]carbonyl}-2-ethylcyclopropyl)-5,8,19-trioxo-16-(trifluoromethyl)-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | D |

-continued

Activity Table

| Name | Activity |
|---|---|
| (3aR,7S,10S,12R,22E,25aS)-7-cyclopentyl-N-((1R,2R)-1-{[(cyclopropylsulfonyl)amino]carbonyl}-2-ethylcyclopropyl)-16-(methylsulfonyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,22E,25aS)-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,22E,25aS)-7-cyclopentyl-N-((1R,2S)-1-{[(cyclopropylsulfonyl)amino]carbonyl}-2-vinylcyclopropyl)-5,8,19-trioxo-16-(trifluoromethyl)-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,22E,25aS)-7-cyclopentyl-N-((1R,2S)-1-{[(cyclopropylsulfonyl)amino]carbonyl}-2-vinylcyclopropyl)-16-(methylsulfonyl)-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,22E,25aS)-7-cyclopentyl-N-((1R,2S)-1-{[(cyclopropylsulfonyl)amino]carbonyl}-2-vinylcyclopropyl)-16-methoxy-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,22E,25aS)-7-cyclopentyl-N-((1R,2S)-1-{[(cyclopropylsulfonyl)amino]carbonyl}-2-vinylcyclopropyl)-15-methoxy-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,22E,25aS)-7-cyclopentyl-N-((1R,2S)-1-{[(cyclopropylsulfonyl)amino]carbonyl}-2-vinylcyclopropyl)-18-methoxy-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,22E,25aS)-7-cyclopentyl-N-((1R,2S)-1-{[(cyclopropylsulfonyl)amino]carbonyl}-2-vinylcyclopropyl)-5,8,20-trioxo-1,2,3,3a,5,6,7,8,11,12,21,24,25,25a-tetradecahydro-10H,20H-9,12-methanocyclopenta[r]pyrido[1',2':1,2]pyrimido[4,5-k][1,10,3,6]dioxadiazacyclononadecine-10-carboxamide | D |
| (3aR,7S,10S,12R,22E,25aS)-7-cyclopentyl-N-((1R,2S)-1-{[(cyclopropylsulfonyl)amino]carbonyl}-2-vinylcyclopropyl)-16-methoxy-5,8,20-trioxo-1,2,3,3a,5,6,7,8,11,12,21,24,25,25a-tetradecahydro-10H,20H-9,12-methanocyclopenta[r]pyrido[1',2':1,2]pyrimido[4,5-k][1,10,3,6]dioxadiazacyclononadecine-10-carboxamide | D |
| (3aR,7S,10S,12R,22E,25aS)-7-cyclopentyl-N-((1R,2S)-1-{[(cyclopropylsulfonyl)amino]carbonyl}-2-vinylcyclopropyl)-5,8,19-trioxo-16-phenyl-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,22E,25aS)-7-cyclopentyl-N-((1R,2S)-1-{[(cyclopropylsulfonyl)amino]carbonyl}-2-vinylcyclopropyl)-16-methyl-5,8,19-trioxo-1,2,3,3a,5,6,7,8,11,12,21,24,25,25a-tetradecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,23E,25aS)-16-chloro-7-cyclohexyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | D |
| (3aR,7S,10S,12R,23E,25aS)-16-chloro-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | D |
| (3aR,7S,10S,12R,23E,25aS)-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | D |
| (3aR,7S,10S,12R,23E,25aS)-7-cyclopentyl-N-((1R,2S)-1-{[(cyclopropylsulfonyl)amino]carbonyl}-2-vinylcyclopropyl)-16-methoxy-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | D |

-continued

Activity Table

| Name | Activity |
|---|---|
| (3aR,7S,10S,12R,23E,25aS)-7-tert-butyl-16-chloro-N-((1R,2S)-1-{[(cyclopropylsulfonyl)amino]carbonyl}-2-vinylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | D |
| (3aR,7S,10S,12R,23E,25aS)-7-tert-butyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,25,25a-tetradecahydro-10H,19H-9,12-methanocyclopenta[18,19][1,10,3,6,12]dioxatriazacyclononadecino[12,11-b]isoquinoline-10-carboxamide | D |
| (3aR,7S,10S,12R,25aR)-16-chloro-7-cyclohexyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | D |
| (3aR,7S,10S,12R,25aR)-16-chloro-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | D |
| (3aR,7S,10S,12R,25aR)-16-chloro-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,25aR)-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | D |
| (3aR,7S,10S,12R,25aR)-7-cyclopentyl-N-((1R,2S)-1-{[(cyclopropylsulfonyl)amino]carbonyl}-2-vinylcyclopropyl)-17-fluoro-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | D |
| (3aR,7S,10S,12R,25aR)-7-cyclopentyl-N-((1R,2S)-1-{[(cyclopropylsulfonyl)amino]carbonyl}-2-vinylcyclopropyl)-16-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | D |
| (3aR,7S,10S,12R,25aR)-7-cyclopentyl-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,25aR)-7-cyclopentyl-N-((1R,2S)-1-{[(cyclopropylsulfonyl)amino]carbonyl}-2-vinylcyclopropyl)-16-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,25aR)-7-cyclopentyl-N-((1R,2S)-1-{[(cyclopropylsulfonyl)amino]carbonyl}-2-vinylcyclopropyl)-15-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,25aR)-7-cyclopentyl-N-((1R,2S)-1-{[(cyclopropylsulfonyl)amino]carbonyl}-2-vinylcyclopropyl)-16-methyl-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[11,12-b]quinazoline-10-carboxamide | D |
| (3aR,7S,10S,12R,25aR)-7-tert-butyl-16-chloro-N-((1R,2S)-1-{[(cyclopropylsulfonyl)amino]carbonyl}-2-vinylcyclopropyl)-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | D |
| (3aR,7S,10S,12R,25aR)-7-tert-butyl-N-((1R,2S)-1-{[(cyclopropylsulfonyl)amino]carbonyl}-2-vinylcyclopropyl)-16-methoxy-5,8,19-trioxo-1,2,3,3a,5,6,7,8,11,12,21,22,23,24,25,25a-hexadecahydro-10H,19H-9,12-methanocyclopenta[18,19][1,10,3,6,12]dioxatriazacyclononadecino[12,11-b]isoquinoline-10-carboxamide | D |
| (1R,18R,22R,26S,29S)-7-chloro-26-cyclopentyl-N-[(1R,2S)-1-({[(1-methylcyclopropyl)sulfonyl]amino}carbonyl)-2-vinylcyclopropyl]-11,24,27-trioxo-2,23-dioxa-4,12,25,28-tetraazapentacyclo[26.2.1.0$^{3,12}$.0$^{5,10}$.0$^{18,22}$]hentriaconta-3,5,7,9-tetraene-29-carboxamide | D |

-continued

Activity Table

| Name | Activity |
|---|---|
| (1R,18R,22R,26S,29S)-26-cyclopentyl-7-methoxy-N-[(1R,2S)-1-({[(1-methylcyclopropyl)sulfonyl]amino}carbonyl)-2-vinylcyclopropyl]-11,24,27-trioxo-2,23-dioxa-4,12,25,28-tetraazapentacyclo[26.2.1.0$^{3,12}$.0$^{5,10}$.0$^{18,22}$]hentriaconta-3,5,7,9-tetraene-29-carboxamide | D |

Other embodiments are within the following claims. While several embodiments have been shown and described, various modifications may be made without departing from the spirit and scope of the present invention.

What is claimed is:

1. A compound of formula (I), or a pharmaceutical acceptable salt thereof:

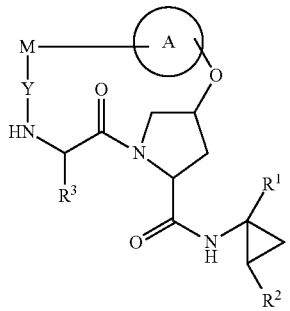

(I)

wherein:

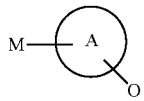

is selected from the group consisting of:

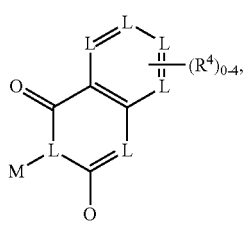

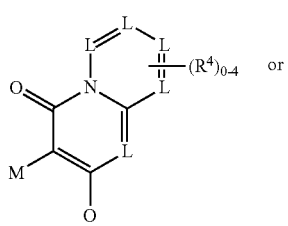

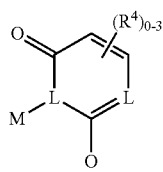

each L is independently selected from the group consisting of N and CH, provided that the total number of L that are N is from 1 to 4, $R^1$ is selected from the group consisting of —$CO_2H$, —$CONHSO_2$(cyclopropyl) and —$CONHSO_2$(1-methylcyclopropyl);

$R^2$ is selected from the group consisting of ethyl and ethenyl;

$R^3$ is selected from the group consisting of cyclopentyl, cyclohexyl, and —$C(CH_3)_3$;

each $R^4$ is independently selected from the group consisting of halogen atoms, $C_1$-$C_4$ alkoxy, $C_1$-$C_7$ alkyl, $C_2$-$C_7$ alkenyl, —CN, —$CF_3$, —$OCF_3$, $SCH_3$, —$SO_2(CH_3)$, $C_3$-$C_8$ cycloalkyl, $C_3$-$C_8$ cycloalkoxy, $C_1$-$C_6$ haloalkyl, phenyl, naphthyl and heteroaryl groups, wherein each said $R^4$ heteroaryl is selected from the group consisting of 5- and 6-membered aromatic rings having 1, 2 or 3 heteroatoms independently selected from N, O and S, and said $R^4$ heteroaryl is attached through a ring atom selected from C or N, each said $R^4$ phenyl, naphthyl and heteroaryl groups are substituted with 0 to 4 substituents independently selected from the group consisting of halogen atoms, —$OR^5$, —$SR^5$, —$N(R^5)_2$, —$N(C_1$-$C_6$ alkyl)$O(C_1$-$C_6$ alkyl), $C_1$-$C_6$ alkyl, $C_1$-$C_6$ haloalkyl, ($C_1$-$C_6$ haloalkoxy), —$NO_2$, —CN, —$CF_3$, —$SO_2(C_1$-$C_6$ alkyl), —$S(O)(C_1$-$C_6$ alkyl), —$NR^5SO_2R^6$, $SO_2N(R^6)_2$, —$NHCOOR^6$, —$NHCOR^6$, —$NHCONHR^6$, —$CO_2R^5$, —$C(O)R^5$ and —$CON(R^5)_2$, and 2 adjacent substituents of said $R^4$ phenyl, naphthyl and heteroaryl groups may be taken together to form a 3- to 6-membered cyclic ring containing 0 to 3 heteroatoms independently selected from N, O and S;

Y is selected from the group consisting of —C(O)—, —C(O)O— and —C(O)NH—;

each $R^5$ is independently H or $C_1$-$C_6$ alkyl;

each $R^6$ is independently H, $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl);

M is selected from the group consisting of $C_4$-$C_7$ alkylene and $C_4$-$C_7$ alkenylene, wherein said M is substituted with 0 to 3 substituents independently selected $C_1$-$C_8$ alkyl, provided that two adjacent substituents can together form a 3 to 6 membered ring.

2. The compound according to claim 1, wherein

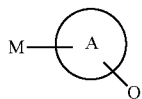

is selected from the group consisting of:

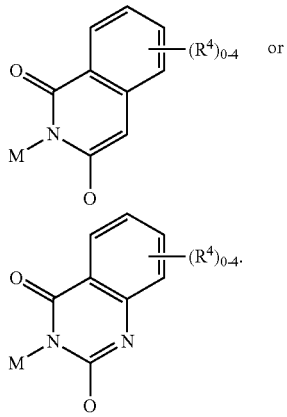

3. The compound according to claim 2, wherein 0 or 1 $R^4$ is present and, if present, is selected from the group consisting of —Br, —Cl, —CN, phenyl, —O-phenyl, —OCF$_3$, —OCH$_3$, —C(O)OH, —CH$_3$ and —C(O)CH$_3$.

4. The compound according to claim 3, wherein $R^1$ is —C(O)OH.

5. The compound according to claim 3, wherein $R^1$ is —C(O)NHSO$_2$cyclopropyl.

6. The compound according to claim 3, wherein $R^1$ is —CONHSO$_2$(1-methylcyclopropyl).

7. The compound according to claim 3, wherein $R^2$ is —CH$_2$CH$_3$.

8. The compound according to claim 3, wherein $R^2$ is —CH═CH$_2$.

9. The compound according to claim 3, wherein $R^3$ is cyclopentyl.

10. The compound according to claim 3, wherein $R^3$ is cyclohexyl.

11. The compound according to claim 3, wherein $R^3$ is —C(CH$_3$)$_3$.

12. The compound according claim 3, wherein M is selected from the group consisting of

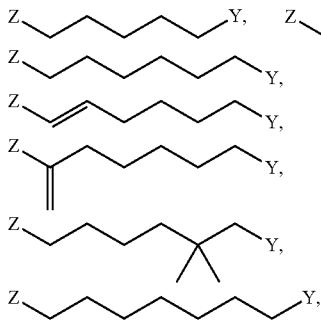

-continued

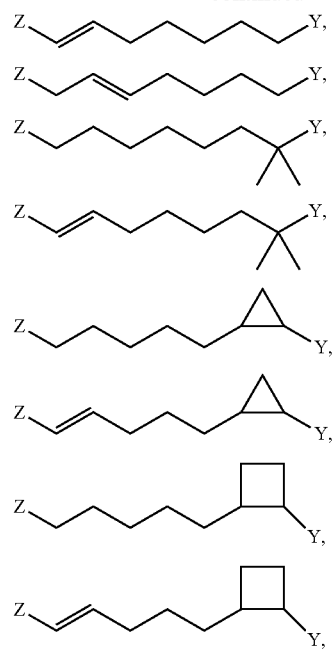

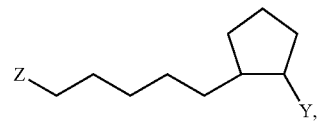

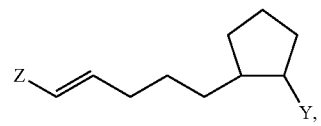

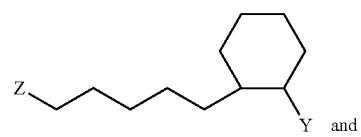 and

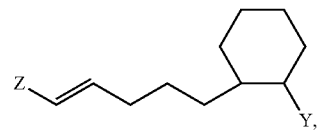

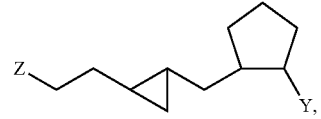

where Z is

.

13. The compound according to claim 1, wherein said compound has the following structure or a pharmaceutical acceptable salt thereof:

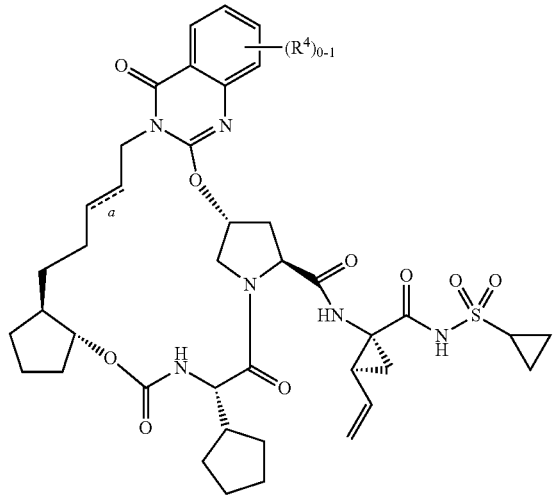

wherein "a" is an optionally present bond and $R^4$ if present is selected from the group consisting of —Br, —Cl, —CN, phenyl, —O-phenyl, —$OCF_3$, —$OCH_3$, —C(O)OH, —$CH_3$ and —C(O)$CH_3$.

14. The compound according to claim 1, wherein said compound has the following structure or a pharmaceutically acceptable salt thereof:

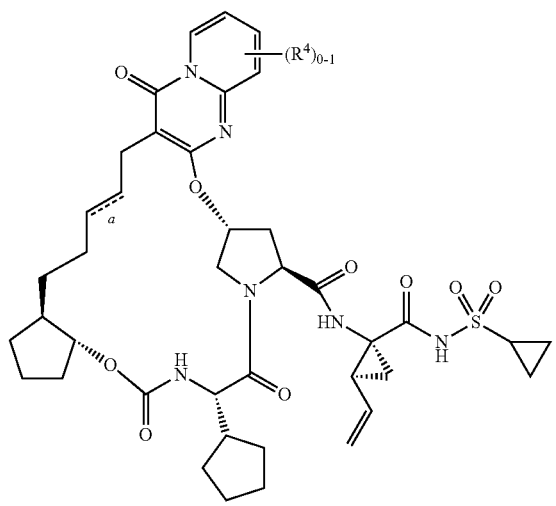

wherein "a" is an optionally present bond and $R^4$ if present is selected from the group consisting of —Br, —Cl, —CN, phenyl, —O-phenyl, —$OCF_3$, —$OCH_3$, —C(O)OH, —$CH_3$ and —C(O)$CH_3$.

15. The compound according to claim 1, wherein said compound has the following structure or a pharmaceutical acceptable salt thereof:

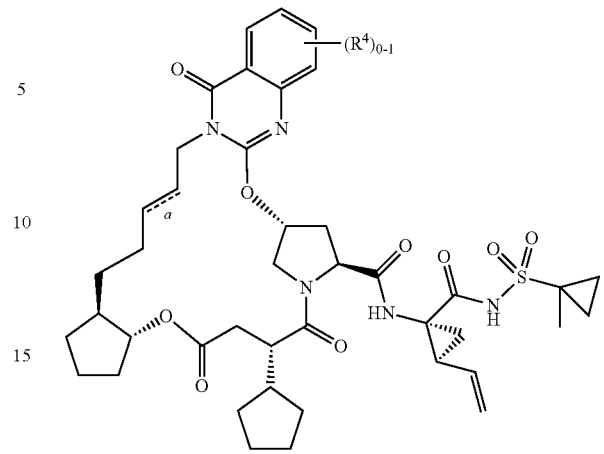

wherein "a" is an optionally present bond and $R^4$ if present is selected from the group consisting of —Br, —Cl, —CN, phenyl, —O-phenyl, —$OCF_3$, —$OCH_3$, —C(O)OH, —$CH_3$ and —C(O)$CH_3$.

16. The compound according to claim 1, wherein said compound is selected from the group consisting of:

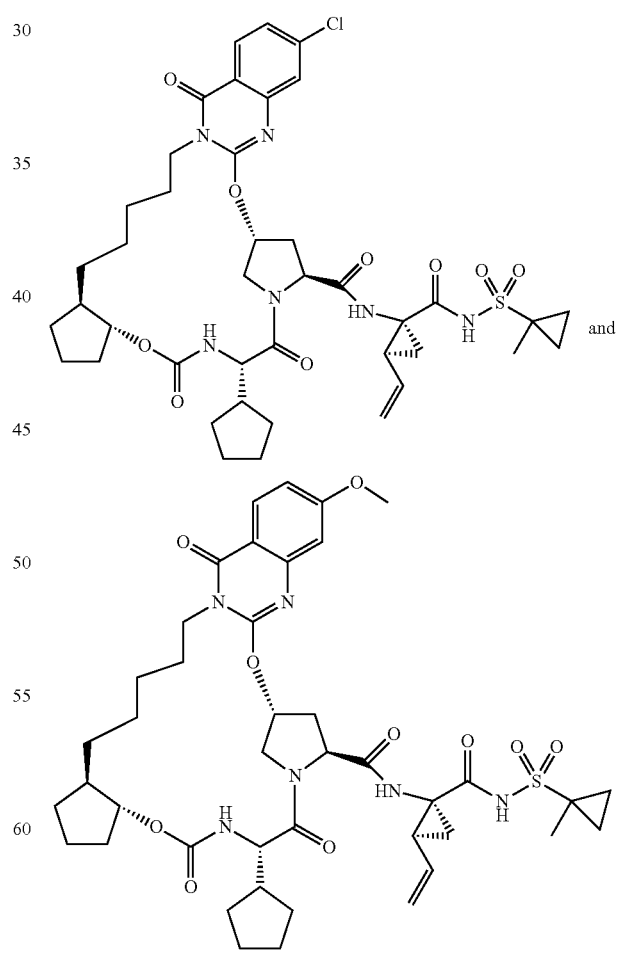

and pharmaceutically acceptable salts thereof.

17. A compound selected from the group consisting of:
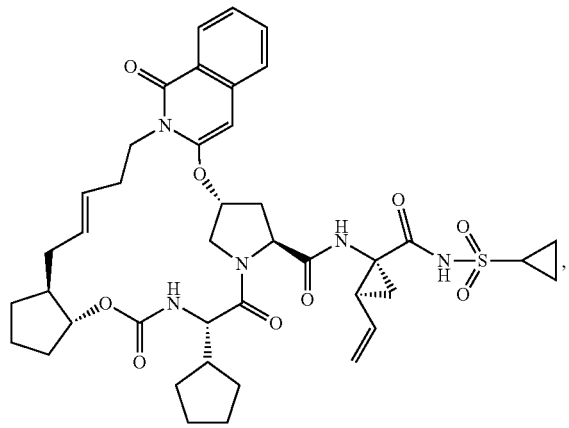
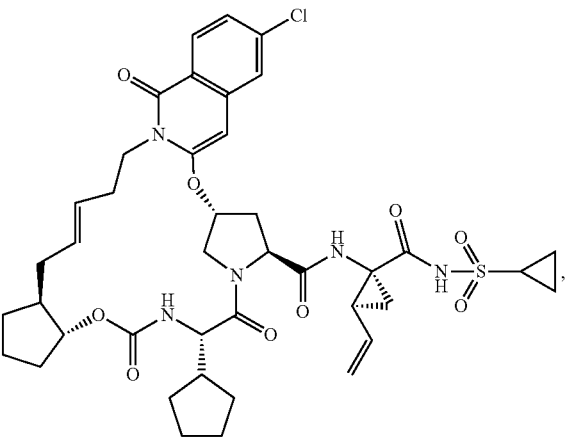
-continued
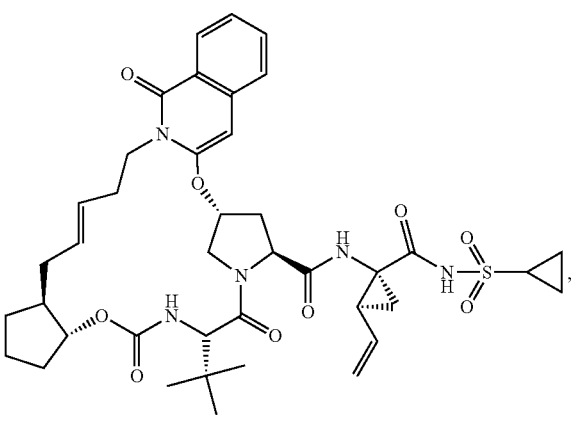
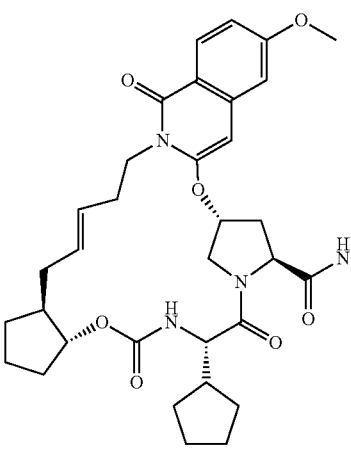
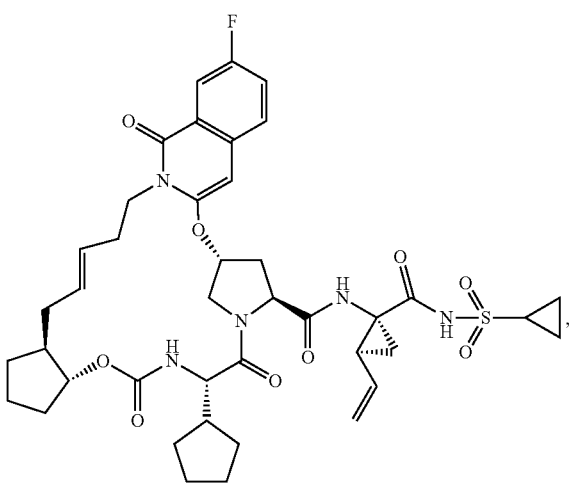
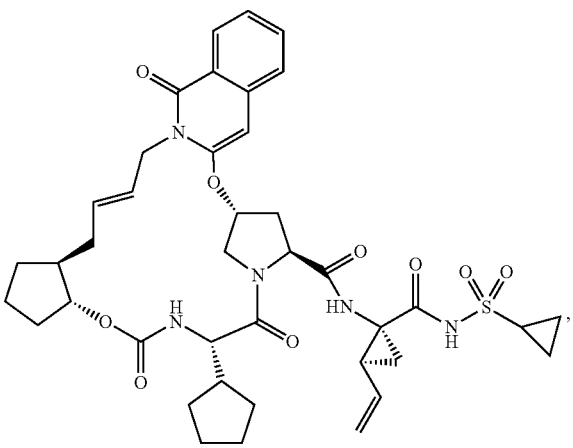

145
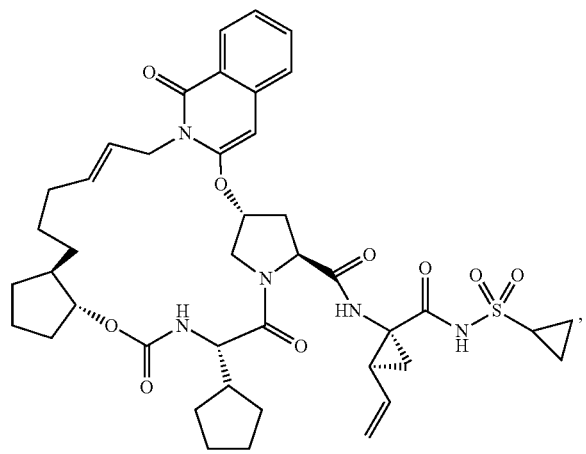
146
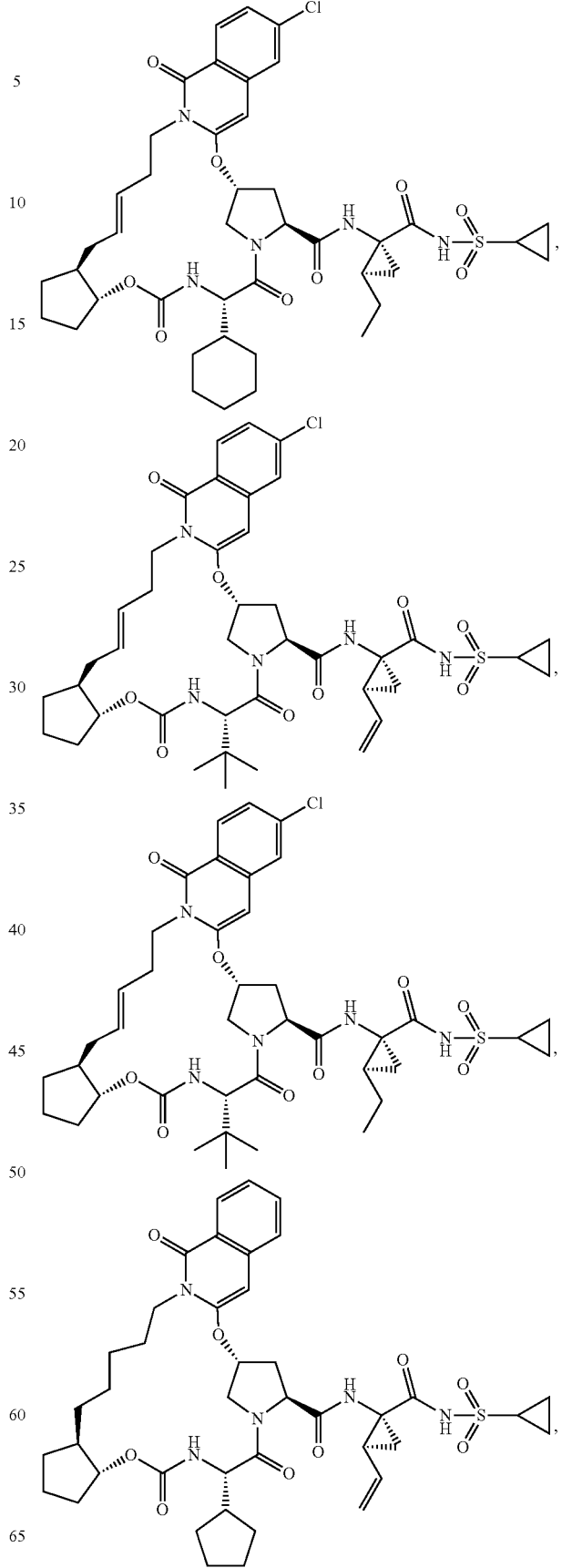

147
-continued
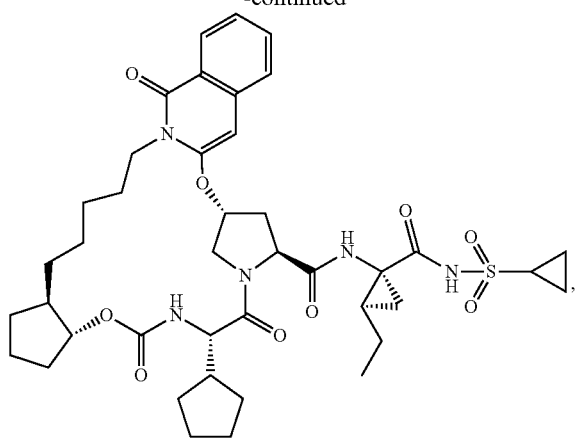
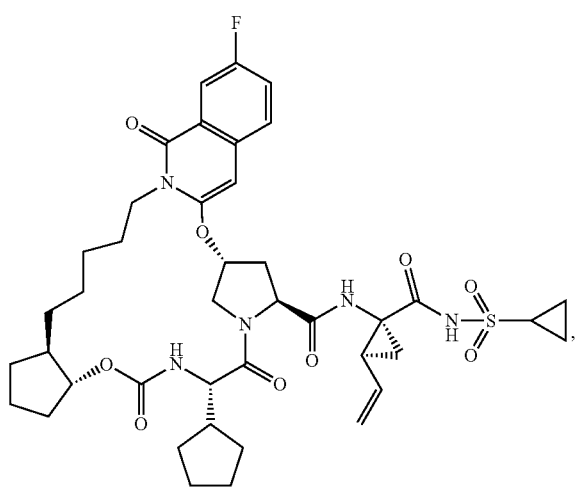
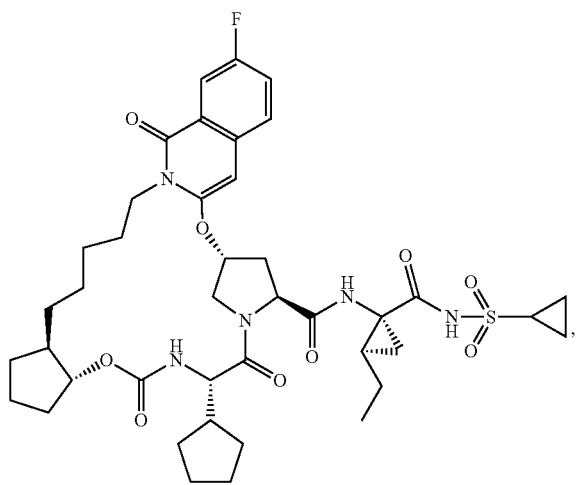
148
-continued
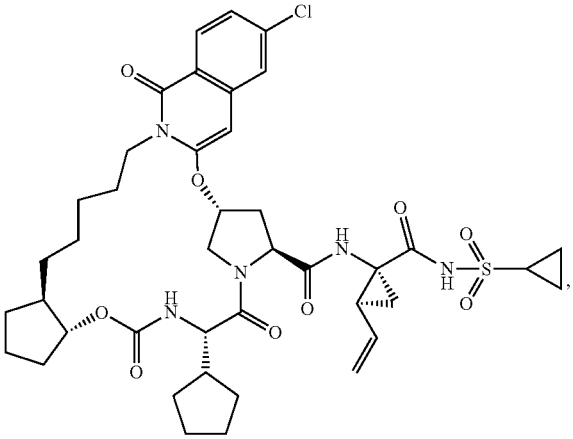
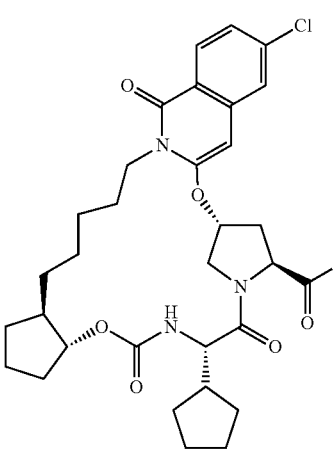
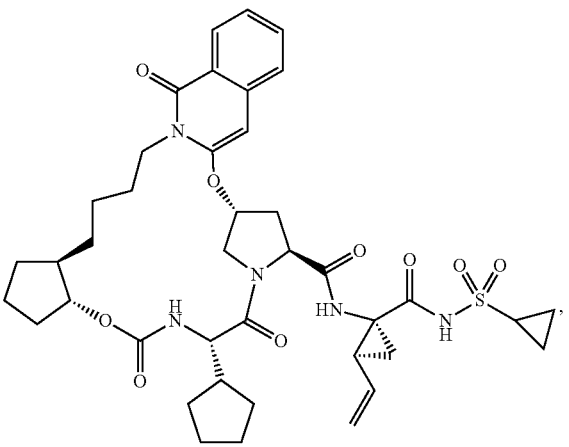

149 -continued
150 -continued
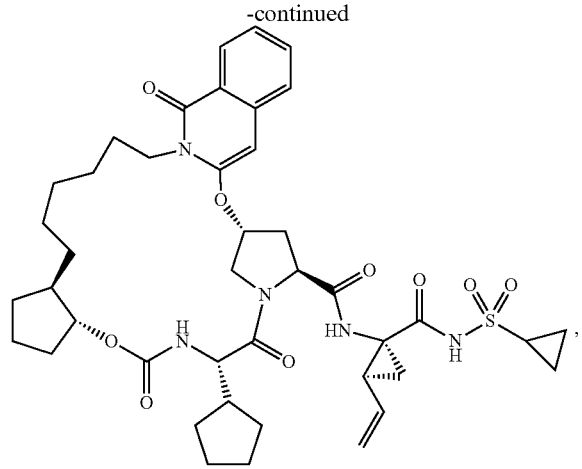
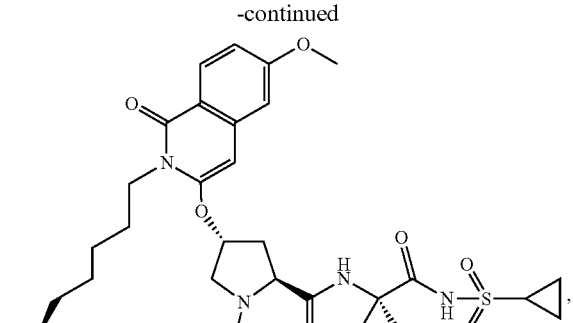
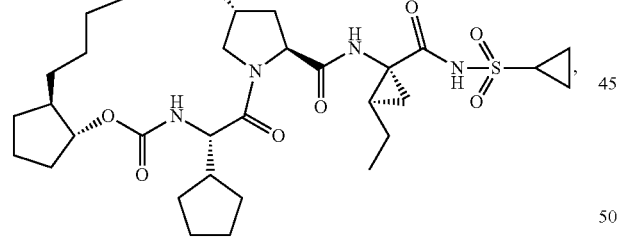
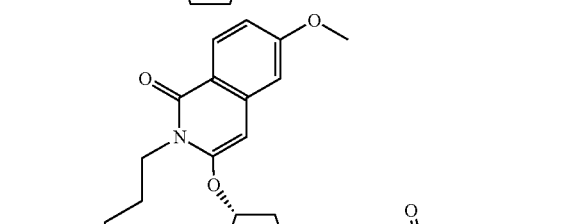
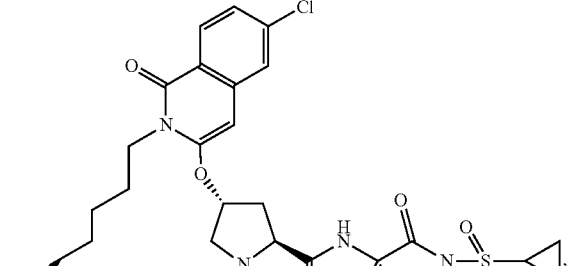
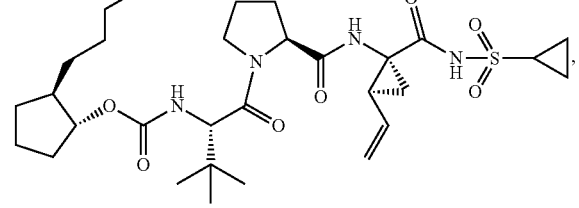

151
-continued
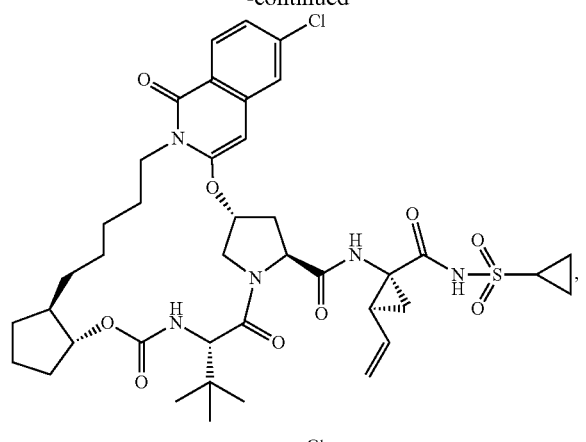
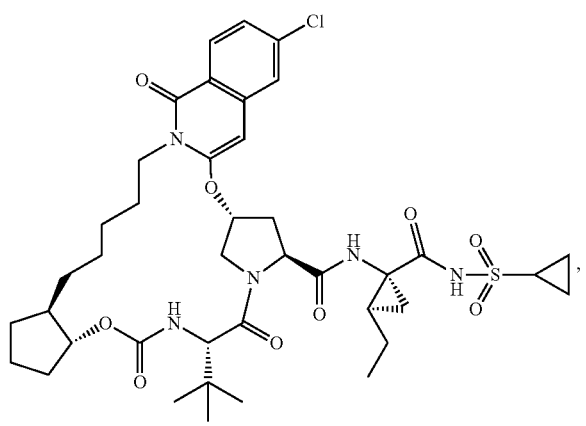
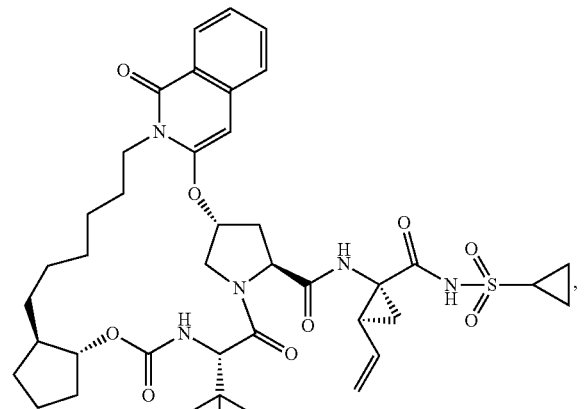
152
-continued
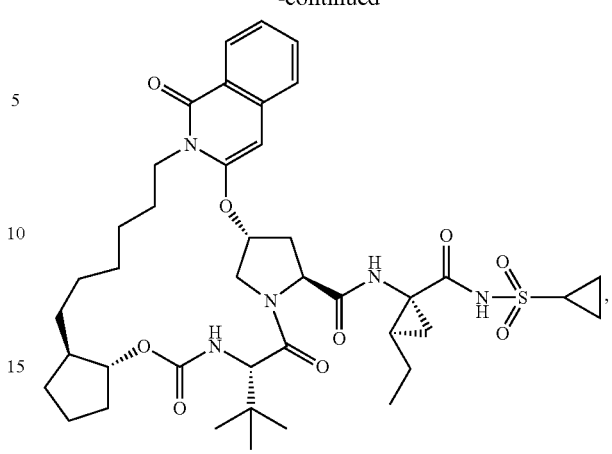
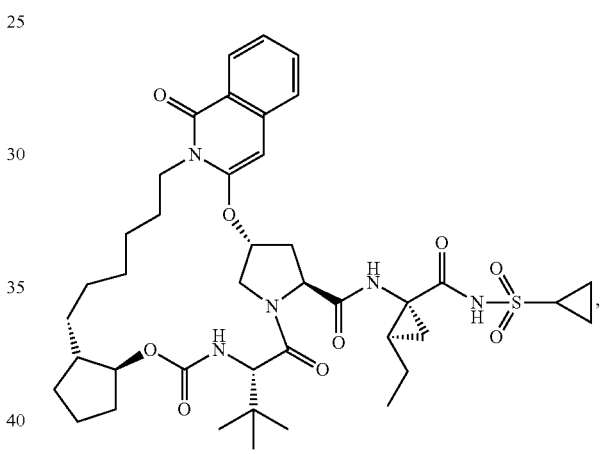
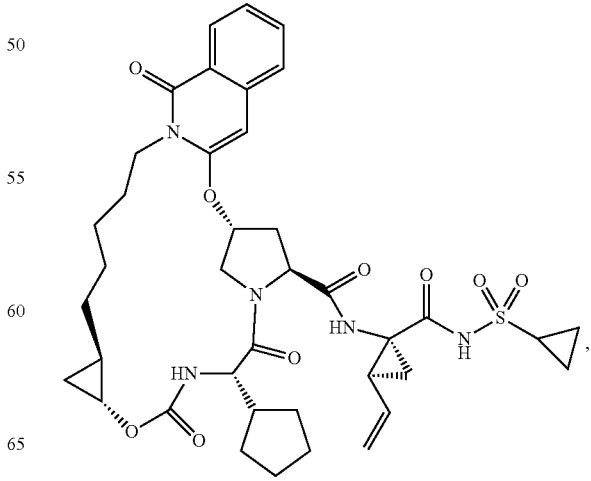

153
-continued
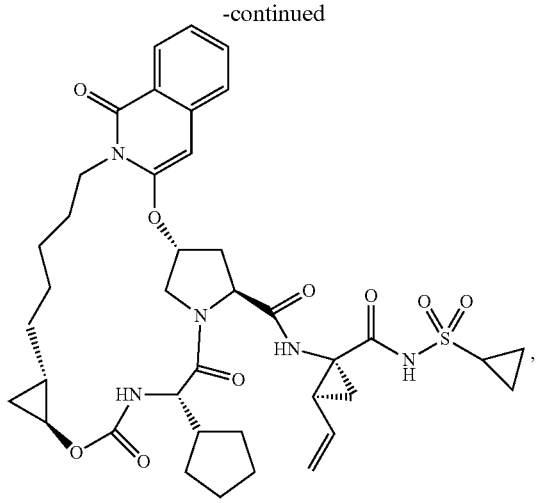
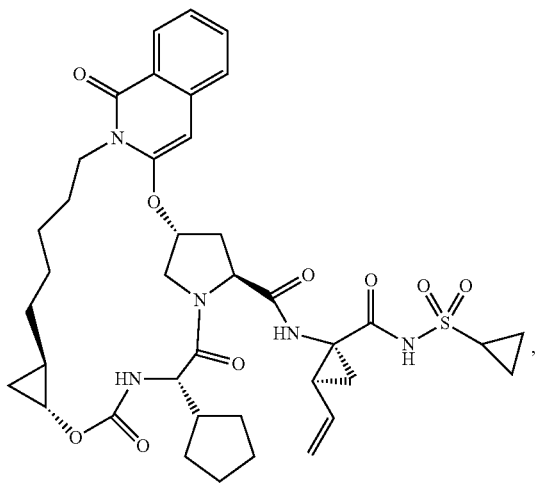
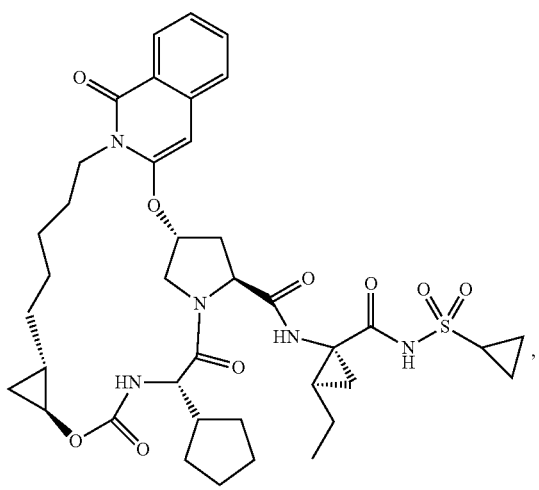
154
-continued
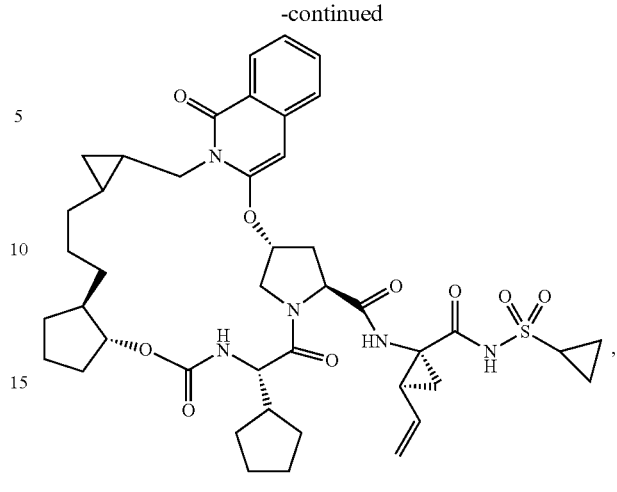
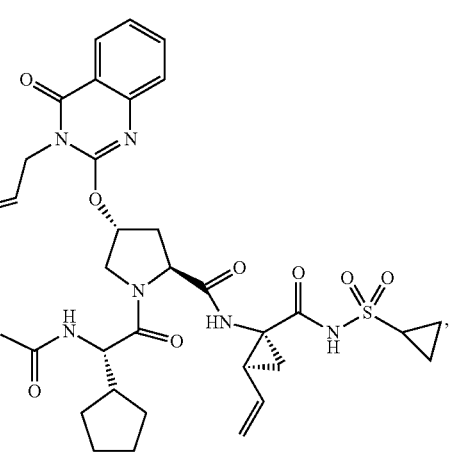

155
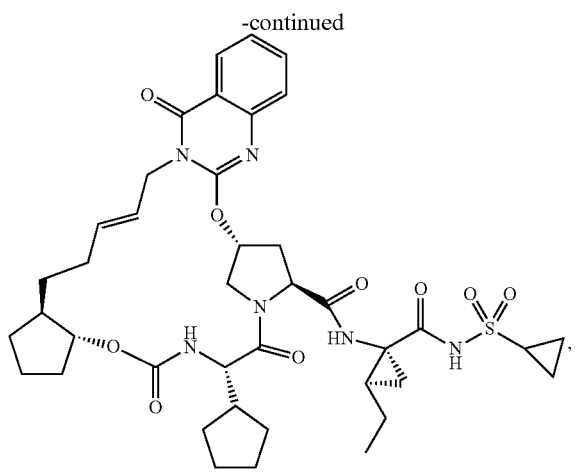
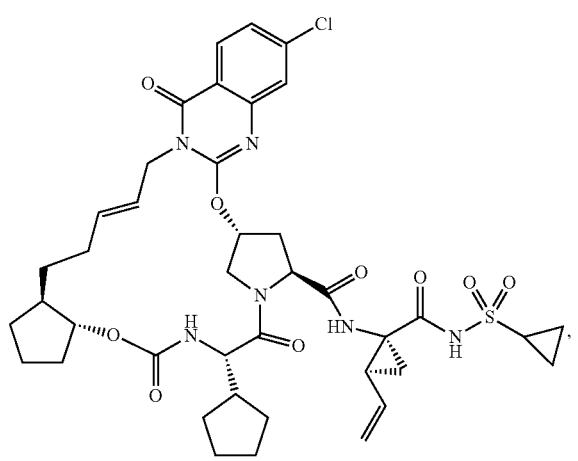
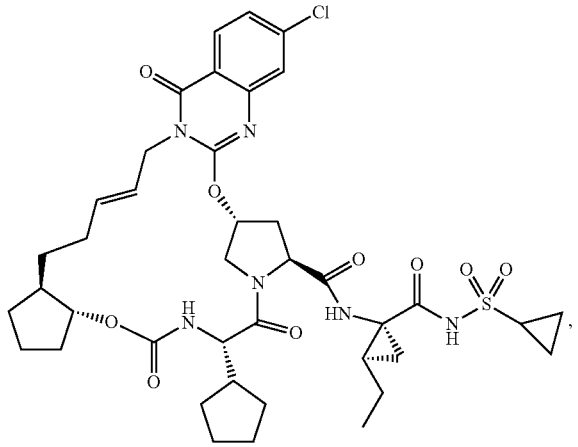
156
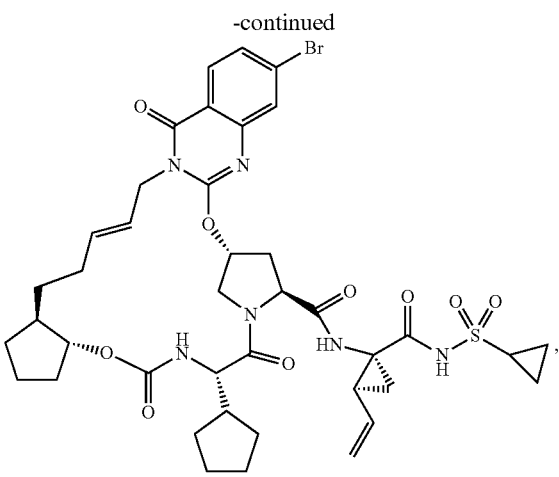
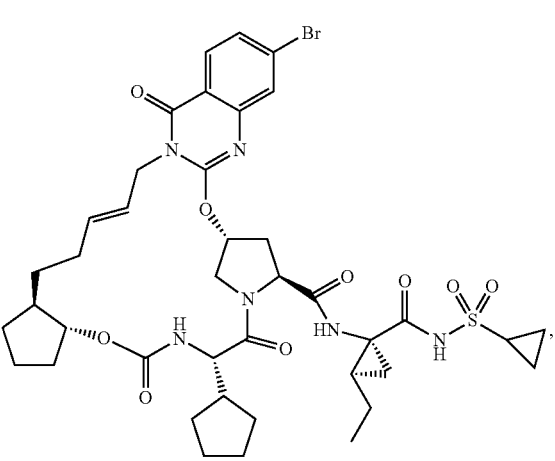
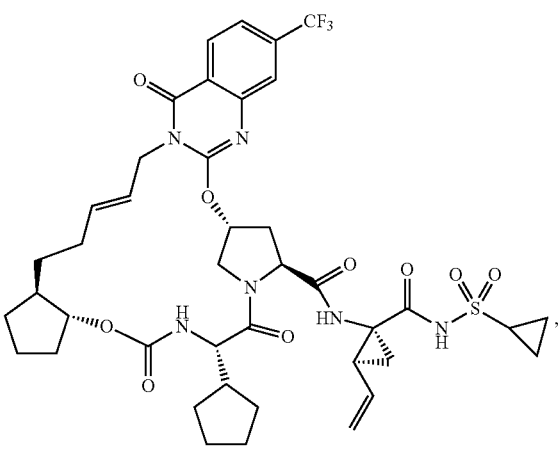

157
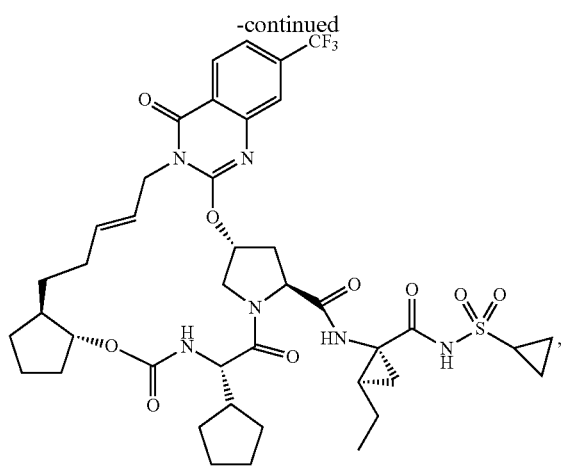
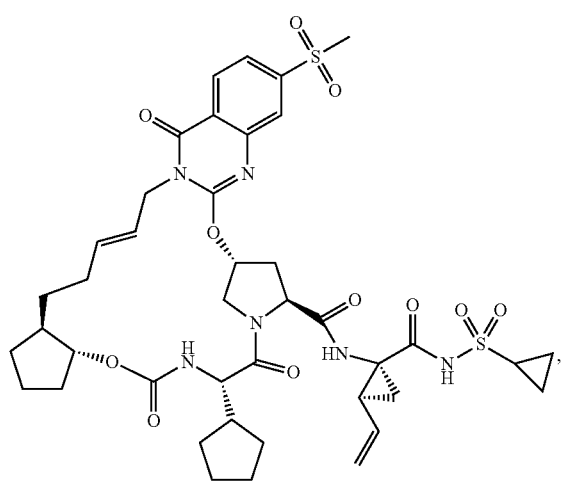
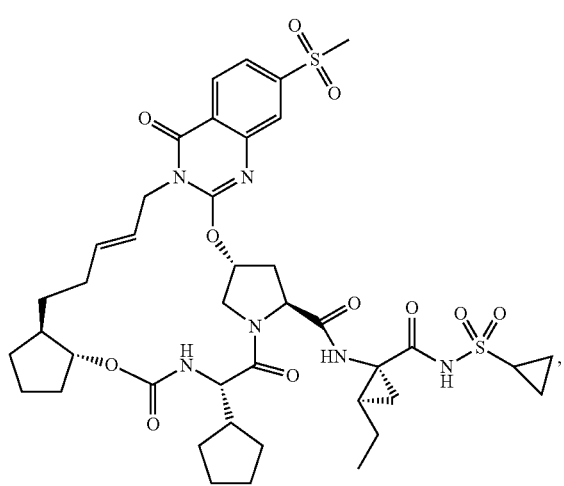
158
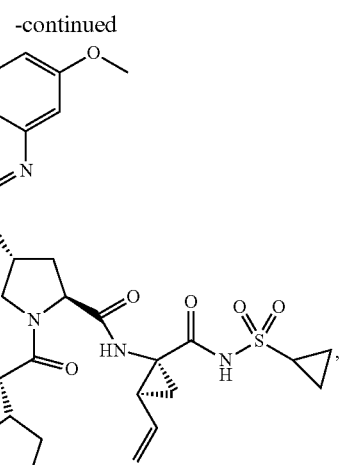
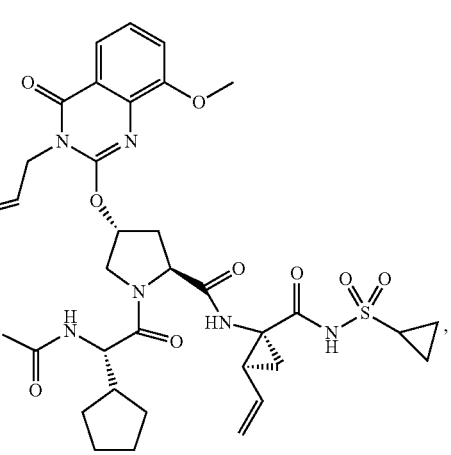

159
-continued
160
-continued
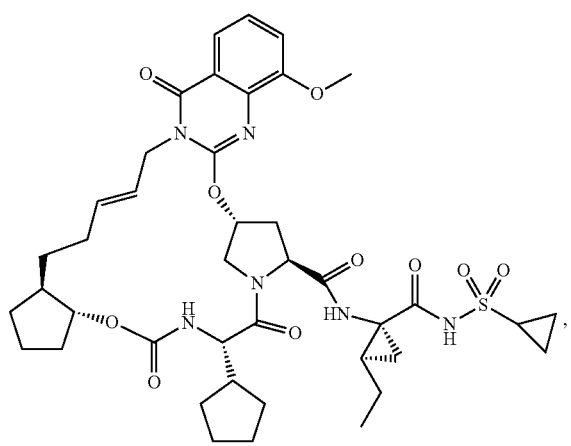
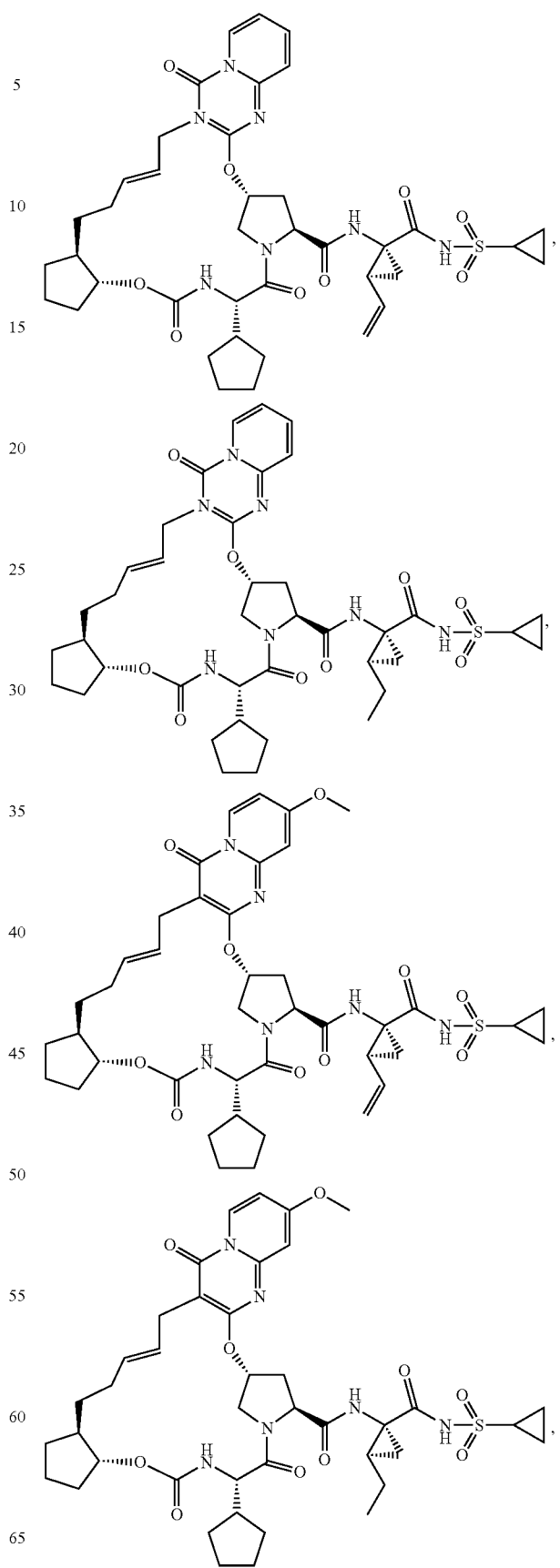

161
-continued
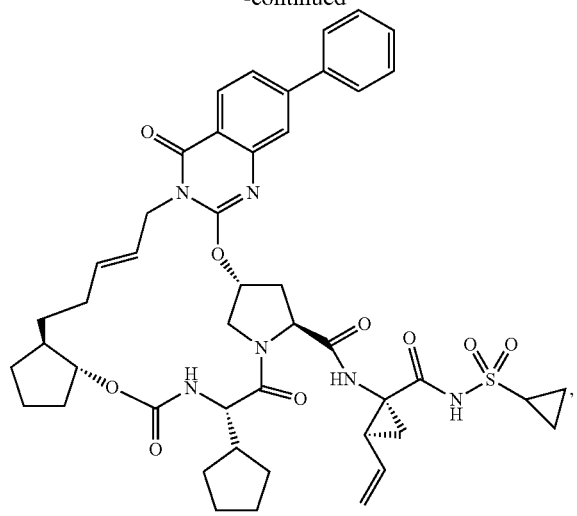
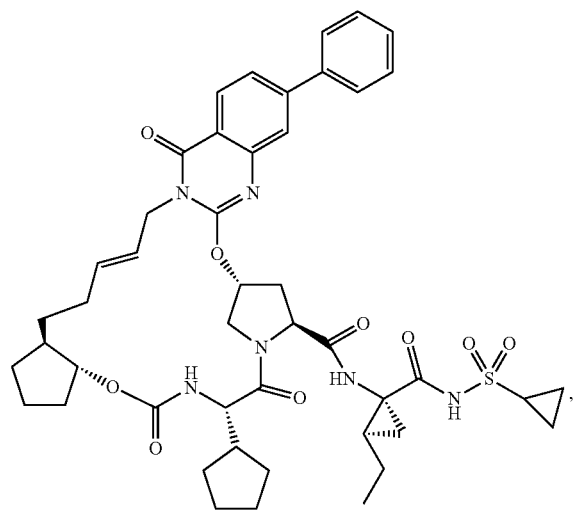
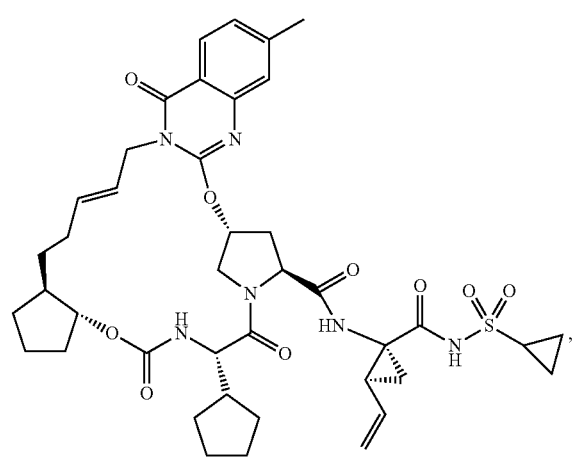
162
-continued
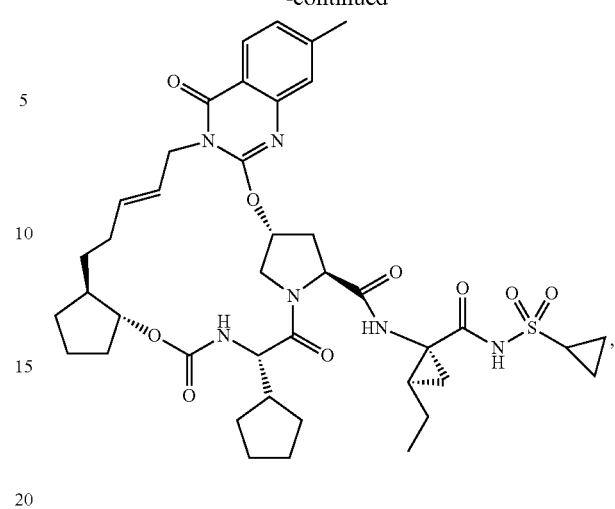
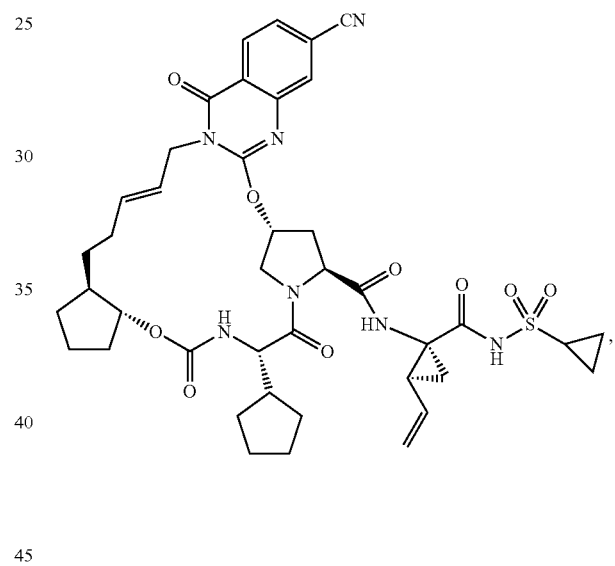
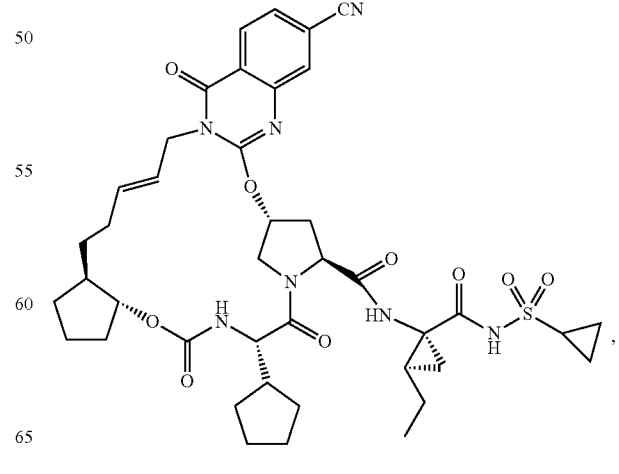

163
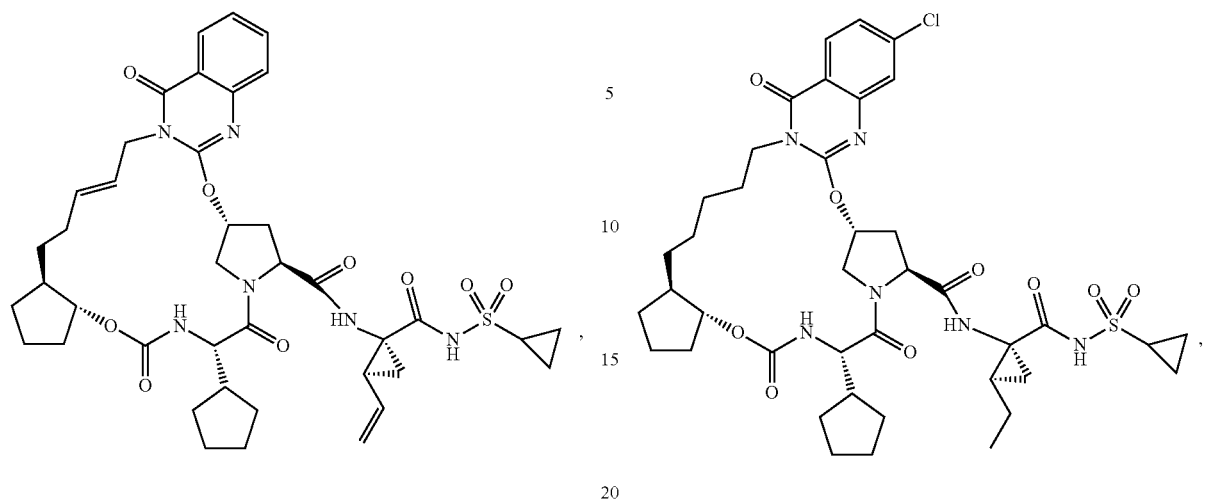
164
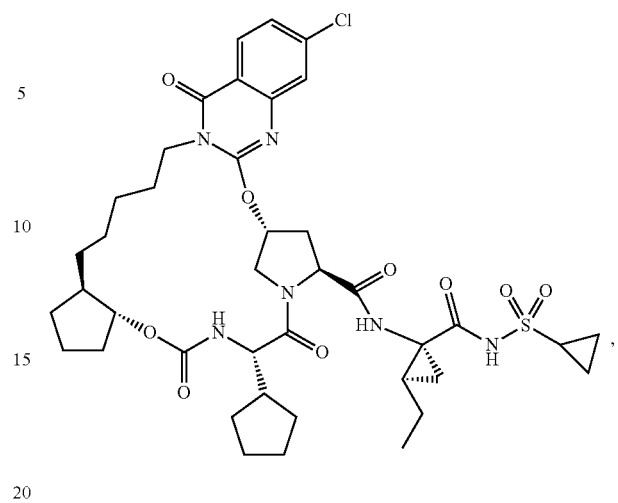
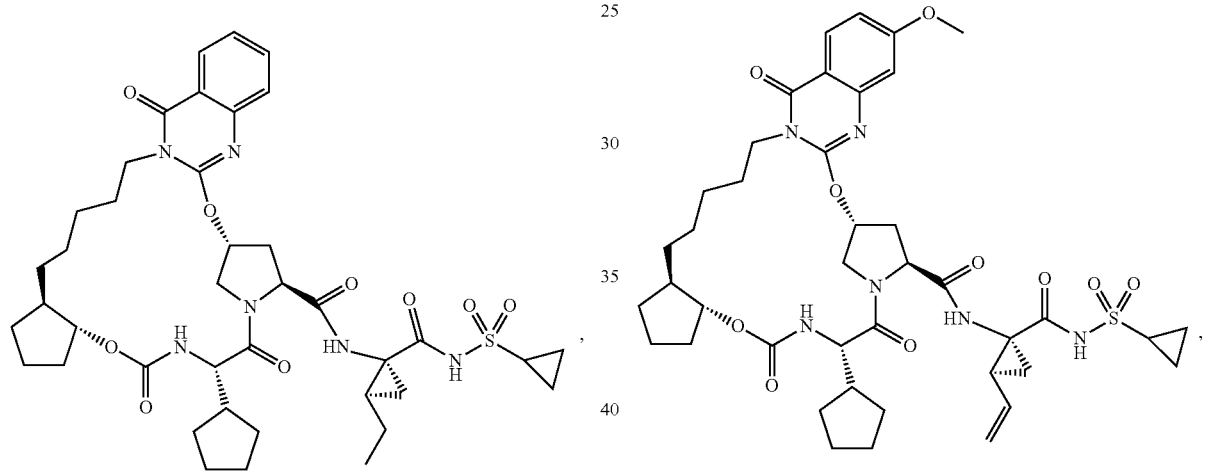
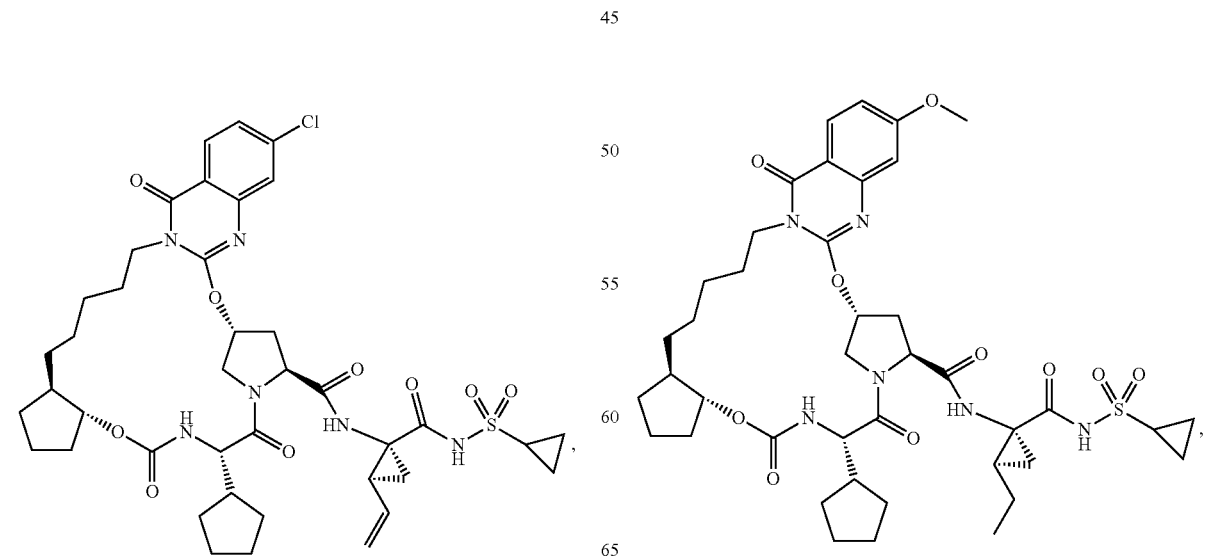

165
-continued
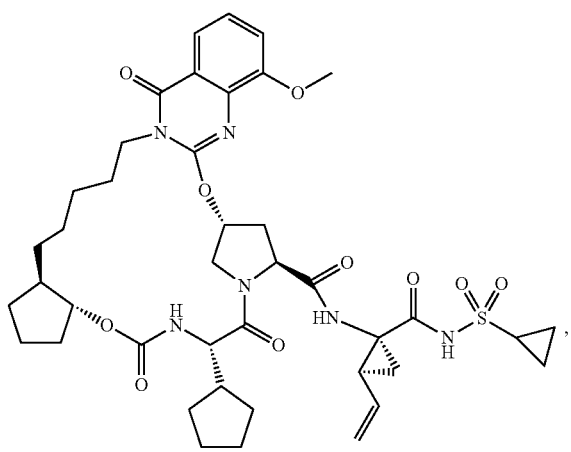
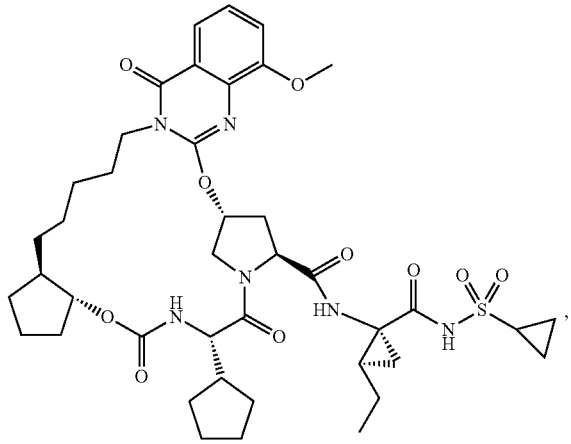
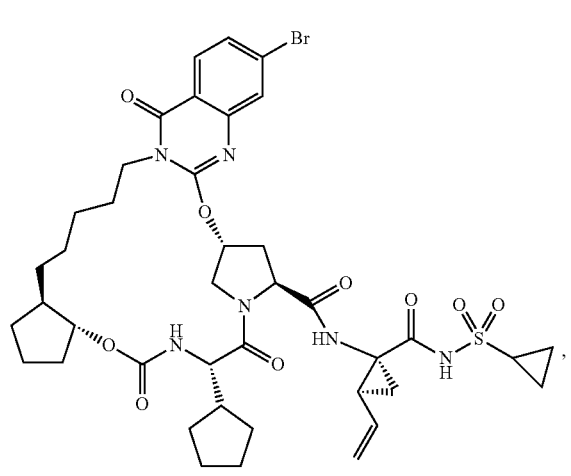
166
-continued
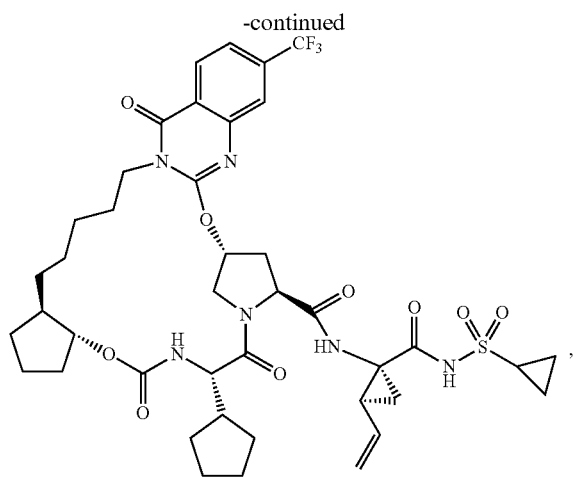
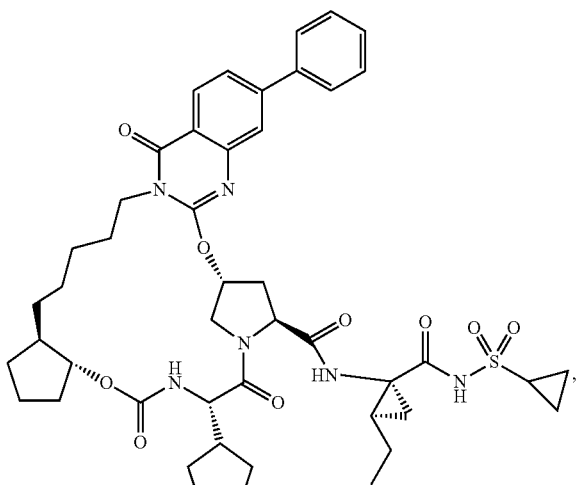

167 168
-continued -continued
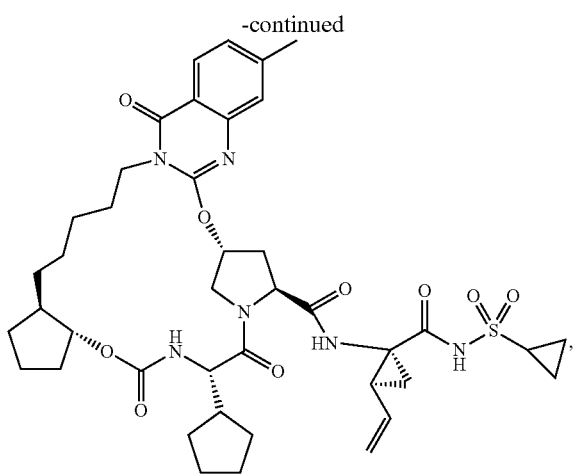
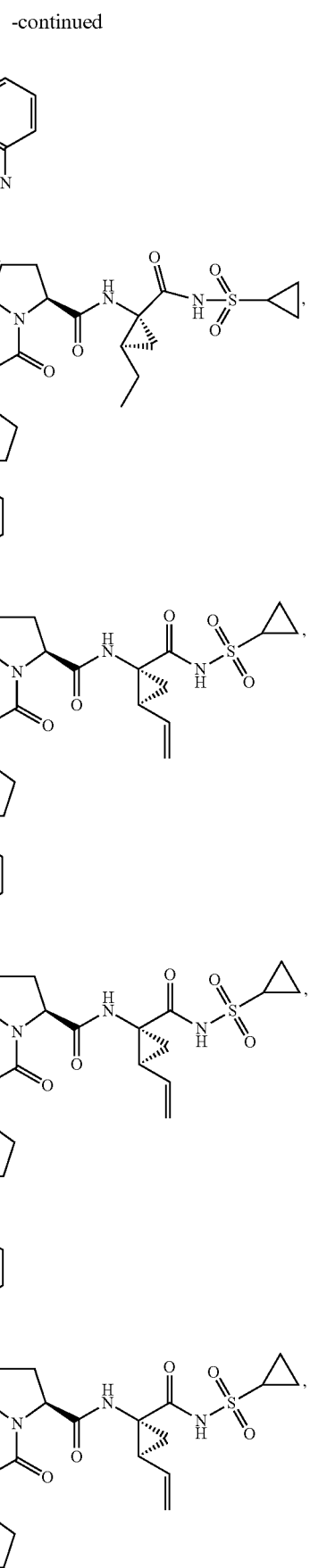

-continued

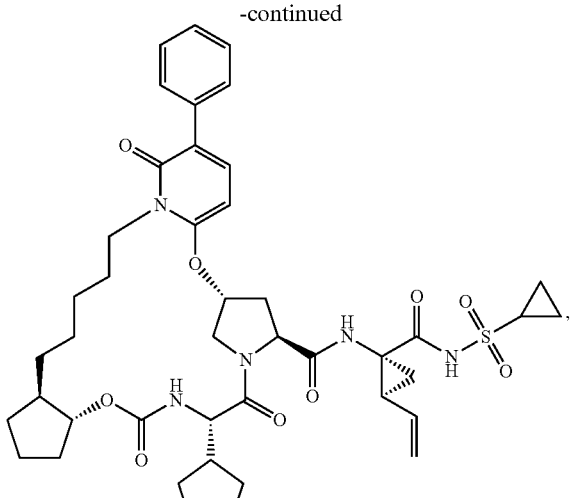

and

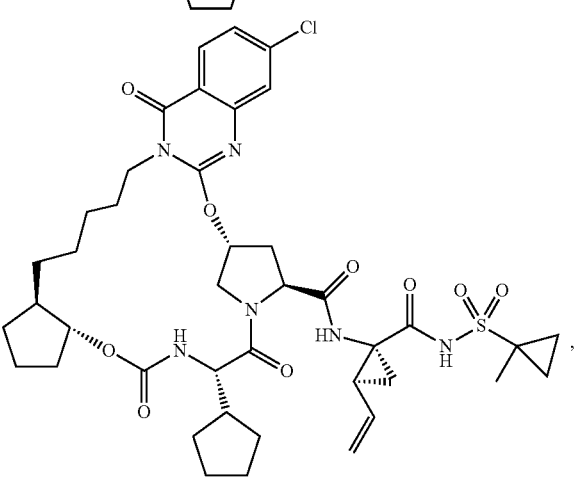

and

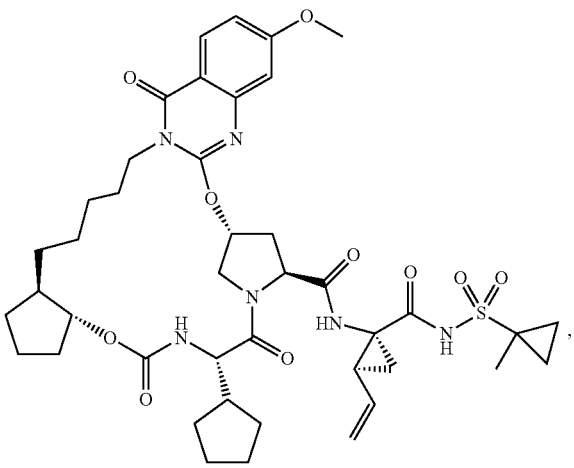

and pharmaceutical acceptable salts thereof.

18. A pharmaceutical composition comprising an effective amount of the compound according to claim 1, or a pharmaceutically acceptable salt thereof, and a pharmaceutically acceptable carrier.

19. The pharmaceutical composition according to claim 18, further comprising a second therapeutic agent selected from the group consisting of HCV antiviral agents, immunomodulators, and anti-infective agents.

20. The pharmaceutical composition according to claim 18, further comprising a second therapeutic agent selected from the group consisting of HCV protease inhibitors and HCV NS5B polymerase inhibitors.

21. A method of treating a patient infected with HCV comprising the step of administering to said patient a therapeutically effective amount of the compound according to claim 1.

22. A compound wherein said compound is

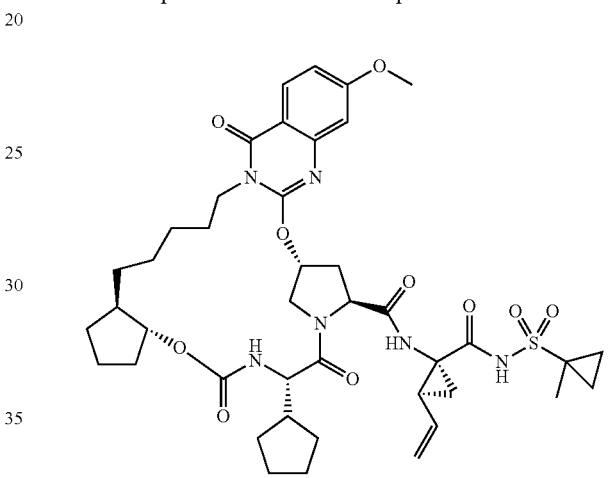

or a pharmaceutically acceptable salt thereof.

23. A pharmaceutical composition comprising an effective amount of the compound according to claim 22, or a pharmaceutically acceptable salt thereof, and a pharmaceutically acceptable carrier.

24. The pharmaceutical composition according to claim 23, further comprising a second therapeutic agent selected from the group consisting of HCV antiviral agents, immunomodulators, and anti-infective agents.

25. The pharmaceutical composition according to claim 23, further comprising a second therapeutic agent selected from the group consisting of HCV protease inhibitors and HCV NS5B polymerase inhibitors.

26. A method of treating a patient infected with HCV comprising the step of administering to said patient a therapeutically effective amount of the compound according to claim 22.

* * * * *